US008187856B2

(12) United States Patent
De Vries et al.

(10) Patent No.: US 8,187,856 B2
(45) Date of Patent: May 29, 2012

(54) RECOMBINANT HALOHYDRIN DEHALOGENASE POLYPEPTIDES

(75) Inventors: Erik De Vries, Livermore, CA (US);
Louis Clark, San Francisco, CA (US);
Scott McVicar, Sunnyvale, CA (US);
Erika Segraves, Sunnyvale, CA (US);
Shiwei Song, Singapore (SG); Kheng Lin Tan, Singapore (SG)

(73) Assignee: Codexis, Inc., Redwood City, CA (US)

( * ) Notice: Subject to any disclaimer, the term of this patent is extended or adjusted under 35 U.S.C. 154(b) by 298 days.

(21) Appl. No.: 12/642,586

(22) Filed: Dec. 18, 2009

(65) Prior Publication Data

US 2010/0173372 A1    Jul. 8, 2010

Related U.S. Application Data

(60) Provisional application No. 61/138,943, filed on Dec. 18, 2008.

(51) Int. Cl.
| | |
|---|---|
| *C12N 9/88* | (2006.01) |
| *C12N 15/00* | (2006.01) |
| *C12P 7/02* | (2006.01) |
| *C12P 21/06* | (2006.01) |
| *C07H 21/04* | (2006.01) |
| *C07K 1/00* | (2006.01) |

(52) U.S. Cl. ...... 435/232; 435/155; 435/69.1; 435/91.1; 435/320.1; 536/23.2; 530/350

(58) Field of Classification Search ............... 435/232, 435/155, 69.1, 91.1, 320.1; 536/23.2; 530/350
See application file for complete search history.

(56) References Cited

U.S. PATENT DOCUMENTS

| | | | |
|---|---|---|---|
| 4,284,723 | A | 8/1981 | Neidleman et al. |
| 5,166,061 | A | 11/1992 | Nakamura et al. |
| 5,210,031 | A | 5/1993 | Nakamura et al. |
| 5,430,171 | A | 7/1995 | Mitsuhashi et al. |
| 5,908,953 | A | 6/1999 | Matsuda et al. |
| 6,001,615 | A | 12/1999 | Reeve |
| 6,117,679 | A | 9/2000 | Stemmer et al. |
| 6,344,569 | B1 | 2/2002 | Mitsuda et al. |
| 6,376,246 | B1 | 4/2002 | Crameri et al. |
| 6,472,544 | B1 | 10/2002 | Kizaki et al. |
| 6,596,879 | B2 | 7/2003 | Bosch et al. |
| 6,645,746 | B1 | 11/2003 | Kizaki et al. |
| 6,689,591 | B2 | 2/2004 | Müller et al. |
| 7,125,693 | B2 | 10/2006 | Davis et al. |
| 7,132,267 | B2 | 11/2006 | Davis et al. |
| 7,541,171 | B2 | 6/2009 | Davis et al. |
| 7,588,928 | B2 | 9/2009 | Davis et al. |
| 2005/0153417 | A1 | 7/2005 | Davis et al. |
| 2006/0099700 | A1 | 5/2006 | Davis et al. |
| 2007/0161094 | A1 | 7/2007 | Davis et al. |
| 2008/0220485 | A1 | 9/2008 | Lutje-Spelberg et al. |
| 2008/0299626 | A1 | 12/2008 | Hauer et al. |
| 2010/0136617 | A1 | 6/2010 | Akiyama et al. |

FOREIGN PATENT DOCUMENTS

| | | |
|---|---|---|
| EP | 0879890 A1 | 5/1997 |
| EP | 1158054 A1 | 11/2001 |
| EP | 2130922 A1 | 9/2009 |
| JP | 04-278089 A | 10/1992 |
| JP | 10-210981 A | 8/1998 |
| WO | WO 98/53081 A1 | 11/1998 |
| WO | WO 01/90397 A1 | 11/2001 |
| WO | WO 2004/015132 A | 2/2004 |
| WO | WO 2005/017141 A1 | 2/2005 |
| WO | WO 2005/018579 A2 | 3/2005 |
| WO | 2007071599 A2 | 6/2007 |
| WO | 2007137816 A2 | 6/2007 |
| WO | 2007099107 A1 | 9/2007 |
| WO | 2007128469 A1 | 11/2007 |

OTHER PUBLICATIONS

Notification of Transmittal of the International Search Report and Written Opinion of the International Searching Authority, or the Declaration, PCT/US2009/068815, mailed Nov. 30, 2010.
De Vries et al., 2005, "Biocatalytic Production of Chiral Epoxides and Derivative," *Biocatalysis*, St Petersburg, Russia, Abstract Presentation.
Archer 1997, "Epoxide Hydrolases as Asymmetric Catalysts," Tetrahedron, Elsevier Science, 53(46):15617-15662.
Assis et al., 1998, "Biochemical characterization of a haloalcohol dehalogenase from Arthrobacter erithii H10a," *Enz. Microb. Tech.*, 22, 568-574.
Assis et al., 1998, "Synthesis of Chiral Epthalohydrins Using Haloalcohol Dehalogenase A from Arthrobacter Erithii H10a," *Enzyme Microb. Technol.* 22:545-551.
Bartnicki et al., 1969 "Biodehalogenation. The Pathway for Transhalogenation and the Stereochemistry of Epoxide Formation from Halohydrins," *Biochemistry*, 8, 4677-4680.
Besse et al., 1994, "Enantioselective Synthesis of Both Enantiomers of Cathinone via the Microbiological Reduction of 2-Azido-1-phenyl-1-propanone," *J. Org. Chem.*, 59(26):8288-8291.
Boyd et al., 1996, "Stereoselective Dioxygenase-Catalysed Benzylic Hydroxylation of Prochiral Methylene Groups in the Chemoenzymatic Synthesis of Enantiopure Vicinal Aminoindanols," Tetrahedron: Asymmetry, Elsevier Science, 7(6):1559-1562.
Campbell-Verduyn et al., 2010, "One pot 'click' reactions: tandem enantioselective biocatalytic epoxide ring opening and [3+2] azide alkyne cycloaddition," *J. Chem. Soc., Chem. Commun.* 46, 898-900.
Castro, et al., 1968, "Biodehalogenation. Epoxidation of Halohydrins, Epoxide Opening, and Transhalogenation by a *Flavobacterium*" *Biochemistry*, 7, 3213-3218.
De Jong et al., 2003, "Structure and Mechanism of a Bacterial Haloalcohol Dehalogenase: A New Variation of the Short-Chain Dehydrogenase/Reductase Fold Without an NAD(P)H Binding Site," *EMBO Journal*, 22(19):4933-4944, XP002305279, ISSN: 0261-4189.

(Continued)

*Primary Examiner* — Ganapathirama Raghu
(74) *Attorney, Agent, or Firm* — Codexis, Inc.

(57) ABSTRACT

The present disclosure provides engineered halohydrin dehalogenase (HHDH) polypeptides having improved enzyme properties as compared to the wild-type HHDH enzyme HheC and other reference engineered HHDH polypeptides. Also provided are polynucleotides encoding the engineered HHDH enzymes, host cells capable of expressing the engineered HHDH enzymes, and methods of using the engineered HHDH enzymes to synthesize a variety of chiral compounds including chiral epoxides and chiral alcohols.

19 Claims, No Drawings

OTHER PUBLICATIONS

De Jong et al., 2005, "Structural Basis for the Enantioselectivity of an Epoxide Ring Opening Reaction Catalyzed by Halo Alcohol Dehalogenase HheC," *J. Am. Chem. Soc.*, 127, 13338-13343.

De Jong et al., 2006, "The X-Ray structure of the haloalcohol dehalogenase HheA from Arthrobacter sp. Strain AD2: Insight into enantioselectivity and Halide Binding in the Haloalcohol Dehalogenase Family," *J. Bacteriol.*, 188, 4051-4056.

Effendi et al., 2000, "Isolation and Characterization of 2,3-Dichloro-1-Propanol-Degrading Rhizobia" *Appl. Environ. Microbiol.*, 66, 2882-2887.

Elenkov et al., 2004, "Enantioselective Ring Opening of Epoxides with Cyanide Catalyzed by Halohydrin Dehalogenases: A New Approach to Non-Racemic β-Hydroxy Nitriles," *Adv. Synth. Catal.* 348:579-585.

Faber et al., 1996, "Microbial Epoxide Hydrolases," *Acta Chemica Scand.*, 50, 249-258.

Fauzi, et al., 1996, "Biodehalogenation of low concentrations of 1,3-dichloropropanol by nono- and mixed cultures of bacteria," *Appl. Microbiol. Biotechnol.*, 46, 660-666.

Foelsche et al., 1990, "Lipase-Catalyzed Resolution of Acyclic Amino Alcohol Precursors," *J Org. Chem.*, 55(6):1749-1753.

Fox et al., 2007, "Improving catalytic function by ProSAR-driven enzyme evolution," *Nature Biotechnology*, 25, 338-344.

Fringuelli et al., 1999, "Ring Opening of Epoxides with Sodium Azide in Water: a Regioselective pH-Controlled Reaction," *J Org. Chem.* 63:6094-6096.

Fuchs et al., 2009, "Enantiocomplementary Chemoenzymatic Asymmetric Synthesis of (R)-and (5)-Chromanemethanol," *Eur. J. Org. Chem.*, 833-840.

Geigert et al., 1983, "Production of Epoxides from α, β-Halohydrins by *Flavobacterium*," *Appl. Environ. Microbiol.*, 45, 1148-1149.

Geigert, S. L. Neidleman In: A. I. Laskin, Editor, Enzymes and Immobilized Cells in Biotechnology: Enzymic Synthesis of Halohydrins and their Conversion to Epoxides (Biotechnology Series 5), Butterworth—Heinemann (1985), pp. 283-296.

Guy et al., 1992, "Selective Ring Opening Reaction of Styrene Oxide with Lithium Azide in the Presence of Cyclodextrins in Aqueous Media," *Tetrahedron Asymmetry* 3(2):247-250.

Haak et al., 2007, "Synthesis of enantiopure chloroalcohols by enzymatic kinetic resolution," *Org. Biomol. Chem.*, 5, 318-323.

Hallinan et al., 1995, "Yeast Catalysed Reduction of β-keto Esters (2): Optimisation of the Stereospecific Reduction by *Zygosaccharomyces rouxii*," *Biocatal. Biotransform.* 12:179-191.

Hardman et al., 1997, "Generation of Environmentally Enhanced Products: Clean Technology for Paper Chemicals", *J. Chem. Tech. Biotechnol.*, 70, 60-66.

Hasnaoui et al., 2005, "Catalytic promiscuity of halohydrin dehalogenase and its application in enantioselective epoxide ring opening," *Tetrahedron: Asymmetry*, 16, 1685-1692.

Hasnoui-Dijoux et al., 2008, "Catalytic Promiscuity of Halohydrin Dehalogenase and its Application in Enantioselective Epoxide Ring Opening," *ChemBioChem* 9:1048-1051.

Higgins et al., 2005, "Biochemical and molecular characterisation of the 2,3-dichloro-1-propanol dehalogenase and stereospecific haloalkanoic dehalogenases from a versatile *Agrobacterium* sp." *Biodegradation*, 16, 485-492.

Hopmann et al., 2008 "Cyanolysis and Azidolysis of Epoxides by Haloalcohol Dehalogenase: Theoretical Study of the Reaction Mechanism and Origins of Regioselectivity," *Biochemistry*, 47, 4973-4982.

Jorns, M.S., 1980, "Studies on the Kinetics of Cyanohydrin Synthesis and Cleavage by the Flavoenzyme Oxynitrilase," *Biochim Biophy. Acta* 613:203-209.

Kamal et al., 1992, "Stereoselective Synthesis of (S)-Propanol Amines: Lipase catalyzed opening of epoxides with 2-Propylamine," *Tetrahedron: Asymmetry*, 3, 1361-1364.

Kasai et al., 1990, "Degradation of 2,3-Dichloro-1-propanol by a *Pseudomonas*," *Agric. Biol. Chem.*, 54, 3185-3190.

Kasai et al., 1992, "Isolation of (s)-2,3-dichloro-1-propanol assimilating bacterium, its characterization, and its use in preparation of (R)-2,3-dichloro-1-propanol and (S)-epichlorohydrin," *J. Ind. Microbiol.*, 10, 37-43.

Kasai et al., 1998, "Chiral C3 Epoxides and Halohydrins: Their Preparation and Synthetic Application," *J. Molec. Cat. B: Enzymatic*, 4:237-252.

Kasai et al., 2003, "Industrialization of the Microbial Resolutionof Chrial C3 and C4 synthetic Units: From a small beginning to a Major Operation, a Personal Account" *Adv. Synth. Catal.*, 345, 437-455.

Larrow et al., 1996 "Kinetic Resolution of Terminal Epoxides via Highly Regioselective and Enantioselective Ring Opening with TMSN, An Efficient, Catalytic Route to 1,2-Amino Alcohols," *J. Am. Chem. Soc.*, 118(31):7420-7421.

Lewis et al., 1999, "Cloning and Nucleotide Sequence of the Haloalcohol Dehalogenase B Gene from *Agrobacterium tumefaciens*," Database Accession No. Q9WWB6, XP002152213.

Lewis, 1999, "*Agrobacterium tumefaciens* Haloalcohol Dehalogenase B Gene, Complete CDS," Database EMBL Online!, XP002305665, retrieved from EBI accession No. EM_PRO: AF149769, database accession No. AF149769.

Lutje Spelberg et al., 1998, "Enantioselectivity of a Recombinant Epoxide Hydrolase from Agrobacterium Radiobacter," Tetrahedron: Asymmetry, Elsevier Science, 9(3):459-466.

Lutje Spelberg et al., 1999, "A Tandem Enzyme Reaction to Produce Optically Active Halohydrins, Epoxides and Diols," Tetrahedron: Asymmetry, 10:2863-2870.

Lutje Spelberg et al., 2000, "Highly enantioselective and Regioselective Biocatalytic Azidiolysis of Aromatic Epoxides," *Org. Lett.*, 3, 41-43.

Lutje Spelberg et al., 2004, "Enzymatic dynamic kinetic resolution of epihalohydrins," *Tetrahedron: Asymmetry* 15:1095-1102.

Lutje Spelberg, 2002, "Exploration of the biocatalytic potential of a halohydrin dehalogenase using chromogenic substrates," *Tetrahedron: Asymmetry*, 13, 1083-1089.

Majeric-Elenkov et al., 2006, "Enantioselective ring opening of epoxides with cyanide catalysed by halohydrin dehalogenases: a new approach to non-racemic beta-hydroxy nitriles," *Adv. Synth. Catal.* 348, 579-585.

Majerić-Elenkov et al., 2006, "Sequential Kinetic Resolution Catalyzed by Halohydrin Dehalogenase," *Org. Lett.*, 8, 4227-4229.

Majerić-Elenkov et al., 2007, "Enzyme-Catalyzed nucleophilic ring opening of epoxides for the preparation of enantiopure tertiary alcohols," *Adv. Synth. Catal.*, 349, 2279-2285.

Majerić-Elenkov et al., 2008, "Formation of Enantiopure 5-Substituted Oxazolidinones through Enzyme-Catalysed Kinetic Resolution of Epoxides," *Org. Lett.*, 10, 2417-2420.

Martinez et al., 1995 "Highly Enantioselective Ring Opening of Epoxides Catalyzed by (salen)Cr(III)Complexes," *J. Am. Chem. Soc.*, 117(21):5897-5898.

Mischitz et al., 1994 "Asymmetric Opening of an Epoxide by Azide Catalyzed by an Immobilized Enzyme Preparation from *Rhodococcus* sp.," Tetrahedron Letters, 35(1):81-84.

Nagasawa, et al., 1992, "Purification and Characterization of Halohydrin Hydrogen-halide Lyase from a Recombinant *Escherichia coli* Containing the Gene from a *Corynebacterium* sp.," *Appl. Microbiol. Biotechnol.*, 36:478-482.

Nakamura et al., 1991, "A New Catalytic Function of Halohydrin Hydrogen-Halide-Lyase, Synthesis of β-Hydroxynitriles from Epoxides and Cyanide," *Biochem Biophys Res Commun.*, 180(1):124-30.

Nakamura et al., 1991, "Microbial Transformation of Prochiral 1,3-Dichlorooo-2-propanol into Optically Active 3-Chloro-1,2-propanediol", *Agric. Biol. Chem.*, 1931-1933.

Nakamura et al., 1992, "Resolution and Some Properties of Enzymes Involved in Enantioselective Transformation of 1,3-Dichloro-2-Propanol to (R)-3-Chloro-1,2-Propanediol by *Corynebacterium* sp. Strain N-1074," *J. Bacteriol.*, 174(23):7613-7619.

Nakamura et al., 1993, "Production of (R)-3-chloro-1,2-Propanediol from prochiral 1,3-dichloro-2-propanol by *Corynebacterium* sp. Strain N-1074," *Appl. Environ. Microbiol.*, 59, 227-230.

Nakamura et al., 1994, "A New Enzymatic Synthesis of (R)-γ-Chloro-β-Hydroxybutyronitrile," Tetrahedron, Elsevier Science, 50(41):11821-11826.

Nakamura, et al., 1994, "Characterization of a Novel Enantioselective Halohydrin Hydrogen-Halide-Lyase," *Appl. Environ. Microbiol.*, 60(4):1297-1301.

Poelarends et al., 1999, "Degradation of 1,2-Dibromoethane by *Mycobacterium* sp. Strain GP1," *J Bacteriol.*, 181(7):2050-2058.

Rink et al., Jun. 1997, "Primary Structure and Catalytic Mechanism of the Epoxide Hydrolase from *Agrobacterium radiobacter* AD1," *J. Biol. Chem.*, 272(23):14650-14657.

Schrittwieser et al., 2009, "Biocatalytic cascade for the synthesis of enantiopure β-azidoalcohols and β-hydrozynitriles,"*Eur. J. Org. Chem.*, 2293-2298.

Schrittwieser et al., 2009, "Shifting the equilibrium of a biocatalytic cascade synthesis to enantiopure epoxides using anion exchangers," *Tetrahedron: Asymmetry*, 20, 483-488.

Seisser et al., 2007, "Stereo-complementary two-step cascades using a two-enzyme system leading to enantiopure epoxides," *Adv. Synth. Catal.*, 349, 1399-1404.

SEQ ID No: 2 Comparison to Accession No. AAW69435 in JP1020981 A1, Aug. 11, 1998.

Straathof et al., Dec 1997, "The Enantiomeric Ratio: Origin, Determination and Prediction," *Enzyme Microb. Technol.*, 21:559-571.

Suzuki et al., 1991, "A Novel Method for the Generation of (R)- and (S)-3-Chloro-1,2-Propanediol by Stereospecific Dehalogenating Bacterial and their Use in the Preparation of (R) and (S)-Glycidol, " *Bioorg. Med. Chem. Lett.*, 1, 343-346.

Suzuki et al., 2003, "Generation of Optically Active Glycerol Derivatives by Microbial Resolution—for Development and Useful Synthetic Units for Pharmaceuticals," *Trends in Glycoscience and Glycotechnology*, 15, 329-349.

Swanson, P. E., 1999, "Dehalogenases Applied to Industrial-Scale Biocatalysis," *Curr. Opin. Biotechnol.*, 10:365-369.

Tang et al., 2002, "Improved Stability of Halohydrin Dehalogenase from *Agrobacterium radiobacter* AD1 by Replacement of Cysteine Residues," *Enzyme. Microb. Technol.*, 30:231-258.

Tang et al., 2003, "Steady-State kinetics and tryptophan fluorescence properties of halohydrin dehalogenase from *Agrobacterium radiobacter*. Roles of W139 and W249 in the Active Site and Halide-Induced Conformational Change," *Biochemistry*, 42, 14057-14065.

Tang et al., 2005, "Improved catalytic properties of halohydrin dehalogenase by modification of the halide-binding site," *Biochemistry*, 44, 6609-6618.

Van Den Wijngaard et al., 1989, "Degradation of Epichlorohydrin and Halohaldrins by Bacterial Cultures Isolated from Freshwater Sediment", *J. Gen. Microbiol.*, 135, 2199-2208.

Van Den Wijngaard et al., 1991, "Purification and Characterization of Haloalcohol Dehalogenase from *Arthrobacter* sp. Strain AD2," *J. Bacteriol.*, 173(1):124-129.

Van Hylckama et al., 2001, "Halohydrin Dehalogenases are Structurally and Mechanistically Related to Short-Chain Dehydrogenases/Reductases," *Journal of Bacteriology*, 183(17):5058-5066, XP002305277, ISSN: 0021-9193.

Wandel et al.,1994,"Enantioselectivity of Epoxide Formation from Halohydrins by Means of Flavobacterium Rigense," *Biocatalysis*, 10, 159.

Wells, P. R., "Linear Free Energy Relationships," *Chem Rev.* 63:171-219, 1968.

Yu et al., 1994, "Cloning of Two Halohydrin Hydrogen-Halide-Lyase Genes of *Corynebacterim* sp. Strain N-I074 and Structural Comparison of the Genes and Gene Products," *Biosci., Biotechnol., Biochem.* 58(8):1451-1457.

RECOMBINANT HALOHYDRIN DEHALOGENASE POLYPEPTIDES

1. CROSS REFERENCE TO RELATED APPLICATIONS

The present application claims priority of U.S. provisional application 61/138,943, filed Dec. 18, 2008, which is hereby incorporated by reference herein.

2. REFERENCE TO SEQUENCE LISTING, TABLE OR COMPUTER PROGRAM

The Sequence Listing concurrently submitted herewith under 37 C.F.R. §1.821 in a computer readable form (CRF) via EFS-Web as file name CX2-027US1_ST25.txt is herein incorporated by reference. The electronic copy of the Sequence Listing was created on Dec. 17, 2009, with a file size of 517 Kbytes. This Sequence Listing is identical except for minor formatting corrections to file 376247-036USP1.txt created on Dec. 18, 2008, with a file size of 508 Kbytes, which was incorporated by reference in the priority U.S. provisional application 61/138,943.

3. BACKGROUND

Enzymes belonging to the halohydrin dehalogenase (HHDH), also named halohydrin hydrogen-halide-lyase or halohydrin epoxidase, class (EC 4.5.1) catalyze the interconversion of 1,2-halohydrins and the corresponding 1,2-epoxides as shown below in Scheme 1.

Scheme 1

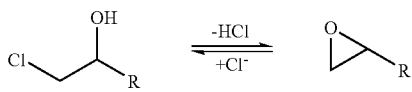

U.S. Pat. No. 4,284,723 describes the use of a halohydrin epoxidase for the production of propylene oxide. U.S. Pat. Nos. 5,166,061 and 5,210,031 describe the use of this enzyme activity for the conversion of 1,3-dichloropropanol (DCP) and epichlorohydrin (ECH) respectively to 4-chloro-3-hydroxybutyronitrile (CHBN). HHDH enzymes from *Agrobacterium radiobacter* and *Corynebacterium* have been characterized on a broad range of halogenated substrates (Van Hylckama Vlieg et al., *J. Bacteriol*. (2001) 183:5058-5066; Nakamura et al., *Appl. Environ. Microbiol*. (1994) 60:1297-1301; Nagasawa et al., *Appl. Microbiol. Biotechnol*. (1992) 36:478-482).

HHDH also catalyzes the ring opening of epoxides with nucleophiles other than chloride or bromide as shown in Scheme 2 (see e.g., Nakamura et al., *Biochem. Biophys Res. Comm*. (1991) 180:124-130; Nakamura et al., *Tetrahedron* (1994) 50: 11821-11826; Lutje Spelberg et al., *Org. Lett*. (2001) 3:41-43; Lutje Spelberg et al., *Tetrahedron Asymm*. (2002) 13:1083).

Scheme 2

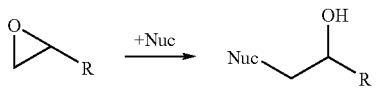

Nakamura et al. (Tetrahedron (1994) 50: 11821-11826) describe the use of HHDH for the direct conversion of DCP to chloro-3-hydroxy-butyronitrile (CHBN) through epichlorohydrin (ECH) as the intermediate as shown below in Scheme 3.

Scheme 3

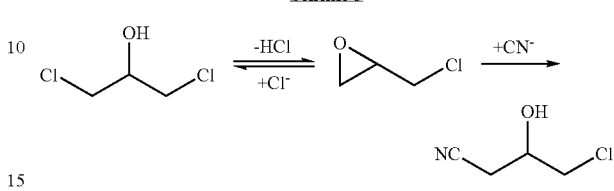

Some halohydrin dehalogenases have been characterized. For example, HHDH from *A. radiobacter* AD1 is a homotetramer of 28 kD subunits. *Corynebacterium* sp. N-1074 produces two HHDH enzymes, one of which, enzyme Ia, is composed of 28 kD subunits, while the other, enzyme Ib. is composed of related subunits of 35 and/or 32 kD. HHDH from some sources is easily inactivated under oxidizing conditions in a process that leads to dissociation of the subunits, has a pH optimum from pH 8 to 9 and an optimal temperature of 50° C. (Tang, *Enz. Microbial Technol*. (2002) 30:251-258; Swanson, *Curr. Opin. Biotechnol*. (1999) 10:365-369). The optimal pH for HHDH catalyzed epoxide formation has been reported as 8.0 to 9.0 and the optimal temperature in the range of from 45° C. to 55° C. (see e.g., Van Hylckama Vlieg et al., *J. Bacteriol*. (2001) 183:5058-5066; Nakamura et al., *Appl. Environ. Microbiol*. (1994) 60:1297-1301; Nagasawa et al., *Appl. Microbiol. Biotechnol*. (1992) 36:478-482). The optimal pH for the reverse reaction, ring opening by chloride, has been reported for the two *Corynebacterium* sp. N-1074 enzymes Ia and Ib and is pH 7.4 and pH 5, respectively. Site directed mutagenesis studies on the *A. radiobacter* AD1 HHDH indicated that oxidative inactivation is due to disruption of the quaternary structure of the enzyme by oxidation of cysteine residues (Tang et al., *Enz. Microbial Technol*. (2002) 30:251-258).

Purified HHDH enzymes from different sources exhibit specific activities on DCP ranging from 146 U/mg (Ib) to 2.75 U/mg (Ia) (Nakamura et al., *Appl. Environ. Microbiol*. 1994 60:1297-1301; Nagasawa et al., *Appl. Microbiol. Biotechnol*. (1992) 36:478-482). The high activity of the Ib enzyme is accompanied by a high enantioselectivity to produce R-ECH from DCP, while the Ia enzyme produces racemic ECH.

HHDH encoding genes have been identified in *Agrobacterium radiobacter* AD1 (hheC), *Agrobacterium tumefaciens* (halB), *Corynebacterium* sp (hheA encoding Ia and hheB encoding Ib), *Arthrobacter* sp. (hheA$_{AD2}$), and *Mycobacterium* sp. GP1 (hheB$_{Gp1}$). All enzymes have been functionally expressed in *E. coli*.

It is highly desirable for commercial applications that an HHDH enzyme exhibits high volumetric productivity, that reactions run to completion in a relatively short period of time, with a high final product concentration, with high enantioselectivity and regioselectivity, exhibits minimal inhibition by reaction components, and that generation of undesirable chemical side products is reduced. It is also desirable to have an HHDH enzyme capable of catalyzing ring opening or ring closure on a range of substrates (Hasnaoui-Dijoux et al., 2008, Chem. Biochem. 9:1048-1051; Tang et al., 2003, Biochemistry 42:5378-5386; Lutje Spelberg et al., 2000, Org. Lett. 3(1):41-43; Lutje Spelberg et al., 1998, Tetrahedron Asymmetry 9:459-466; and Majeric-Elenkov et al., Organic Letters 10 (12), pg 2417-2420, 2008).

4. SUMMARY

Provided in the present disclosure are engineered halohydrin dehalogenase (HHDH) polypeptides having altered or improved enzyme properties, including, among others, changes to substrate recognition, enantioselectivity, halide ion resistance, and regioselectivity. These changes allow the engineered HHDHs to be used in biocatalytic applications for preparing compounds not efficiently produced by other HHDH polypeptides.

In some embodiments the disclosure provides an engineered halohydrin dehalogenase (HHDH) polypeptide having an improved enzyme property relative to one or both of the reference polypeptides of SEQ ID NO: 244 or SEQ ID NO: 4, where the engineered HHDH comprising an amino acid sequence at least 80% identical to SEQ ID NO: 244 or SEQ ID NO: 4, and at least one residue difference as compared to SEQ ID NO:244 at a position selected from: X34; X51; X81; X85; X110; X131; X167; X232; X242; X248, and X254. In certain embodiments the residue difference is selected from: X34 is G; X51 is P; X81 is E, F, M, W, or Y; X85 is V; X110 is S; X131 is A; X167 is H; X232 is S; X242 is A; X248 is V; and X254 is N.

In some embodiments the disclosure provides an engineered HHDH having an improved enzyme property relative to one or both of the reference polypeptides of SEQ ID NO: 244 or SEQ ID NO: 4, wherein the engineered HHDH comprises an amino acid sequence at least 80% identical to SEQ ID NO:244 and has and at least one residue difference as compared to SEQ ID NO:244 selected from: X12 is M, or S; X34 is G; X51 is P; X81 is E, F, M, W, or Y; X82 is C, G, K, L, M, N, or W; X83 is C or E; X84 is D; X85 is V; X86 is A or H; X110 is S, X131 is A; X134 is C, F, I, K, L, M, or V; X139 is G, I, L, M, P, S, T, or V; X142 is C, M or N; X146 is P; X167 is H; X175 is C, G, I, L, M, N, or V; X176 is F, M, Q, or T; X177 is L, S or T; X178 is T; X182 is S; X186 is H; X187 is G, I, or S; X201 is R; X232 is S, X242 is A; X243 is C or L; X245 is S; X246 is S; X247 is N; X248 is V; X249 is A, G, H, I, or S; X252 is C; and X254 is N.

In some embodiments the disclosure provides an engineered HHDH having an improved enzyme property relative to one or both of the reference polypeptides of SEQ ID NO: 244 or SEQ ID NO: 4 comprises an amino acid sequence selected from the group consisting of SEQ ID NO: 2, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 246, 248, 250, 252, 254, 256, 258, 260, 262, 264, 266, 268, 270, 272, 274, 276, 278, 280, 282, 284, 286, 288, 290, 292, 294, 296, 298, 300, 302, and 304.

In some embodiments the engineered HHDH polypeptides of the disclosure are capable of converting a racemic epoxide substrate of formula (I) (see infra, e.g., styrene oxide) to an S-alcohol product of formula (II) with an increased enantiomeric excess of product as compared to reference polypeptide of SEQ ID NO: 4 or 244.

In some embodiments the engineered HHDH polypeptides of the disclosure are capable of an increased R-stereoselectivity in converting the epoxide of formula (I) (see infra, e.g., styrene oxide) to the R-alcohol product of formula (III) as compared to a reference polypeptide of SEQ ID NO: 4 or 244.

In some embodiments the engineered HHDH polypeptides of the disclosure are capable of increased α-regioselectivity or β-regioselectivity in the conversion of an epoxide substrate of formula (I) (see infra, e.g., styrene oxide) to a product of formula (II) as compared to a reference polypeptide of SEQ ID NO: 4 or 244.

In some embodiments the engineered HHDH polypeptides of the disclosure are capable of increased refractoriness to inhibition by a halide ion as compared to a reference HHDH polypeptide of SEQ ID NO: 4 or 244. In some embodiments, the halide ion is selected from Br$^-$, Cl$^-$, or I$^-$.

In some embodiments the engineered HHDH polypeptides of the disclosure are capable of an increased activity for converting an epoxide substrate of formula (I) to an alcohol product of formula (II) as compared to a reference polypeptide of SEQ ID NO: 4 or 244, wherein the epoxide substrate is cis- or trans-2,3-epoxybutane.

In some embodiments the engineered HHDH polypeptides of the disclosure are capable of an increased rate for converting a non-terminal epoxide to the corresponding alcohol product as compared to a reference polypeptide of SEQ ID NO: 4 or 244.

In some embodiments the engineered HHDH polypeptides of the disclosure are capable of an increased rate of converting the haloalcohol of formula (II) to the epoxide of formula (I) as compared to a reference polypeptide of SEQ ID NO: 4 or 244.

In some embodiments the engineered HHDH polypeptides of the disclosure are capable of catalyzing a ring closure reaction converting alcohol substrate of formula (II) to an epoxide product of formula (I) with an increased enantiomeric excess of as compared to a reference polypeptide of SEQ ID NO: 244. In some embodiments of the catalyzed ring closure reaction the alcohol substrate of formula (II) is para-nitro-styrene-hydroxy-halide (PNSHH) and the epoxide product of formula (I) formed in enantiomeric excess is either R- or S-para-nitro-styrene oxide (PNSO).

In another aspect, the present disclosure provides polynucleotides encoding any of the engineered HHDH polypeptides, as well as vectors and host cells comprising the polynucleotides.

In another aspect, the present disclosure provides methods of using the engineered HHDH polypeptides. In some embodiments, the disclosure provide a method of converting an epoxide of formula (I) to an alcohol of formula (II) (in a reaction scheme as shown below)

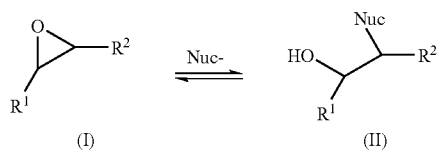

wherein, $R^1$ is a substituted or unsubstituted alkyl, cycloalkyl, heteocycloalkyl, aryl, or heteroaryl; $R^2$ is H, or substituted or unsubstituted alkyl, cylcoalkyl, heteocycloalkyl, aryl, or heteroaryl; or wherein $R^1$ and $R^2$ forms a ring; and said method comprises contacting the epoxide of formula (I) with an engineered HHDH of the disclosure in the presence of a nucleophile (Nuc$^-$) under reaction conditions suitable for converting the epoxide to the alcohol product.

In certain embodiments, the method can be carried out wherein the epoxide of formula (I) is a terminal epoxide. In some embodiments, the method can be carried out wherein $R^1$ is a substituted or unsubstituted aryl group, or substituted or unsubstituted phenyl group; or, wherein the epoxide is selected from the group consisting of: styrene oxide; para-nitrostyrene oxide; benzylethylene oxide; 1,2-epoxybutane; and 1,2 epoxyhexane; or wherein $R^1$ and $R^2$ forms a ring comprising a substituted or unsubstituted cycloalkyl or heterocycloalkyl group. In certain embodiments, the method can be carried out wherein the nucleophile ($Nuc^-$) is selected from: $Br^-, Cl^-, I^-, NO_2^-, N_3^-, CN^-, OCN^-, SCN^-$, or formate.

5. DETAILED DESCRIPTION

1.1 Abbreviations

The abbreviations used for the genetically encoded amino acids are conventional and are as follows:

| Amino Acid | Three-Letter | One-Letter Abbreviation |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | HIS | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

1.2 Definitions

As used herein, the following terms are intended to have the following meanings.

"Halohydrin Dehalogenase" and "HHDH" are used interchangeably herein to refer to a polypeptide having an enzymatic capability of converting an epoxide group to a haloalcohol. In some embodiments, the HHDH is also capable of converting a haloalcohol to an epoxide. More specifically, the HHDH polypeptides of the invention are capable of stereoselectively converting the compound of formula (I), infra to the corresponding product of formula (II), infra. The polypeptide can utilize azide ($N_3^-$) or another nucleophile, such as $Br^-, Cl^-, I^-, NO_2^-, CN^-, OCN^-, SCN^-$, or formate ($HCOO^-$). Halohydrin dehalogenases as used herein include naturally occurring (wild type) halohydrin dehalogenases as well as non-naturally occurring engineered polypeptides generated by human manipulation.

"Coding sequence" refers to that portion of a sequence of nucleic acids (e.g., a gene) that encodes an amino acid sequence of a protein.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" or "engineered" or "non-naturally-occurring" when used with reference to, e.g., a cell, nucleic acid sequence, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, *Adv. Appl. Math.* 2:482, by the homology alignment algorithm of Needleman and Wunsch, 1970, *J. Mol. Biol.* 48:443, by the search for similarity method of Pearson and Lipman, 1988, *Proc. Natl. Acad. Sci. USA* 85:2444, by computerized implementations of these algorithms (GAP, BESTFIT, FASTA, and TFASTA in the GCG Wisconsin Software Package), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, *J. Mol. Biol.* 215: 403-410 and Altschul et al., 1977, *Nucleic Acids Res.* 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, *Proc Natl Acad Sci USA* 89:10915). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a "comparison window" to identify and compare local regions of sequence similarity. In some embodiments, a "reference sequence" can be based on a primary amino acid sequence, where the reference sequence is a sequence that can have one or more changes in the primary sequence. For instance, a "reference sequence based on SEQ ID NO: 4 having at the residue corresponding to X202 a leucine" refers to a reference sequence in which the residue at a position 202 in SEQ ID NO: 4 has been changed to a leucine. The term "reference sequence" is not intended to be limited to wild-type sequences, and can include engineered sequences. For example, in some embodiments, a "reference sequence" can be the previously engineered polypeptide sequences of SEQ ID NO: 4 or SEQ ID NO: 244.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered halohydrin dehalogenase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess.

"Highly stereoselective" refers to a halohydrin dehalogenase polypeptide that is capable of converting the substrate to the corresponding product having the chemical formula (II) or (III) with at least about 85% stereomeric excess.

"Stereospecificity" refers to the preferential conversion in a chemical or enzymatic reaction of one stereoisomer over another. Stereospecificity can be partial, where the conversion of one stereoisomer is favored over the other, or it may be complete where only one stereoisomer is converted.

"Chemoselectivity" refers to the preferential formation in a chemical or enzymatic reaction of one product over another.

"Regioselectivity" refers to the preference of one direction of bond making or breaking over another. For example, nucleophilic attack in the conversion of an epoxide compound of formula (I) infra, to an alcohol compound of formula (II) infra can be regioselective for either the α or β-carbon of the epoxide. The α or β-carbon of an epoxide compound are illustrated as follows:

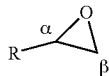

Exemplary epoxide ring-opening products exhibiting α-regioselectivity would include:

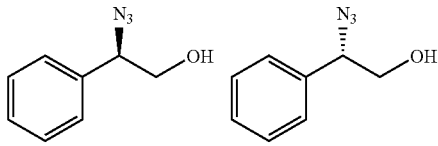

Whereas, exemplary epoxide ring-opening products exhibiting β-regioselectivity would include:

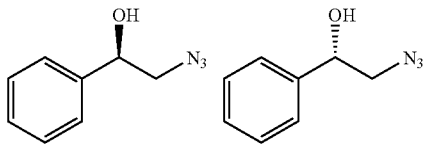

"Non-terminal epoxide" refers to an epoxide having the following structure:

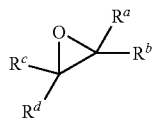

wherein at least one of $R^a$ and $R^b$ and one of $R^c$ and $R^d$ is a carbon atom, such as a substituted or unsubstituted alkyl or aryl, and including carbon atoms forming a ring, such as in the case of cyclic epoxides.

"Cyclic epoxide" refers to an epoxide of the following structure:

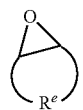

wherein, $R^e$ is a carbon ring, for example, substituted or unsubstituted cycloalkyl or heterocycloalkyl. Exemplary carbon rings, include, among others, cyclopentyls, such as cyclopentanyl and cyclopentenyl, and cyclohexanyl and cyclohexenyl. The carbon ring can also comprise of two rings fused to each other.

"Improved enzyme property" refers to a halohydrin dehalogenase polypeptide that exhibits an improvement in any enzyme property as compared to a reference halohydrin dehalogenase. For the engineered halohydrin dehalogenase polypeptides described herein, the comparison is generally made to the wild-type halohydrin dehalogenase enzyme, although in some embodiments, the reference halohydrin dehalogenase can be another improved engineered halohydrin dehalogenase. Enzyme properties for which improvement is desirable include, but are not limited to, enzymatic activity (which can be expressed in terms of percent conversion of the substrate), thermal stability, solvent stability, pH activity profile, refractoriness to inhibitors (e.g., product inhibition), stereospecificity, and stereoselectivity (including enantioselectivity), as well as regioselectivity.

"Increased enzymatic activity" refers to an improved property of the engineered halohydrin dehalogenase polypeptides, which can be represented by an increase in specific activity (e.g., product produced/time/weight protein) or an increase in percent conversion of the substrate to the product (e.g., percent conversion of starting amount of substrate to product in a specified time period using a specified amount of HHDH) as compared to the reference halohydrin dehalogenase enzyme. Exemplary methods to determine enzyme activity are provided in the Examples. Any property relating to enzyme activity may be affected, including the classical enzyme properties of $K_M$, $V_{max}$ or $k_{cat}$, changes of which can lead to increased enzymatic activity. Improvements in enzyme activity can be from about 1.5 times the enzymatic activity of the corresponding wild-type halohydrin dehalogenase enzyme, to as much as 2 times, 5 times, 10 times, 20 times, 25 times, 50 times, 75 times, 100 times, or more enzymatic activity than the naturally occurring halohydrin dehalogenase or another engineered halohydrin dehalogenase from which the halohydrin dehalogenase polypeptides were derived. In specific embodiments, the engineered halohydrin dehalogenase enzyme exhibits improved enzymatic activity in the range of 1.5 to 50 times, 1.5 to 100 times greater than that of the parent halohydrin dehalogenase enzyme. It is understood by the skilled artisan that the activity of any enzyme is diffusion limited such that the catalytic turnover rate cannot exceed the diffusion rate of the substrate. The theoretical maximum of the diffusion limit, or $k_{cat}/K_m$, is generally about $10^8$ to $10^9$ $(M^{-1}s^{-1})$. Hence, any improvements in the enzyme activity of the halohydrin dehalogenase will have an upper limit related to the diffusion rate of the substrates acted on by the halohydrin dehalogenase enzyme. Halohydrin dehalogenase activity can be measured by any one of standard assays used for measuring reaction rates. Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Inhibition constant" or "$K_i$" are used interchangeably herein to refer to the inhibition constant of an inhibitor for the enzyme as commonly understood by those skilled in the art. These include the classical descriptions of $K_i$ for competitive, uncompetitive, and non-competitive inhibitors.

"Conversion" refers to the enzymatic transformation of the substrate to the corresponding product. "Percent conversion" refers to the percent of the substrate that is converted to the product within a period of time under specified conditions. Thus, the "enzymatic activity" or "activity" of a halohydrin dehalogenase polypeptide can be expressed as "percent conversion" of the substrate to the product within a certain time period.

"Thermostable" refers to a halohydrin dehalogenase polypeptide that maintains similar activity (more than 60% to 80% for example) after exposure to elevated temperatures (e.g., 40-80° C.) for a period of time (e.g., 0.5-24 hrs) compared to the untreated enzyme.

"Solvent stable" refers to a halohydrin dehalogenase polypeptide that maintains similar activity (more than e.g., 60% to 80%) after exposure to varying concentrations (e.g., 5-99%) of solvent (, tetrahydrofuran, 2-methyltetrahydrofuran, toluene, butylacetate, methyl tert-butylether, etc.) for a period of time (e.g., 0.5-24 hrs) compared to the untreated enzyme.

"pH stable" refers to a halohydrin dehalogenase polypeptide that maintains similar activity (more than e.g., 60% to 80%) after exposure to high or low pH (e.g., 4.5-6 or 8 to 12) for a period of time (e.g., 0.5-24 hrs) compared to the untreated enzyme.

"Thermo- and solvent stable" refers to a halohydrin dehalogenase polypeptide that is both thermostable and solvent stable.

"Derived from" as used herein in the context of engineered halohydrin dehalogenase enzymes, identifies the originating halohydrin dehalogenase enzyme, and/or the gene encoding such halohydrin dehalogenase enzyme, upon which the engineering was based. For example, the engineered halohydrin dehalogenase enzyme of SEQ ID NO: 60 was obtained by artificially evolving, over multiple generations the gene encoding the *Agrobacterium radiobacter* halohydrin dehalogenase enzyme HheC (accession: gi|15213643|gb|AAK92099.1|AF397296_1 halohydrin dehalogenase). Thus, this engineered halohydrin dehalogenase enzyme is "derived from" the wild-type HheC halohydrin dehalogenase.

"Hydrophilic amino acid or residue" refers to an amino acid or residue having a side chain exhibiting a hydrophobicity of less than zero according to the normalized consensus hydrophobicity scale of Eisenberg et al., 1984, *J. Mol. Biol.* 179:125-142. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R).

"Acidic amino acid or residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic amino acid or residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar amino acid or residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Hydrophobic amino acid or residue" refers to an amino acid or residue having a side chain exhibiting a hydrophobicity of greater than zero according to the normalized consensus hydrophobicity scale of Eisenberg et al., 1984, *J. Mol. Biol.* 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic amino acid or residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue" (see below).

"Constrained amino acid or residue" refers to an amino acid or residue that has a constrained geometry. Herein, constrained residues include L-pro (P) and L-his (H). Histidine has a constrained geometry because it has a relatively small imidazole ring. Proline has a constrained geometry because it also has a five membered ring.

"Non-polar amino acid or residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic amino acid or residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Cysteine" or L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Small amino acid or residue" refers to an amino acid or residue having a side chain that is composed of a total three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Hydroxyl-containing amino acid or residue" refers to an amino acid containing a hydroxyl (—OH) moiety. Genetically-encoded hydroxyl-containing amino acids include L-Ser (S) L-Thr (T) and L-Tyr (Y).

"Amino acid difference" or "residue difference" refers to a change in the residue at a specified position of a polypeptide sequence when compared to a reference sequence. For example, a residue difference at position X139, where the reference sequence has a tryptophan, refers to a change of the residue at position X139 to any residue other than tryptophan. As disclosed herein, an enzyme can include one or more residue differences relative to a reference sequence, where multiple residue differences typically are indicated by a list of the specified positions where changes are made relative to the reference sequence (e.g., "one or more residue differences as compared to SEQ ID NO: 244 at the following residue positions: X34; X51; X81; X85; X110; X131; X167; X232; X242; X248; and X254."). Accordingly, a "group of residue differences" or "combination of residue differences" refers to a defined set of residue differences (e.g., "one or more groups of residue differences selected from: X139 is M, and X176 is S; X139 is M, and X176 is T; and X139 is S, and X176 is T.").

"Conservative" amino acid substitutions or mutations refer to the interchangeability of residues having similar side chains, and thus typically involves substitution of the amino acid in the polypeptide with amino acids within the same or similar defined class of amino acids. However, as used herein, in some embodiments, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. Table 1 below shows exemplary conservative substitutions.

TABLE 1

| Residue | Possible Conservative Mutations |
| --- | --- |
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S, T | Other polar |
| Y, W, F | Other aromatic (Y, W, F) |
| C | None |

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g., proline for glycine) (b) the charge or hydrophobicity, or (c) the bulk of the side chain.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, up to 20% of the total number of amino acids, or up to 30% of the total number of amino acids making up the polypeptide while retaining enzymatic activity and/or retaining the improved properties of an engineered halohydrin dehalogenase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered halohydrin dehalogenase enzymes comprise insertions of one or more amino acids to the naturally occurring halohydrin dehalogenase polypeptide as well as insertions of one or more amino acids to other improved halohydrin dehalogenase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length halohydrin dehalogenase polypeptide, for example the polypeptide of SEQ ID NO:2, 4, or 86.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved halohydrin dehalogenase enzymes may be present within a cell, present in the cellular medium, or prepared in various forms, such as lysates or isolated preparations. As such, in some embodiments, the improved halohydrin dehalogenase enzyme can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure halohydrin dehalogenase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved halohydrin dehalogenases polypeptide is a substantially pure polypeptide composition.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The $T_m$ values for polynucleotides can be calculated using known methods for predicting melting temperatures (see, e.g., Baldino et al., *Methods Enzymology* 168:761-777; Bolton et al., 1962, *Proc. Natl. Acad. Sci. USA* 48:1390; Bresslauer et al., 1986, *Proc. Natl. Acad. Sci. USA* 83:8893-8897; Freier et al., 1986, *Proc. Natl. Acad. Sci. USA* 83:9373-9377; Kierzek et al., *Biochemistry* 25:7840-7846; Rychlik et al., 1990, *Nucleic Acids Res* 18:6409-6412 (erratum, 1991, *Nucleic Acids Res* 19:698); Sambrook et al., supra); Suggs et al., 1981, In *Developmental Biology Using Purified Genes* (Brown et al., eds.), pp. 683-693, Academic Press; and Wetmur, 1991, *Crit. Rev Biochem Mol Biol* 26:227-259. All publications incorporate herein by reference). In some embodiments, the polynucleotide encodes the polypeptide disclosed herein and hybridizes under defined conditions, such as moderately stringent or highly stringent conditions, to the complement of a sequence encoding an engineered halohydrin dehalogenase enzyme of the present disclosure.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA; with greater than about 90% identity to target-polynucleotide. Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the halohydrin dehalogenases enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, *Bioinformatics* 14:372-73; Stenico et al., 1994, Nucleic Acids Res. 222437-46; Wright, F., 1990, Gene 87:23-29). Codon usage tables are available for a growing list of organisms (see for example, Wada et al., 1992, *Nucleic Acids Res.* 20:2111-2118; Nakamura et al., 2000, *Nucl. Acids Res.* 28:292; Duret, et al., supra; Henaut and Danchin, "*Escherichia coli* and *Salmonella,*" 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., *Bioinformatics: Sequence and Genome Analysis*, Chapter 8, Cold Spring Harbor Laboratory Press, Cold Spring Harbor, N.Y., 2001; Uberbacher, E. C., 1996, *Methods Enzymol.* 266:259-281; Tiwari et al., 1997, *Comput. Appl. Biosci.* 13:263-270).

"Control sequence" is defined herein to include all components, which are necessary or advantageous for the expression of a polypeptide of the present disclosure. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" is a nucleic acid sequence that is recognized by a host cell for expression of a polynucleotide of interest, such as a coding sequence. The control sequence may comprise an appropriate promoter sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

1.3 Engineered Halohydrin Dehalogenase Polypeptides

As discussed above, halohydrin dehalogenases are a class of enzymes capable of mediating the following reaction (Scheme 4):

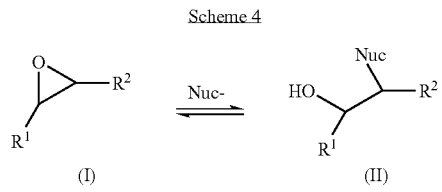

Scheme 4 wherein, the nucleophile (Nuc⁻) can be, among others, Br⁻, Cl⁻, I⁻, $NO_2^-$, $N_3^-$, CN⁻, OCN⁻, SCN⁻, or formate (HCOO⁻). For the wild type *A. radiobacter* HheC, the enzyme acts generally on epoxides where $R^2$ is H and $R^1$ is an alkyl or aryl group. The wild type HheC shows R-stereoselectivity for the alcohol product, regioselectivity for ring opening of styrene oxides mainly at the β position, and a preference for ring opening of terminal epoxides and ring closure of haloalcohols towards terminal epoxides. *A. radiobacter* HheC is also strongly inhibited by halide, which is a disadvantage where an efficient ring closure of haloalcohol to epoxide is needed or in processes where halides are present for other reasons.

Accordingly, provided in the present disclosure are engineered halohydrin dehalogenase (HHDH) polypeptides having altered or improved enzyme properties, including, among others, changes to substrate recognition, enantioselectivity, halide ion resistance, and regioselectivity. These changes allow the engineered HHDHs to be used in biocatalytic applications for preparing compounds not efficiently produced by other HHDH polypeptides.

In one aspect, engineered HHDH polypeptides comprise an amino acid sequence that differs at one or more residue positions from that of wild type *A. radiobacter* HheC or an engineered HHDH polypeptide of SEQ ID NO: 4 or SEQ ID NO: 244 to result in the altered or improved enzyme property, as further described below. In some embodiments, the recombinant HHDH polypeptides can comprise an amino acid sequence that is at least 60%, 65%, 70%, 71%, 72%, 73%, 74% 75%, 76%, 77%, 78%, 79%, 80%, 81%, 82%, 83%, 84%, 85% 86% 87%, 88%, 89%, 90%, 91%, 92%, 93%, 94%, 95%, 96%, 97%, 98%, 99% or more identical to the amino acid sequence of SEQ ID NO:4 or SEQ ID NO:244.

In some embodiments, the residue differences can be at one or more residue positions selected from X34; X51; X81; X85; X110; X131; X167; X232; X242; X248, and X254. In some embodiments, the residue differences for the engineered HHDH polypeptides can be selected from one or more of the following: X34 is G; X51 is P; X81 is E, F, M, W, or Y; X85 is V; X110 is S; X131 is A; X167 is H; X232 is S, X242 is A; X248 is V; and X254 is N. As will be understood by those skilled in the art, the indicated amino acids can be replaced by amino acids that are conservative substitutions to effect the changes to the desired enzyme property. In some embodiments, the recombinant HHDH polypeptides can have one or more residue differences at other residue positions. In some embodiment, the differences can be 1-2, 1-3, 1-4, 1-5, 1-6, 1-7, 1-8, 1-9, 1-10, 1-11, 1-12, 1-13, 1-14, 1-15, 1-16, 1-18, 1-20, 1-22, 1-24, 1-26, 1-28, 1-30, 1-32, 1-34, 1-36, 1-38, 1-40, 1-42, 1-44, 1-46, 1-48, or 1-50 residue differences at other residue positions as compared to SEQ ID NO: 4 or SEQ ID NO:244. In some embodiment, the differences can be 1, 2, 3, 4, 5, 6, 7, 8, 9, 10, 11, 12, 13, 14, 15, 16, 18, 20, 22, 24, 26, 28 30, 32, 34, 36, 38, 40, 42, 44, 46, 48, or 50 residue differences at other residue positions as compared to SEQ ID NO: 4 or SEQ ID NO:244. In some embodiments, the residue differences at other residue positions can comprise conservative mutations.

In some embodiments, the engineered HHDH polypeptides can comprise an amino acid sequence that is at least 60%, 65%, 70%, 71%, 72%, 73%, 74% 75%, 76%, 77%, 78%, 79%, 80%, 81%, 82%, 83%, 84%, 85% 86% 87%, 88%, 89%, 90%, 91%, 92%, 93%, 94%, 95%, 96%, 97%, 98%, 99% or more identical to the amino acid sequence of SEQ ID NO:4 or SEQ ID NO:244 and have one or more of the following residues: X12 is M, or S; X34 is G; X51 is P; X81 is E, F, M, W, or Y; X82 is C, G, K, L, M, N, or W; X83 is C or E; X84 is D; X85 is V; X86 is A or H; X110 is S, X131 is A; X134 is C, F, I, K, L, M, or V; X139 is G, I, L, M, P, S, T, or V; X142 is C, M or N; X146 is P; X167 is H; X175 is C, G, I, L, M, N, or V; X176 is F, M, Q, or T; X177 is L, S or T; X178 is T; X182 is S; X186 is H; X187 is G, I, or S; X201 is R; X232 is S, X242 is A; X243 is C or L; X245 is S; X246 is S; X247 is N; X248 is V; X249 is A, G, H, I, or S; X252 is C; and X254 is N. In some embodiments, the specified amino acid residues can be replaced with amino acids that are conservative substitutions of the specified amino acids. In some embodiments, the recombinant HHDH polypeptides can have one or more residue differences at other residue positions. In some embodiment, the differences can be 1-2, 1-3, 1-4, 1-5, 1-6, 1-7, 1-8, 1-9, 1-10, 1-11, 1-12, 1-13, 1-14, 1-15, 1-16, 1-18, 1-20, 1-22, 1-24, 1-26, 1-28, 1-30, 1-32, 1-34, 1-36, 1-38, 1-40, 1-42, 1-44, 1-46, 1-48, or 1-50 residue differences at other residue positions as compared to SEQ ID NO: 4 or SEQ ID NO:244. In some embodiment, the differences can be 1, 2, 3, 4, 5, 6, 7, 8, 9, 10, 11, 12, 13, 14, 15, 16, 18, 20, 22, 24, 26, 28, 30, 32, 34, 36, 38, 40, 42, 44, 46, 48, or 50 residue differences at other residue positions as compared to SEQ ID NO: 4 or SEQ ID NO:244. In some embodiments, the residue differences at other residue positions can comprise conservative mutations.

In some embodiments, the engineered HHDH polypeptides of the disclosure described above can be combined with residue differences at other residue positions to effect changes in the properties of the engineered HHDH polypeptide. In some embodiments, the residues can be based on the engineered enzymes described in US application publication US 2005/0153417, US application publication US2005/0272064, and US application publication US 2006/0099700, each of which is hereby incorporated herein by reference. In some embodiments, the amino acids that can be used in combination with the residues described above include, among others, one or more of the following: X2 is G; X4 is S, or V; X8 is K; X10 is L, N, or R; X12 is G, or Y; X20 is C; X21 is M; X30 is V; X38 is K, or L; X39 is G; X41 is A; X42 is A; X52 is K, or T; X54 is I, or V; X58 is G; X60 is T, or V; X63 is V; X67 is N; X68 is G; X69 is R, or V; X70 is F; X72 is Q, or R; X75 is I; X82 is F; X82 is I, S, T, V, or Y; X83 is A; X84 is L; X86 is F; X87 is Q; X91 is E, or R; X95 is A, or G; X99 is G, or N; X100 is A, or M; X107 is R; X112 is A; X113 is S; X116 is V; X117 is P, or T; X121 is D, E, or R; X124 is G; X128 is V; X129 is L; X134 is T; X135 is L, or S; X137 is W; X139 is D, H, K, N, R, or Y; X142 is G, or I; X146 is A, T, or V; X150 is V; X152 is T; X174 is G; X175 is S; X176 is D, E, H, R, S; X177 is A, F, G, N; X178 is C, M, V; X179 is D; X180 is T; X181 is E; X182 is N; X184 is K; X186 is W; X187 is H; X189 is T; X194 is I; X195 is N; X196 is L; X200 is T; X201 is W; X202 is L; X203 is K; X204 is R; X205 is Y; X215 is E, R; X222 is A; X223 is L; X230 is N; X238 is C, L, R, or T; X240 is T; X241 is A; X243 is S; X245 is A; X246 is V; X247 is D; X249 is R, Y, or * (sequence truncated after X248); X251 is A, or E; and X252 is I, N, or V.

In some embodiments, the HHDH polypeptides can have increased enantioselectivity for the S-alcohol product as compared to a reference HHDH polypeptide of SEQ ID NO: 244. In contrast, the reference HHDH polypeptide of SEQ ID NO: 244 displays R-enantioselectivity, similar to the wild-type HHDH HheC and the wild-type double-mutant engineered HHDH of SEQ ID NO: 4. In some embodiments, the engineered HHDH polypeptide is capable of converting a racemic styrene oxide to the corresponding S-alcohol in enantiomeric excess over the R-alcohol as shown below in Scheme 5.

Scheme 5

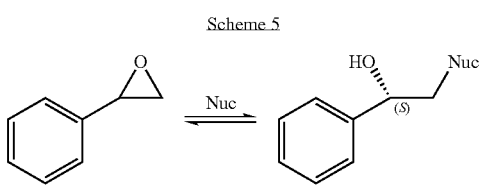

In some embodiments, the HHDH polypeptide is capable of converting racemic styrene oxide to S-azido alcohol in enantiomeric excess in the presence of the nucleophile $N_3$. In some embodiments, the HHDH polypeptide can convert racemic para-nitro-styrene-oxide (PNSO) to the corresponding S-alcohol in presence of a nucleophile.

In some embodiments, the engineered HHDH polypeptide having S-enantioselectivity for the reaction of Scheme 5 comprises an amino acid sequence having one or more of the following residues or groups of residues: X243 is L; X99 is N and X139 is M; X85 is V and X243 is S; X146 is P, X176 is S, and X243 is S; X139 is M and X243 is S; X139 is T, X176 is D, and X243 is S; X139 is T, X180 is T, and X243 is S; X139 is S and X243 is S; X80 is V and X139 is S; X95 is G and X139 is M and X243 is S; X121 is R and X176 is T and X243 is S; X62 is V and X139 is M and X197 is G; X112 is A and X139 is S; X139 is S or M; X139 is T and X201 is R; X85 is D and X139 is M and X 168 is V. Exemplary polypeptides with S-enantioselectivity include, but are not limited to, polypeptides comprising amino acid sequences corresponding to SEQ ID NO: 40, 120, 122, 130, 132, 136, 140, 144, 158, 162, 166, 274, 276, 286, 288, 290, 292, or 294.

In some embodiments, the engineered HHDH are capable of producing the S-alcohol in the reaction of Scheme 5 in at least about 20%, 40%, 60%, or 80% e.e. or more.

In some embodiments, the engineered HHDH capable of producing at least about 20% e.e. of the S-alcohol in the reaction of Scheme 5 comprises an amino acid sequence having one or more of the following residues or groups of residues: X80 is V and X139 is S; X95 is G, X139 is M and X243 is S; X243 is L; X121 is R, X176 is T and X243 is S; X139 is M and X243 is S; X62 is V, X139 is M and X197 is G; X112 is A and X139 is S; X139 is S; X139 is T and X201 is R; X139 is T, X176 is D, and X243 is S; X139 is T, X180 is T, and X243 is S; X146 is P, X176 is S, and X243 is S; X139 is S, and X243 is S; X99 is N and X139 is M; X85 is D, X139 is M and X168 is V; X85 is V and X243 is S; or X139 is M. Exemplary polypeptides capable of producing at least about 20% e.e. of the S-alcohol include, but are not limited to, polypeptides comprising amino acid sequences corresponding to SEQ ID NO: 120, 122, 140, 274, 288, 40, 162, 166, 276, 292, 294, 136, 158, 130, 132, 286, or 290.

In some embodiments, the engineered HHDH capable of producing at least about 40% e.e. of the S-alcohol in the reaction of Scheme 5 comprises an amino acid sequence having one or more of the following residues or groups of residues: X62 is V, X139 is M and X197 is G; X112 is A and X139 is S; X139 is S; X139 is T and X201 is R; X139 is T, X176 is D, and X243 is S; X139 is T, X180 is T, and X243 is S; X146 is P, X176 is S, and X243 is S; X139 is S, and X243 is S; X99 is N and X139 is M; X85 is D, X139 is M and X168 is V; X85 is V and X243 is S; or X139 is M. Exemplary polypeptides capable of producing at least about 40% e.e. of the S-alcohol include, but are not limited to, polypeptides comprising amino acid sequences corresponding to SEQ ID NO: 40, 162, 166, 276, 292, 294, 136, 158, 130, 132, 286, or 290.

In some embodiments, the engineered HHDH capable of producing at least about 60% e.e. of the S-alcohol in the reaction of Scheme 5 comprises an amino acid sequence having one or more of the following residues or groups of residues: X146 is P, X176 is S, and X243 is S; X139 is S, and X243 is S; X99 is N and X139 is M; X85 is D, X139 is M and X168 is V; X85 is V and X243 is S; or X139 is M. Exemplary polypeptides capable of producing at least about 60% e.e. of the S-alcohol include, but are not limited to, a polypeptide comprising an amino acid sequence corresponding to SEQ ID NO: 136, 158, 130, 132, 286, or 290.

In some embodiments, the engineered HHDH capable of producing at least about 80% e.e. of the S-alcohol in the reaction of Scheme 5 comprises an amino acid sequence having one or more of the following residues or groups of residues: X99 is N and X139 is M; X85 is D, X139 is M and X168 is V; X85 is V and X243 is S; or X139 is M. Exemplary polypeptides capable of producing at least about 80% e.e. of the S-alcohol include, but are not limited to, a polypeptide comprising amino acid sequence corresponding to SEQ ID NO: 130, 132, 286, or 290.

In some embodiments, the engineered HHDH polypeptide is capable of improved production of the R-alcohol in the reaction of Scheme 5 as compared to the HHDH polypeptide of SEQ ID NO: 244. In some embodiments, the engineered HHDH polypeptide is capable of producing at least about 40%, 60%, 80% or even higher % e.e. of the R-alcohol. In some embodiments, the engineered HHDH polypeptide with improved R-enantioselectivity comprises an amino acid sequence having one or more of the following residue differences or groups of residue differences as compared to SEQ ID NO: 244: N176T; N139S/N176T; E33G/W139T/N176S; G25C/W139M/N176T; N113S/W139T/N176S; N176S; W139M/I765/H201R/K204R; W139M/N176S; W139M/N176S/F243L; W139M/N176T; W139S/N176S; W139T/N176S; or T3S/W139M/N176S. Exemplary engineered HHDH polypeptides with this property include, but are not limited to, a polypeptide comprising an amino acid sequence corresponding to SEQ ID NO: 116, 142, 146, 148, 154, 156, 268, 270, 272, 278, 282, or 284.

In some embodiments, the engineered HHDH polypeptide is capable of converting racemic styrene oxide to the corresponding R-alcohol in greater enantiomeric excess over the S-alcohol than HHDH polypeptide of SEQ ID NO: 244. In some embodiments, the HHDH polypeptide can convert racemic para-nitro-styrene-oxide to R-para-nitro-hydroxy-halide in greater enantiomeric excess to the S-para-nitro-hydroxy-halide in greater enantiomeric excess than a halohydrin dehalogenase polypeptide of SEQ ID NO: 244.

In some embodiments, the engineered HHDH polypeptide is capable of producing at least about 40% e.e. of the R-alcohol comprises an amino acid sequence having one or more of the following residue differences or groups of residue differences: E33G/W139T/N176S; G25C/W139M/N176T; N113S/W139T/N176S; W139M/I765/H201R/K204R; W139M/N176S; W139M/N176S/F243L; W139M/N176T; W139S/N176S; W139T/N176S; or N176T; W139S/N176T. Exemplary polypeptides capable of producing at least about 40% e.e. of the R-alcohol include, but are not limited to, a polypeptide comprising amino acid sequence corresponding to SEQ ID NO: 116, 142, 146, 148, 154, 156, 270, 272, 278, 282, or 284.

In some embodiments, the engineered HHDH polypeptide capable of producing at least about 60% e.e. of the R-alcohol comprises an amino acid sequence having one or more of the following residues or groups of residues: E33G/W139T/N176S; G25C/W139M/N176T; N113S/W139T/N176S;

W139M/I765/H201R/K204R; W139M/N176S; W139M/N176S/F243L; W139M/N176T; W139S/N176S; or W139T/N176S. Exemplary polypeptides capable of producing at least about 60% e.e. of the R-alcohol include, but are not limited to, a polypeptide comprising amino acid sequence corresponding to SEQ ID NO: 116, 146, 148, 154, 156, 272, 278, 282, or 284.

In some embodiments, the engineered HHDH polypeptide capable of producing at least about 80% e.e. of the R-alcohol comprises an amino acid sequence having a serine at position 3, a methionine at position 139, and a serine at position 176. By way of example, a polypeptide capable of producing at least about 80% e.e. of the R-alcohol comprises the amino acid sequence of SEQ ID NO: 282.

In some embodiments, the engineered HHDH is capable of converting a racemic mixture of para nitro styrene haloalcohol (wherein X is F⁻, Cl⁻, Br⁻, or I⁻) to S-para-nitro-styrene-oxide as shown in Scheme 6.

Scheme 6

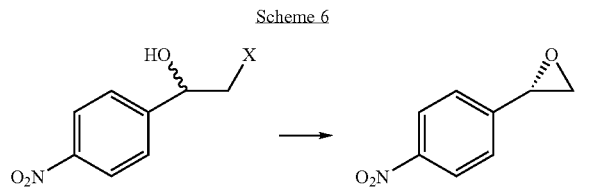

In some embodiments the engineered HHDH is capable of converting a racemic para nitro styrene haloalcohol to S-para-nitro-styrene-oxide comprises one or more residues or groups of residues selected from: X139 is T; X139 is T and X249 is H; X139 is S and X249 is V; X139 is M and X223 is V, and X249 is P. Exemplary polypeptides with this property include, but are not limited to, polypeptides comprising an amino acid sequence corresponding to SEQ ID NO:260, 262, 264, or 266.

In some embodiments, the engineered HHDH is capable of converting a racemic mixture of para nitro styrene haloalcohol to R-para-nitro-styrene-oxide, with improved R-enantioselectivity compared to the polypeptide of SEQ ID NO: 244. In some embodiments, the engineered HHDH capable of at least about 10-fold improved R-enantioselectivity and comprises one, or more residues or groups of residues selected from: X114 is V and X178 is C; X175 is G, L, M, or V; X175 is L and X222 is A. Exemplary polypeptides with this property include, but are not limited to, polypeptides comprising an amino acid sequence corresponding to SEQ ID NO: 44, 46, 48, 50, 86, 248, or 256. In some embodiments, the engineered HHDH capable of at least about 100-fold improved R-enantioselectivity and comprises one, or more residues or groups of residues selected from: X175 is G, L, M, or V; X175 is L and X222 is A. Exemplary polypeptides with this property include, but are not limited to, polypeptides comprising an amino acid sequence corresponding to SEQ ID NO: 44, 46, 48, 50, 86, or 248.

In some embodiments, the engineered HHDH polypeptide can have altered regioselectivity for the conversion of an epoxide substrate of formula (I) to an alcohol of formula (II) as compared to the wild-type HHDH HheC (accession: gi|15213643|gb|AAK92099.1|AF397296_1 halohydrin dehalogenase) or an engineered HHDH polypeptide of SEQ ID NO: 4 or 244. As discussed above, wild-type HheC and the engineered polypeptide of SEQ ID NO: 4 are regioselective for the β-carbon on the substituted epoxide ring. The polypeptide of SEQ ID NO: 244 is about 1 to 2-fold more regioselective for the α-carbon. In the embodiments herein, the engineered HHDH polypeptides can have increased regioselectivity for the β-carbon or increased regioselectivity for the α-carbon as compared to the reference HHDH polypeptides of SEQ ID NO: 4 or SEQ ID NO: 244.

In some embodiments, the engineered HHDH polypeptides of the disclosure have greater α-regioselectivity than a halohydrin dehalogenase polypeptide of SEQ ID NO: 244 or SEQ ID NO: 4. In some embodiments, the HHDH polypeptide is capable of at least about 2, 3, 4, 5, 6, or 7-fold more α than β regioselectivity (having a ratio of α:β>1) in the ring opening of epoxide substrates, wherein the ratio of α to β represents the increased frequency of nucleophilic attack at the α position versus the β position.

In some embodiments, the engineered HHDH is capable of converting styrene oxide to the S-alcohol in a α-attack and is enantioselective for the S-enantiomer in the reaction of Scheme 7 below.

Scheme 7

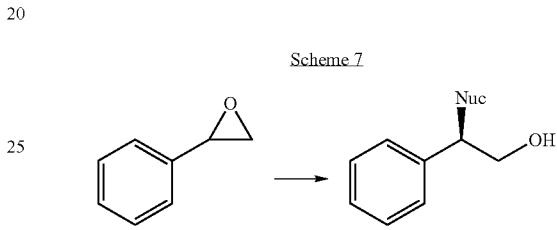

Residue differences (as compared to SEQ ID NO: 244) associated with increased α-attack and enantioselectivity for the S-enantiomer in the reaction of Scheme 7 include: W139L or W139M.

In some embodiments, the engineered HHDH is capable of converting styrene oxide to the R-alcohol in an α-attack and is enantioselective for the R-enantiomer in the reaction of Scheme 8 below.

Scheme 8

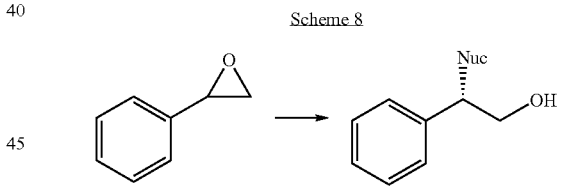

Residue differences (as compared to SEQ ID NO: 244) associated with increased α-attack and enantioselectivity for the R-enantiomer include the combination of: W139L and P175L. A skilled artisan can determine the residue differences or residue difference combinations resulting in S or R enantiomer from an α-attack using the guidance provided in the present disclosure.

In some embodiments, the engineered HHDH polypeptide is capable of at least about 3-fold more α than β regioselectivity as compared to the engineered HHDH polypeptide of SEQ ID NO: 244 and comprises an amino acid sequence having one or more of the residue differences or groups of residue differences (as compared to SEQ ID NO: 244) selected from: W139M; D99N/W139M; E85D/W139M/I168V; L62V/W139M/E197G; W139S; V112A/W139S; or D80V/W139S. Exemplary polypeptides with this property include, but are not limited to, polypeptides comprising amino acid sequences corresponding to SEQ ID NO: 40, 132, 274, 276, 286, 290, or 294.

In one embodiment, the engineered HHDH polypeptide is capable of at least about 6-fold more α than β regioselectivity as compared to the engineered HHDH polypeptide of SEQ ID NO:244 and comprises an amino acid sequence of SEQ ID NO: 132 wherein the residue at position X99 is N and the residue at position X139 is M.

In one embodiment, the engineered HHDH polypeptide is capable of at least about 7-fold more α than β regioselectivity as compared to the engineered HHDH polypeptide of SEQ ID NO:244 and comprises an amino acid sequence of SEQ ID NO:286 wherein the residue at position X139 is M.

In some embodiments, the engineered HHDH polypeptide can mediate styrene oxide ring opening by nucleophilic α-attack of azide. In these embodiments, the HHDH polypeptide can comprise an amino acid sequence having one or more of the following residues: W139L, W139M, P175L, N176D, W139S, W139M/F243S, or F243L. Exemplary polypeptides with this property include, but are not limited to, polypeptides comprising amino acid sequences corresponding to SEQ ID NO: 34, 40, or 122.

In one embodiment, the engineered HHDH polypeptide comprises an amino acid sequence of SEQ ID NO: 4 or 244 in which the residue at position 139 is substituted with a methionine, and having more than 7-fold more α-attack than β-attack.

In some embodiments, the engineered HHDH polypeptide has increased β-selectivity for the conversion of the epoxide of formula (I) to the alcohol of formula (II) than the HHDH polypeptide of SEQ ID NO:244.

In some embodiments, the engineered HHDH is capable of converting styrene oxide to the S alcohol in a β attack and enantioselective for the R-enantiomer in the reaction of Scheme 9 below.

Scheme 9

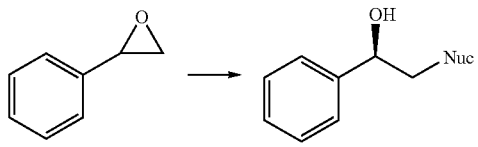

Residue differences (as compared to SEQ ID NO: 244) associated with increased β attack and enantioselectivity for the R-enantiomer include N176S.

In some embodiments, the engineered HHDH is capable of converting styrene oxide to the S alcohol in a β attack and enantioselective for the S-enantiomer in the reaction of Scheme 10 below.

Scheme 10

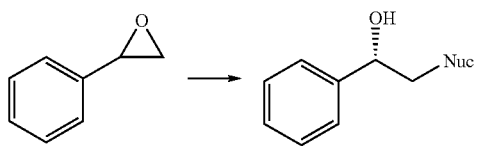

Residue differences (as compared to SEQ ID NO: 244) associated with increased β attack and enantioselectivity for the R-enantiomer include F243S. A skilled artisan can determine the residue or residue combinations resulting in S or R enantiomer from a beta attack using the guidance in the present disclosure.

In some embodiments, the engineered HHDH polypeptide is capable of at least about 2-fold more β than α regioselectivity as compared to the engineered HHDH polypeptide of SEQ ID NO:244, and comprises an amino acid sequence having one or more residue differences or groups of residue differences selected from: X3 is S, X139 is M, and X176 is S; X25 is C, X139 is M, and X176 is T; X113 is S, X139 is T, X176 is S; X139 is S, X176 is S; X139 is M, X176 is S, and X243 is L; X139 is M, X176 is S, X201 is R, and X204 is R; X139 is T, X176 is D, and X243 is S; X139 is M, and X176 is D; X139 is T, X180 is T, and X243 is S; X139 is M, and X176 is S; X139 is S, and X176 is T; X139 is T, and X176 is D; and X139 is T, and X176 is S. Exemplary engineered HHDH polypeptides with increased b selectivity can comprise an amino acid sequence corresponding to SEQ ID NO: 116, 146, 154, 156, 162, 164, 166, 268, 270, 272, 280, 282, or 284.

In some embodiments, the engineered HHDH polypeptide is capable of at least about 3-fold more β than α regioselectivity than a halohydrin dehalogenase polypeptide of SEQ ID NO:244, and comprises an amino acid sequence having one or more residues selected from the following: W139M/N176S/F243L; or W139M/N176D. Exemplary engineered HHDH polypeptides with increased b selectivity can comprise an amino acid sequence corresponding to SEQ ID NO: 154 or 164.

As discussed above, the wild-type HHDH HheC and engineered HheC double-mutant of SEQ ID NO: 4 is limited to ring opening of terminal epoxide substrates or ring closure of haloalcohols to the terminal epoxides. For example, Majeric-Elenkov et al., 2006, Adv. Synth. Catal. 348, 579-585 shows that HheA, HheB, and HheC did not show detectable activity on cyclohexene oxide and 2,3 epoxybutane. In one aspect, the present invention provides engineered HHDH polypeptides having measurable and increased rate for converting a non-terminal epoxide to the corresponding alcohol product as compared to a reference HHDH polypeptide having the amino acid sequence of SEQ ID NO:4 and SEQ ID NO:244.

In some embodiments, the engineered HHDH polypeptide (as compared to a reference HHDH polypeptide of SEQ ID NO:244) is capable of increased rate of converting 2-chloro-cyclohexanol to cyclohexene oxide, as shown in Scheme 11.

Scheme 11

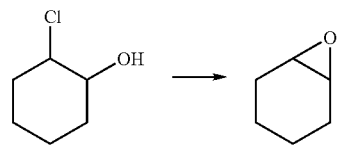

In some embodiments, the present disclosure provides an engineered HHDH polypeptide that is capable of at least 1.5-fold more activity than the polypeptide of SEQ ID NO:244 in the conversion of 2-chloro-cyclohexanol to cyclohexene oxide (Scheme 11). In some embodiments, the recombinant HHDH comprises an amino acid sequence having one or more residue differences (as compared to SEQ ID NO: 244) selected from: X84 is L, I, M, or F; X134 is T or V; X134 is T, X142 is L, and X245 is V. Exemplary polypeptides with this property include, but are not limited to, polypeptides comprising amino acid sequences corresponding to SEQ ID NO: 62, 220, 228, 250, 298, 302, or 304.

In some embodiments, the engineered HHDH are capable of converting a non-terminal epoxide of cis or trans 2,3-epoxybutane that is improved over the reference polypeptide of SEQ ID NO:244. In some embodiments, in the conversion of cis 2,3 epoxybutane, the improvement in activity are associated with the following residue differences or groups of residue differences (as compared to SEQ ID NO: 244): N176M; R20C/W86H/G137W; A134V; A134L; N176H; Y187I; V84I; 163V/N176F; L142C; A82F; F12M/T67I; A82Y; W86F; A82L; F12M; L142M; A134C; and D182S. Exemplary engineered HHDH polypeptides with this improved activity comprise an amino acid sequence corresponding to SEQ ID NO: 30, 64, 66, 68, 178, 182, 186, 210, 212, 214, 220, 226, 228, 238, 242, or 246. In some embodiments, the engineered HHDH has at least 1.5-fold greater activity on cis 2,3 epoxybutane as compared to SEQ ID NO:244 and comprises an amino acid sequence corresponding to the sequence of SEQ ID NO: 64, 68, 220, 226, or 228.

In some embodiments, wherein the non-terminal epoxide is trans-2,3-epoxybutane, the improvements in activity are associated with the following residue differences or groups of residue differences (as compared to SEQ ID NO: 244): A134V; R20C/W86H/G137W; A134L; V84I; W86F; Y187I; L142M; A82Y; A82W; A82F; A134C; L178V; L142C; A82M; L178M; L178V; A82L; F12M; N176M; L142G; A82S; A82K; A82I; 181L; Y186F; A134F; A82N; A82G; A82T; N176H; V84C; L142I; A134M; and P175C. Exemplary engineered HHDH polypeptides having this activity comprise an amino acid sequence corresponding to SEQ ID NO: 30, 58, 64, 68, 96, 178, 182, 184, 186, 202, 204, 206, 210, 212, 214, 216, 218, 220, 226, 228, 230, 232, 234, 236, 238, 242, or 254.

In some embodiments, the engineered HHDH has at least 1.5 fold greater activity on trans 2,3 epoxybutane as compared to SEQ ID NO:244 and comprises an amino acid sequence corresponding to the sequence of SEQ ID NO: 96, 178, 186, 206, 210, 212, 214, 218, 220, 226, 228, 242, or 254.

In some embodiments, the engineered HHDH has at least 3 fold greater activity on trans 2,3 epoxybutane as compared to SEQ ID NO:244 and comprises an amino acid sequence of SEQ ID NO:212 or 226.

In some embodiments, the engineered HHDH has at least 10 fold greater activity on trans 2,3 epoxybutane as compared to SEQ ID NO:244 and comprises an amino acid sequence of SEQ ID NO:228.

Further provided herein are engineered HHDH polypeptides that have increased refractoriness to inhibition by a halide ion as compared to a reference HHDH polypeptide of SEQ ID NO:4 or SEQ ID NO:244. In some embodiments, the halide ion is selected from Br$^-$, Cl$^-$, or I. In some embodiments, the HHDH polypeptides have at least about 1.5-fold, 2-fold, 5-fold, or at least about 10-fold increase in refractoriness to inhibition by halide ions than SEQ ID NO: 244. In some embodiments, the engineered HHDH polypeptides having increased refractoriness to inhibition by halide ions can comprise an amino acid sequence with one or more of the following residue differences (as compared to SEQ ID NO: 244): X114 is V, and X178 is C; X167 is H, and X178 is V; X139 is M, X176 is D, and X243 is S; X139S and X249V; X187 is S; X178 is V; X12 is Y or G; X139 is M, X176 is T, X223 is L, and X243 is L; X139 is M and X176 is S; or X139 is M and X176 is T. Exemplary polypeptides with having increased refractoriness to inhibition by halide ions include, but are not limited to, a polypeptide comprising an amino acid sequence corresponding to SEQ ID NO: 28, 90, 94, 114, 118, 148, 172, 254, 256, 260, or 268.

In some embodiments the recombinant HHDH has at least a 5-fold increase in $K_i$ for halide ion as compared to the $K_i$ for SEQ ID NO: 4 or SEQ ID NO: 244. In some embodiments, the recombinant HHDH polypeptides have a $K_i$ for chloride of at least about 10 mM. In some embodiments, the recombinant HHDH polypeptides are capable of maintaining a higher rate of catalysis of haloalcohol ring closure and ring opening of epoxides in the presence of 100 mM chloride as compared to the polypeptide of SEQ ID NO: 4 or SEQ ID NO: 244.

In some embodiments, the present disclosure provides engineered HHDH polypeptides capable of using formate as a nucleophile in catalyzing the enantioselective ring opening reaction of an α,α-disubstituted styrene oxide of compound of formula (X) as shown below in Scheme 12.

Scheme 12

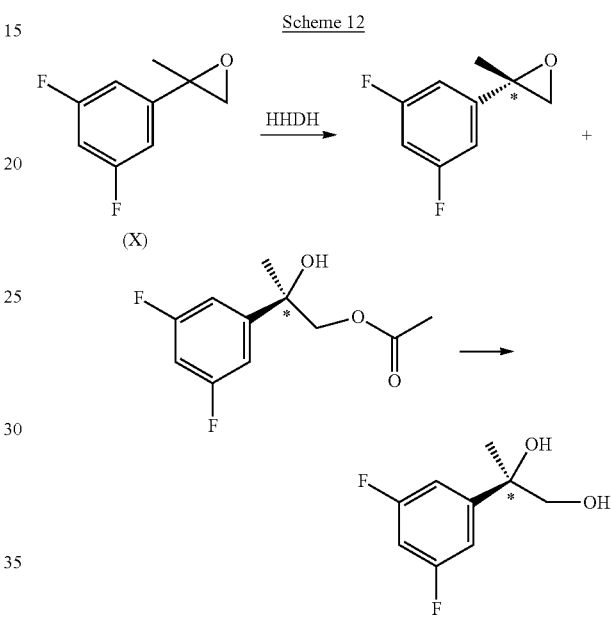

In some embodiments, the engineered HHDH polypeptides capable of catalyzing enantioselective ring opening using formate as in Scheme 12 have amino acid sequences comprising at least the following residue differences (as compared to SEQ ID NO: 244): X81E, M, or W; X82C, or S; X84I; X134I; X142G, or N; and X176D. In some embodiments, the engineered HHDH polypeptide capable of catalyzing enantioselective ring opening using formate as in Scheme 12 comprise an amino acid sequence of any one of SEQ ID NO: 176, 184, 194, 196, 198, 220, 222, 230, or 240.

In some embodiments, the engineered HHDH polypeptides has an increased rate for converting the epoxide substrate of formula (I) to the alcohol product of formula (II), infra, as compared to the HHDH polypeptide of SEQ ID NO:244. In some embodiments, the epoxide substrate of formula (I) is selected from: styrene oxide (1a); para-nitrostyrene oxide (1b); benzylethylene oxide (1c); 1,2-epoxybutane (2a); and 1,2 epoxyhexane (2b) (as illustrated in the structures below).

(1a)

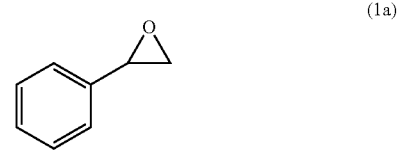

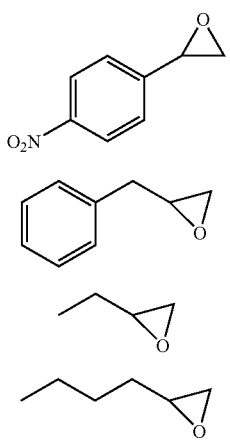

Table 2 below provides a list of exemplary engineered HHDH polypeptides and corresponding polynucleotides with the altered or improved enzyme properties described herein. The odd numbered SEQ IDs refer to the polynucleotide sequences while the even numbered SEQ ID NOs refer to the amino acid sequences. The column listing the residue differences (i.e., mutations) is with respect to the engineered HHDH of SEQ ID NO: 244, unless indicated otherwise. The amino acid sequence of SEQ ID NO: 4 is the wild-type sequence HheC of *A. radiobacter* (accession: >gi|15213643|gb|AAK92099.1|AF397296_1 halohydrin dehalogenase) with two amino acid residue changes: C153S and W249F (relative to wild-type HheC as reference).

TABLE 2

| SEQ ID NO: (nt/aa) | Residue Differences (relative to SEQ ID NO: 244) |
|---|---|
| 1/2 | L142I; V245A |
| 3/4 | H37Q, Q38K, I52K, L70Y, H72Q, A82F, P83A, V84P, W86F, R87Q, D99G, T100A, K107R, A134T, S146T, A154T, A174G, E181E, Y186F, S189T, S195N, R203K, T222A, V245M, W249F |
| 5/6 | W249H |
| 7/8 | D39G, A60T, S68G, H72Q, A110S, T222A, A240T |
| 9/10 | K10R, A60T, P83A, K215R, T222A, W249R |
| 11/12 | G137W, M252I |
| 13/14 | L178V, W238L |
| 15/16 | V75I, W238L |
| 17/18 | K91R, S189T, P196L, A240T |
| 19/20 | A4S, K91R, S189T, P196L, K215E, A240T |
| 21/22 | H72Q, A240T |
| 23/24 | H72R, W139Y, W249R |
| 25/26 | F12S, A69V, A116V |
| 27/28 | F12G |
| 29/30 | F12M |
| 31/32 | W139I |
| 33/34 | W139L |
| 35/36 | W139V |
| 37/38 | S2G, W139T |
| 39/40 | W139S |
| 41/42 | W139N |
| 43/44 | P175M |
| 45/46 | P175L |
| 47/48 | P175V |
| 49/50 | P175G |
| 51/52 | P175I |
| 53/54 | A134T, P175L |
| 55/56 | P175S |
| 57/58 | P175C |
| 59/60 | P175N |
| 61/62 | A134T |

TABLE 2-continued

| SEQ ID NO: (nt/aa) | Residue Differences (relative to SEQ ID NO: 244) |
|---|---|
| 63/64 | N176H |
| 65/66 | I63V, N176F |
| 67/68 | N176M |
| 69/70 | N176Q |
| 71/72 | Y177S |
| 73/74 | K10N |
| 75/76 | K10R, Y177N |
| 77/78 | Y177T |
| 79/80 | Y177L |
| 81/82 | A82T |
| 83/84 | S34G |
| 85/86 | I128V, L178C |
| 87/88 | L178T |
| 89/90 | N167H, L178V |
| 91/92 | Y187G |
| 93/94 | Y187S |
| 95/96 | Y187I |
| 97/98 | Y187H |
| 99/100 | W139I, W249G |
| 101/102 | W139L, A150V, W249I |
| 103/104 | W139L, W249* (sequence truncated at X248) |
| 105/106 | W139P, W249A |
| 107/108 | W139G, W249S |
| 109/110 | Y186H |
| 111/112 | D182S |
| 113/114 | F12Y |
| 115/116 | N113S, W139T, N176S |
| 117/118 | W139M, N176T, F223L, F243L |
| 119/120 | F243L |
| 121/122 | W139M, F243S |
| 123/124 | N176S, F243L |
| 125/126 | W139T, F243L |
| 127/128 | W139S, N176D |
| 129/130 | E85V, F243S |
| 131/132 | D99N, W139M |
| 133/134 | T131A, W139T, N176D |
| 135/136 | W139S, F243S |
| 137/138 | W139T, N176S, F243S |
| 139/140 | K121R, N176T, F243S |
| 141/142 | N176T |
| 143/144 | W139S, N176S, F243S |
| 145/146 | W139S, N176S |
| 147/148 | W139M, N176T |
| 149/150 | L51P, W139M, N176T, A200T, F243S |
| 151/152 | K91E, N176S, L232S |
| 153/154 | W139M, N176S, F243L |
| 155/156 | W139M, N176S, H201R, K204R |
| 157/158 | S146P, N176S, F243S |
| 159/160 | N176D, F243S |
| 161/162 | W139T, N176D, F243S |
| 163/164 | W139M, N176D |
| 165/166 | W139T, S180T, F243S |
| 167/168 | W139S, N176D, F243S |
| 169/170 | W139M, N176D, Y186H, F243L |
| 171/172 | W139M, N176D, F243S |
| 173/174 | I81F |
| 175/176 | A82C |
| 177/178 | A82F |
| 179/180 | A82G |
| 181/182 | A82L |
| 183/184 | A82S |
| 185/186 | A82Y |
| 187/188 | P83C |
| 189/190 | P83E |
| 191/192 | W86A |
| 193/194 | I81E |
| 195/196 | I81M |
| 197/198 | I81W |
| 199/200 | I81Y |
| 201/202 | A82I |
| 203/204 | A82K |
| 205/206 | A82M |
| 207/208 | V84D |
| 209/210 | W86F |
| 211/212 | R20C, W86H, G137W |
| 213/214 | A134C |

TABLE 2-continued

| SEQ ID NO: (nt/aa) | Residue Differences (relative to SEQ ID NO: 244) |
|---|---|
| 215/216 | A82N |
| 217/218 | A82W |
| 219/220 | V84I |
| 221/222 | A134I |
| 223/224 | A134K |
| 225/226 | A134L |
| 227/228 | A134V |
| 229/230 | L142G |
| 231/232 | A134F |
| 233/234 | A134M |
| 235/236 | L142I |
| 237/238 | L142M |
| 239/240 | L142N |
| 241/242 | L142C |
| 243/244 | N/A |
| 245/246 | F12M; T67I; |
| 247/248 | P175L; T222A; |
| 249/250 | A134T |
| 251/252 | L178C; |
| 253/254 | L178V |
| 255/256 | A114V; L178C; |
| 257/258 | Y186F |
| 259/260 | W139S; W249V; |
| 261/262 | W139T; W249H; |
| 263/264 | W139M; F223V; W249P; |
| 265/266 | W139T; |
| 267/268 | W139M; N176S; |
| 269/270 | W139S; N176T; |
| 271/272 | G25C; W139M; N176T; |
| 273/274 | D80V; W139S; |
| 275/276 | L62V; W139M; E197G; |
| 277/278 | E33G; W139T; N176S; |
| 279/280 | W139T; N176D; |
| 281/282 | T3S; W139M; N176S; |
| 283/284 | W139T; N176S; |
| 285/286 | W139M; |
| 287/288 | E95G; W139M; F243S; |
| 289/290 | E85D; W139M; I168V; |
| 291/292 | W139T; H201R; |
| 293/294 | V112A; W139S; |
| 295/296 | V84C |
| 297/298 | V84F; |
| 299/300 | I81L |
| 301/302 | V84L; |
| 303/304 | V84M; |

In some embodiments, the engineered HHDH polypeptides comprise an amino acid sequence that is at least about 60%, 65%, 70%, 71%, 72%, 73%, 74% 75%, 76%, 77%, 78%, 79%, 80%, 81%, 82%, 83%, 84%, 85% 86% 87%, 88%, 89%, 90%, 91%, 92%, 93%, 94%, 95%, 96%, 97%, 98%, 99% or more identical to a reference sequence based on SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, and 304 with the proviso that the engineered HHDH amino acid sequence has at least any one of the set of the specified residue differences (i.e., mutations) contained in any one of the polypeptide sequences listed in Table 2. In some embodiments, the HHDH polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35, 1-40, 1-45, or 1-50 residue differences at other amino acid residue positions as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35, 40, 45, or 50 residue differences at other amino acid residues. In some embodiments, the differences comprise conservative mutations.

As noted above, the halohydrin dehalogenases of the disclosure can be described in reference to the amino acid sequence of a naturally occurring HHDH HheC of *A. radiobacter*, the engineered HheC double-mutant (SEQ ID NO: 4), or another engineered HHDH (e.g., SEQ ID NO: 244). As such, the amino acid residue position is determined in the halohydrin dehalogenases beginning from the initiating methionine (M) residue (i.e., M represents residue position 1), although it will be understood by the skilled artisan that this initiating methionine residue may be removed by biological processing machinery, such as in a host cell or in vitro translation system, to generate a mature protein lacking the initiating methionine residue. The amino acid residue position at which a particular amino acid or amino acid change is present in an amino acid sequence is sometimes describe herein in terms "Xn", or "position n", where n refers to the residue position. Furthermore, the halohydrin dehalogenases of the disclosure may be described relative to a reference polypeptide sequence. For example, one reference sequence is that of an engineered double-mutant of *A. radiobacter* HheC which comprises the amino acid sequence of SEQ ID NO: 4. Another reference sequence is that of SEQ ID NO: 244 which is the amino acid sequence of SEQ ID NO:730 disclosed in U.S. Ser. No. 11/266,747, published as US 2006/0099700 A1, which is hereby incorporated by reference in its entirety.

As described in the foregoing, the halohydrin dehalogenase polypeptides herein can have a number of modifications to the reference sequence (e.g., naturally occurring polypeptide or an engineered polypeptide) to result in the improved halohydrin dehalogenase property. As used herein, "modifications" include amino acid substitutions, deletions, and insertions. Any one or a combination of modifications can be introduced into the naturally occurring or engineered polypeptide to generate engineered enzymes. In such embodiments, the number of modifications to the amino acid sequence can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 15% of the total number of amino acids, up to 20% of the total number of amino acids, or up to 30% of the total number of amino acids of the reference polypeptide sequence. In some embodiments, the number of modifications to the naturally occurring polypeptide or an engineered polypeptide that produces an improved halohydrin dehalogenase property may comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 modifications of the reference sequence. In some embodiments, the number of modifications can be 1, 2, 3, 4, 5, 6, 7, 8, 9, 10, 11, 12, 14, 15, 16, 18, 20, 22, 24, 26, 30, 35 or about 40 amino acid residues. The modifications can comprise insertions, deletions, substitutions, or combinations thereof.

In some embodiments, the modifications comprise amino acid substitutions to the reference sequence. Substitutions that can produce an improved halohydrin dehalogenase property may be at one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 15% of the total number of amino acids, up to 20% of the total number of amino acids, or up to 30% of the total number of amino acids of the reference enzyme sequence. In some embodiments, the number of substitutions to the naturally occurring polypeptide or an engineered polypeptide that produces an improved halohydrin dehalogenase property can comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 amino acid substitutions of the reference sequence. In some embodiments, the number of substitutions can be 1, 2, 3, 4, 5, 6, 7, 8, 9, 10, 11, 12, 14, 15, 16, 18, 20, 22, 24, 26, 30, 35 or about 40 amino acid residues.

As will be appreciated by those of skill in the art, some of the above-defined categories of amino acid residues, unless otherwise specified, are not mutually exclusive. Thus, amino acids having side chains exhibiting two or more physicochemical properties can be included in multiple categories. The appropriate classification of any amino acid or residue will be apparent to those of skill in the art, especially in light of the detailed disclosure provided herein.

In some embodiments, the improved engineered halohydrin dehalogenase enzymes comprise deletions of the naturally occurring halohydrin dehalogenase polypeptides or deletions of other engineered halohydrin dehalogenase polypeptides. In some embodiments, each of the improved engineered halohydrin dehalogenase enzymes described herein can comprise deletions of the polypeptides described herein. Thus, for each and every embodiment of the halohydrin dehalogenase polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 15% of the total number of amino acids, up to 20% of the total number of amino acids, or up to 30% of the total number of amino acids of the halohydrin dehalogenase polypeptides, as long as the functional activity of the halohydrin dehalogenase activity is maintained. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 amino acid residues. In some embodiments, the number of deletions can be 1, 2, 3, 4, 5, 6, 7, 8, 9, 10, 11, 12, 14, 15, 16, 18, 20, 22, 24, 26, 30, 35 or about 40 amino acids. In some embodiments, the deletions can comprise deletions of 1, 2, 3, 4, 5, 6, 7, 8, 9, 10, 11, 12, 13, 14, 15, 16, 18, or 20 amino acid residues.

In some embodiments, the present disclosure provides an engineered HHDH polypeptide having a C-terminal 6 amino deletion relative to the reference polypeptides of SEQ ID NO: 4 or 244. In such an embodiment, the resulting engineered HHDH polypeptide is only 248 amino acid residues (rather than 254) in length. Accordingly, in some embodiments, the present disclosure provides engineered HHDH polypeptides with improved enzyme properties relative to reference polypeptides of SEQ ID NO: 4 or 244, wherein the amino acid sequence consists of an amino acid sequence from position X1 to X248, or from position X2 to X248, of any one of any one of the polypeptides of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, and 304. In one embodiment, the C-terminal truncated engineered HHDH polypeptide comprises the amino acid sequence of SEQ ID NO: 104.

As described herein, the engineered HHDH polypeptides of the disclosure can be in the form of fusion polypeptides in which the halohydrin dehalogenase polypeptides are fused to other polypeptides, such as, by way of example and not limitation, antibody tags (e.g., myc epitope), purifications sequences (e.g., His tags), and cell localization signals (e.g., secretion signals). Thus, the halohydrin dehalogenase polypeptides can be used with or without fusions to other polypeptides.

Accordingly, in some embodiments, the engineered HHDH polypeptides can further comprises a fusion at the carboxy terminus of a contiguous segment of about 1 to about 20 amino acid residues to a polypeptide of any one of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, and 304. In some embodiments, any of the engineered HHDH polypeptides can be modified with a one residue extension at position X254 of an asparagine residue (N). Thus, in some embodiments, any of the engineered HHDH polypeptides sequences disclosed herein may comprise at least a position X255 having a N residue (i.e., X255N). It has been observed that an engineered HHDH polypeptide comprising the amino acid sequence of SEQ ID NO: 126 can be modified with a C-terminal asparagine (X255N) and is capable of improved enzyme properties of increased activity and enantioselectivity relative to SEQ ID NO: 244. It is contemplated that this or other C-terminal fusions to the disclosed engineered polypeptides can result in similarly improved properties.

The polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminomethylphenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses, but are not limited to: Arg(tos), Cys (methylbenzyl), Cys (nitropyridinesulfenyl), Glu(δ-benzylester), Gln(xanthyl), Asn(N-δ-xanthyl), His(bom), His(benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

As described above the various modifications introduced into the naturally occurring polypeptide to generate an engineered halohydrin dehalogenase enzyme can be targeted to a specific property of the enzyme.

1.4 Polynucleotides Encoding Engineered Halohydrin Dehalogenases

In another aspect, the present disclosure provides polynucleotides encoding the engineered halohydrin dehalogenase enzymes. The polynucleotides may be operatively linked to one or more heterologous regulatory sequences that control gene expression to create a recombinant polynucleotide capable of expressing the polypeptide. Expression constructs containing a heterologous polynucleotide encoding the engineered halohydrin dehalogenase can be introduced into appropriate host cells to express the corresponding halohydrin dehalogenase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved halohydrin dehalogenase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Table 2 and the accompanying Sequence Listing.

In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells.

In certain embodiments, all codons need not be replaced to optimize the codon usage of the halohydrin dehalogenases since the natural sequence will comprise preferred codons and because use of preferred codons may not be required for all amino acid residues. Consequently, codon optimized polynucleotides encoding the halohydrin dehalogenase enzymes may contain preferred codons at about 40%, 50%, 60%, 70%, 80%, or greater than 90% of codon positions of the full length coding region.

In some embodiments, the polynucleotide comprises a nucleotide sequence encoding a halohydrin dehalogenase polypeptide with an amino acid sequence that has at least about 60%, 65%, 70%, 71%, 72%, 73%, 74% 75%, 76%, 77%, 78%, 79%, 80%, 81%, 82%, 83%, 84%, 85% 86% 87%, 88%, 89%, 90%, 91%, 92%, 93%, 94%, 95%, 96%, 97%, 98%, 99% or more sequence identity to a reference engineered halohydrin dehalogenase polypeptides described herein. Accordingly, in some embodiments, the polynucleotide encodes an amino acid sequence that is at least about 80%, 85%, 86%, 87%, 88%, 89%, 90%, 91%, 92%, 93%, 94%, 95%, 96%, 97%, 98%, 99% or more identical to the sequence of SEQ ID NO: 244 and differs from SEQ ID NO244 at one or more residue positions selected from: X34; X51; X81; X85; X110; X131; X167; X232; X242; X248, and X254. In some embodiments, the polynucleotide encodes an amino acid sequence corresponding to SEQ ID NO: 2, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, and 304.

In some embodiments, the polynucleotide comprises a nucleotide sequence encoding a halohydrin dehalogenase polypeptide with an amino acid sequence that has at least about 60%, 65%, 70%, 71%, 72%, 73%, 74% 75%, 76%, 77%, 78%, 79%, 80%, 81%, 82%, 83%, 84%, 85% 86% 87%, 88%, 89%, 90%, 91%, 92%, 93%, 94%, 95%, 96%, 97%, 98%, 99% or more sequence identity to the polypeptide comprising an amino acid corresponding to SEQ ID NO: 2, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, and 304.

In some embodiments, the polynucleotides encoding the halohydrin dehalogenases are selected from SEQ ID NO: 1, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, and 303.

In some embodiments, the polynucleotides are capable of hybridizing under highly stringent conditions to a polynucleotide comprising SEQ ID NO: 1, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, and 303, where the highly stringently hybridizing polynucleotides encode a halohydrin dehalogenase capable of stereoselectively converting the substrate of formula (I) to the product of formula (II), or stereoselectively converting the substrate of formula (I) to the product of formula (III), or stereoselectively converting a substrate of formula (IV) to the product of formula (V).

In some embodiments, the polynucleotides encode the polypeptides described herein but have about 80% or more sequence identity, about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered halohydrin dehalogenase. In some embodiments, the reference polynucleotide is selected from SEQ ID NO: 1, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, and 303.

An isolated polynucleotide encoding an improved halohydrin dehalogenase polypeptide may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3$^{rd}$ Ed., Cold Spring Harbor Laboratory Press; and Current Protocols in Molecular Biology, Ausubel. F. ed., Greene Pub. Associates, 1998, updates to 2006.

For bacterial host cells, suitable promoters for directing transcription of the nucleic acid constructs of the present disclosure, include the promoters obtained from the *E. coli* lac operon, *E. coli* trp operon, bacteriophage λ, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25). Further promoters are described in "Useful proteins from recombinant bacteria" in Scientific American, 1980, 242:74-94; and in Sambrook et al., supra.

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* those phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, Mol Cell Bio 15:5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NC1B 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiol Rev 57: 109-137.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the HHDH polypeptide of the present invention would be operably linked with the regulatory sequence.

Thus, in another embodiment, the present disclosure is also directed to a recombinant expression vector comprising a polynucleotide encoding an engineered halohydrin dehalogenase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

The expression vectors of the present invention preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori (as shown in the plasmid of FIG. 5) or the origins of replication of plasmids pBR322, pUC19, pACYC177 (which plasmid has the P15A ori), or pACYC184 permitting replication in *E. coli*, and pUB110, pE194, pTA1060, or pAMλ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (see, e.g., Ehrlich, 1978, Proc Natl Acad. Sci. USA 75:1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present invention are commercially available. Suitable commercial expression vectors include p3×FLAG™™ expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptII SK(−) and pBK-CMV, which are commercially available from Stratagene, LaJolla Calif., and plasmids which are derived from pBR322 (Gibco BRL), pUC (Gibco BRL), pREP4, pCEP4 (Invitrogen) or pPoly (Lathe et al., 1987, Gene 57:193-201).

1.5 Host Cells for Expression of Halohydrin Dehalogenase Polypeptides

In another aspect, the present disclosure provides a host cell comprising a polynucleotide encoding an improved halohydrin dehalogenase polypeptide of the present disclosure, the polynucleotide being operatively linked to one or more control sequences for expression of the halohydrin dehalogenase enzyme in the host cell. Host cells for use in expressing the HHDH polypeptides encoded by the expression vectors of the present invention are well known in the art and include but are not limited to, bacterial cells, such as *E. coli, Lactobacillus kefir, Lactobacillus brevis, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the halohydrin dehalogenase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

An exemplary host cell is *Escherichia coli* W3110. The expression vector was created by operatively linking a polynucleotide encoding an improved halohydrin dehalogenase into the plasmid pCK110900 operatively linked to the lac promoter under control of the lad repressor. The expression vector also contained the P15a origin of replication and the chloramphenicol resistance gene. Cells containing the subject polynucleotide in *Escherichia coli* W3110 were isolated by subjecting the cells to chloramphenicol selection. Another exemplary host cell is *Escherichia coli* BL21.

1.6 Methods of Generating Engineered Halohydrin Dehalogenase Polypeptides

In some embodiments, to make the improved HHDH polynucleotides and polypeptides of the present disclosure, the naturally-occurring halohydrin dehalogenase enzyme that catalyzes the conversion reaction is obtained (or derived) from *Agrobacterium radiobacter* or *Corynebacterium* sp. In some embodiments, the parent polynucleotide sequence is codon optimized to enhance expression of the halohydrin dehalogenase in a specified host cell.

The engineered halohydrin dehalogenases can be obtained by subjecting the polynucleotide encoding the naturally occurring halohydrin dehalogenase to mutagenesis and/or directed evolution methods, as discussed above. An exemplary directed evolution technique is mutagenesis and/or DNA shuffling as described in Stemmer, 1994, Proc Natl Acad Sci USA 91:10747-10751; WO 95/22625; WO 97/0078; WO 97/35966; WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc Natl Acad Sci USA 93:3525-3529).

The clones obtained following mutagenesis treatment are screened for engineered halohydrin dehalogenases having a desired improved enzyme property. Clones containing a polynucleotide encoding a halohydrin dehalogenase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical ligation methods, or polymerase mediated methods) to form any desired continuous sequence. For example, polynucleotides and oligonucleotides of the invention can be prepared by chemical synthesis using, e.g., the classical phosphoramidite method described by Beaucage et al., 1981, Tet Lett 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Midland Certified Reagent Company, Midland, Tex., The Great American Gene Company, Ramona, Calif., ExpressGen Inc. Chicago, Ill., Operon Technologies Inc., Alameda, Calif., and many others.

Engineered halohydrin dehalogenase enzymes expressed in a host cell can be recovered from the cells and or the culture medium using any one or more of the well known techniques for protein purification, including, among others, lysozyme treatment, sonication, high pressure homogenization (French Press), filtration, salting-out, ultra-centrifugation, and chromatography. Suitable solutions for lysing and the high efficiency extraction of proteins from bacteria, such as *E. coli*, are commercially available under the trade name CelLytic B™ from Sigma-Aldrich of St. Louis Mo.

Chromatographic techniques for isolation of the halohydrin dehalogenase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved halohydrin dehalogenase enzymes. For affinity chromatography purification, any antibody which specifically binds the halohydrin dehalogenase polypeptide may be used. For the production of antibodies, various host animals, including but not limited to rabbits, mice, rats, etc., may be immunized by injection with an engineered polypeptide. The polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

1.7 Methods of Using Engineered Halohydrin Dehalogenase Polypeptides

In another aspect, the present disclosure provides methods of using the engineered HHDH polypeptides for enantioselective ring opening reactions with epoxide substrates to prepare enantiospecific alcohols and/or resolve racemic epoxides. In another aspect, the present disclosure provides methods of using the engineered HHDH polypeptides for enantioselective ring closure reactions with alcohol substrates to prepare enantiospecific epoxides and/or resolve racemic epoxides. Illustrative ring opening and ring closing reactions that can be carried out using the engineered HHDH polypeptides of the present disclosure are provided in the Examples below.

In some embodiments, the HHDH enzymes described herein are capable of catalyzing the conversion of an epoxide in the compound of structural formula (I) (a "substrate") to the S-alcohol product of structural formula (II) (a "product"):

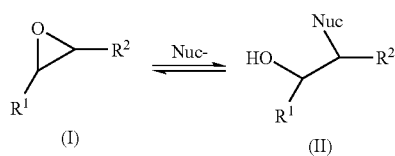

wherein, $R^1$ is a substituted or unsubstituted alkyl, cylcoalkyl, heteocycloalkyl, aryl, or heteroaryl; $R^2$ is H, or substituted or unsubstituted alkyl, cylcoalkyl, heteocycloalkyl, aryl, or heteroaryl; or wherein $R^1$ and $R^2$ forms a ring, such as a substituted or unsubstituted cycloalkyl or heterocycloalkyl; and Nuc is a suitable nucleophile, including but not limited to, $Br^-$, $Cl^-$, $I^-$, $NO_2^-$, $N_3^-$, $CN^-$, $OCN^-$, $SCN^-$, or formate ($HCOO^-$). In some embodiments, $R^1$ is a substituted or unsubstituted aryl, including among others, substituted or unsubstituted phenyl. In some embodiments, the epoxide of formula (I) is styrene oxide or para-nitro styrene oxide.

In some embodiments, the halohydrin dehalogenase polypeptides of the invention catalyze the enantioselective conversion of an epoxide in the compound of structural formula (I) to the R-alcohol "product" of formula (III):

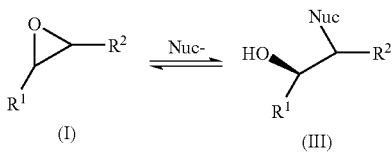

wherein, $R^1$, $R^2$ and Nuc are described above.

In some embodiments, the HHDH polypeptides of the invention can be used for the enantioselective conversion of an epoxide of structural formula (I) to the S-alcohol product of formula (IIIb):

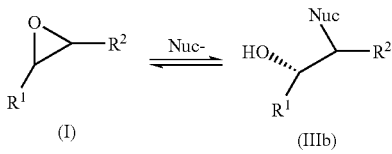

wherein $R^1$, $R^2$, and Nuc are as described previously.

In some embodiments, the HHDH polypeptides of the invention can be used for the enantioselective conversion of an epoxide of structural formula (I) to the S-alcohol product of formula (VIII):

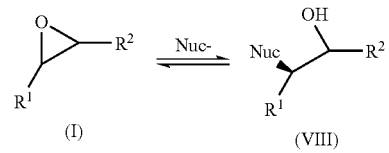

wherein $R^1$, $R^2$, and Nuc are as described previously.

In some embodiments, the HHDH polypeptides of the invention can be used for the enantioselective conversion of an epoxide of structural formula (I) to the S-alcohol product of formula (VIIIb):

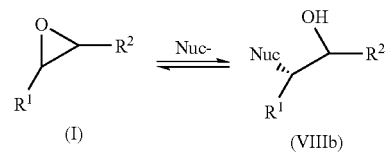

wherein $R^1$, $R^2$, and Nuc are as described previously. In the structures of formula (III), (Mb), (VIII) and (VIIIb), the carbon bonded to $R^1$ can be the alpha carbon of the epoxide ring.

In some embodiments, the HHDH polypeptides of the invention stereoselectively catalyze the conversion of the alcohol substrate of formula (IV), where X is halide:

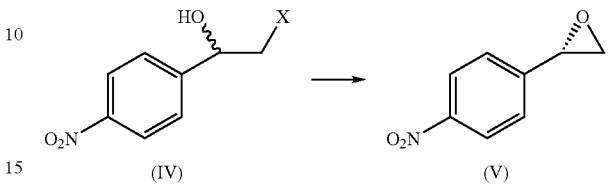

to the S-epoxide product of structural formula (V).

In some embodiments, the HHDH polypeptides of the invention stereoselectively catalyze the conversion of the alcohol substrate of formula (IV), where X is halide:

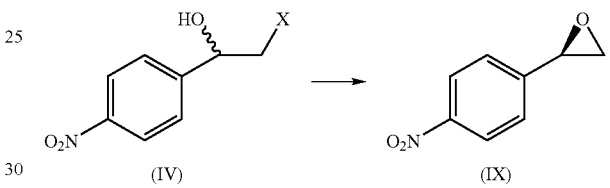

to the R-epoxide product of structural formula (IX).

Accordingly, in some embodiments, provided herein are methods for converting the epoxide of formula (I) to the alcohol of formula (II), formula (III), formula (Mb), formula (VIII), or formula (VIIIb), which method comprises contacting or incubating the epoxide with a halohydrin dehalogenase polypeptide of the disclosure in the presence of a nucleophile and under reaction conditions suitable for converting the substrate to the alcohol of structural formula (II), formula (III), formula (Mb), formula (VIII), or formula (VIIIb). In some embodiments, the nucleophile is selected from $Br^-$, $Cl^-$, $I^-$, $NO_2^-$, $N_3^-$, $CN^-$, $OCN^-$, $SCN^-$, or formate ($HCOO^-$). In some embodiments, the epoxide is styrene oxide.

In some embodiments, provided herein are methods for converting the alcohol of formula (II), formula (III), or formula (IV) to the epoxide of formula (I), formula (V), or formula (IX) which method comprises contacting or incubating the alcohol with a halohydrin dehalogenase polypeptide of the disclosure under reaction conditions suitable for converting the substrate to the epoxide of structural formula (I), formula (V), or formula (IX).

Any of the above-described methods of using engineered HHDH polypeptides can be carried out using whole cells capable of expressing the polypeptide, cell extracts, or purified HHDH enzymes. Furthermore, the methods can be carried out using a single HHDH enzyme or, alternatively, mixtures of two or more HHDH enzymes.

6. EXAMPLES

Various features and embodiments of the disclosure are illustrated in the following representative examples, which are intended to be illustrative, and not limiting.

Example 1

Engineered HHDH Polypeptides Capable of Catalyzing Ring Closure of PNSHH to PNSO with Improved Enantioselectivity The ring closure reaction converting PNSHH (compound (VI)) to PNSO (compound (VII)) is illustrated in Scheme 13 below.

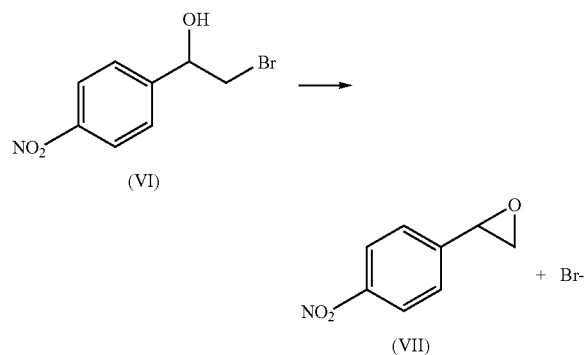

Scheme 13

A 100 mM stock solution of compound (VI) is prepared by dissolving 24.9 mg of compound (VI) in 1 mL of DMSO. The engineered HHDH enzyme stock solution is prepared by dissolving 10 mg dry lyophilized enzyme powder in 1 mL of a 100 mM Tris-SO$_4$ buffer of pH 7.5. The enzyme is diluted to the appropriate final concentration by adding 10 μL of enzyme stock solution to 940 μL, 100 mM Tris-SO$_4$ buffer of pH 7.5. The reaction is then started by adding 50 μL of compound (VI) to an end concentration of 5 mM (20× dilution) and the total volume is 1 mL. Note that not every enzyme variant is equally active and some tests should be done to optimize the final enzyme concentration to make sure the reaction is not too fast, resulting in a lower e.e. of the product.

Sample preparation is done as follows. Take a sample of the reaction mixture and extract with two volumes of heptane. Analysis of the organic layer is done on a Daicel Chiralcel AD-H column (0.46 cm×250 mm) equipped with AD-H guard column using heptane/ethanol 95:5 as eluent and a flow of 1 ml/min with detection at 216 nm. Under these conditions, baseline separation of the product compound (VII) is obtained but not of compound (VI). Elution order: R-product (5.3 min), S-product (5.8 min), compound (VI) (6.4 min, non-separated).

The enantioselectivity of the enzyme can be calculated from the percent conversion and the percent enantiomeric excess of the product using the formula of Chen et al., or be easily visualized by plotting % c vs. % e.e. Engineered HHDH polypeptides exhibiting improved enantioselectivity in catalyzing the ring closure reaction are listed below in Table 3.

TABLE 3

| SEQ ID NO: | Residue Differences (relative to SEQ ID NO: 244) | Selectivity | E-Value Result |
|---|---|---|---|
| 44 | P175M; | R | ++++ |
| 46 | P175L; | R | ++++ |
| 48 | P175V; | R | ++++ |
| 50 | P175G; | R | ++++ |

TABLE 3-continued

| SEQ ID NO: | Residue Differences (relative to SEQ ID NO: 244) | Selectivity | E-Value Result |
|---|---|---|---|
| 86 | I128V; L178C; | R | + |
| 244 | N/A | R | + |
| 248 | P175L; T222A; | R | ++++ |
| 252 | L178C; | R | + |
| 256 | A114V; L178C; | R | ++ |
| 260 | W139S; W249V; | S | + |
| 262 | W139T; W249H; | S | + |
| 264 | W139M; F223V; W249P; | S | + |
| 266 | W139T; | S | + |

+: E-value 0 to 10
++: E-value 20 to <40
+++: E-value 40 to 100
++++: E-value >100

Example 2

Engineered HHDH Polypeptides Capable of Catalyzing the Ring Opening of Styrene Oxide with Azide to Provide 1-Azido-2-Phenylethanol with Improved Enantioselectivity A deep well plate with HHDH enzymes is thawed at room temperature for ~30 min and centrifuged at 4,000 rpm (3220× g) for 5 min at 4° C. to spin down any condensation.

Prepare a 200 mM styrene oxide stock solution in DMSO by dissolving 33 mg/mL. To prepare a 30 mL volume of aqueous substrate buffer, add 1250 μL of the 200 mM Styrene oxide stock solution to 28.75 mL 100 mM Tris-SO$_4$, pH 7.5. Weigh out 16.3 mg NaN$_3$, add to the aqueous solution, and swirl to dissolve. To start the reaction, dispense 150 mL of substrate buffer to each well. Seal the deep well reaction plate at 180° C. for 3 sec, then react 3 hrs at room temperature with shaking.

Sample preparation is done as follows. After 3 hrs, add 0.5 mL of MTBE to each well. Seal the plate, and shake at 850 rpm for 10 min at room temperature. Centrifuge the plate at 2,000 rpm (3220×g) for 2 min to separate the phases. Transfer 150 μL of the organic phase from each well to a shallow well plate (Costar 3365). Seal the plate (Heat-sealer set at 170° C. for 2 sec).

Analyze by normal phase HPLC using the following conditions: 10 μL injection onto a Daicel Chiralcel AD-H column (0.46 cm×250 mm) equipped with AD-H guard column. Mobile Phase: 95:5 v/v Heptane/Ethanol; Flow-rate: 1 mL min$^{-1}$ for 14 min runtime; Column Temperature: 25° C.; detection wavelength: 215 nm. HPLC Retention times: (R)-styrene oxide: 3.3 min; (S)-styrene oxide: 3.5 min; (R)-2-azido-1-phenylethanol: 8.0 min; (R)-1-azido-2-phenylethanol: 8.6 min; (S)-1-azido-2-phenylethanol: 9.3 min; (S)-2-azido-1-phenylethanol: 11.0 min.

The enantioselectivity of the enzyme towards the product of ring opening at the beta position can be calculated from the percent conversion and the percent enantiomeric excess of the product using the formula of Chen, or be easily visualized by plotting % c vs. % e.e. Engineered HHDH polypeptides exhibiting altered or improved enantioselectivity in catalyzing the ring opening reaction are listed below in Table 4.

TABLE 4

| SEQ ID NO: | Residue Differences (relative to SEQ ID NO: 244) | Selectivity | % e.e. Product |
|---|---|---|---|
| 40 | W139S; | S | ++ |
| 116 | N113S; W139T; N176S; | R | +++ |

TABLE 4-continued

| SEQ ID NO: | Residue Differences (relative to SEQ ID NO: 244) | Selectivity | % e.e. Product |
|---|---|---|---|
| 120 | F243L; | S | + |
| 122 | W139M; F243S; | S | + |
| 124 | N176S; F243L; | R | + |
| 130 | E85V; F243S; | S | ++++ |
| 132 | D99N; W139M; | S | ++++ |
| 136 | W139S; F243S; | S | +++ |
| 140 | K121R; N176T; F243S; | S | + |
| 142 | N176T; | R | ++ |
| 144 | W139S; N176S; F243S; | S | − |
| 146 | W139S; N176S; | R | +++ |
| 148 | W139M; N176T; | R | +++ |
| 154 | W139M; N176S; F243L; | R | +++ |
| 156 | W139M; N176S; H201R; K204R; | R | +++ |
| 158 | S146P; N176S; F243S; | S | +++ |
| 162 | W139T; N176D; F243S; | S | ++ |
| 164 | W139M; N176D; | R | − |
| 166 | W139T; S180T; F243S; | S | ++ |
| 172 | W139M; N176D; F243S; | R | + |
| 244 | N/A | R | + |
| 268 | W139M; N176S; | R | +++ |
| 270 | W139S; N176T; | R | ++ |
| 272 | G25C; W139M; N176T; | R | +++ |
| 274 | D80V; W139S; | S | + |
| 276 | L62V; W139M; E197G; | S | ++ |
| 278 | E33G; W139T; N176S; | R | +++ |
| 282 | T3S; W139M; N176S; | R | ++++ |
| 284 | W139T; N176S; | R | +++ |
| 286 | W139M; | S | ++++ |
| 288 | E95G; W139M; F243S; | S | + |
| 290 | E85D; W139M; I168V; | S | ++++ |
| 292 | W139T; H201R; | S | ++ |
| 294 | V112A; W139S; | S | ++ |

−: 0 to <20% e.e. of product
+: 20 to <40% e.e. of product
++: 40 to <60% e.e. of product
+++: 60 to <80% e.e. of product
++++: 80 to 100% e.e. of product Example 3

Engineered HHDH Polypeptides Capable of Increased Regioselectivity in Catalyzing the Epoxide Ring Opening of Styrene Oxide with Azide A deep well plate containing engineered HHDH enzymes in each well is thawed at room temperature for ~30 min and centrifuged at 4,000 rpm (3220×g) for 5 min at 4° C. to spin down any condensation.

Prepare a 200 mM styrene oxide stock solution in DMSO by dissolving 33 mg/mL. To prepare a 30 mL volume of aqueous substrate buffer, add 1250 µL of the 200 mM styrene oxide stock solution to 28.75 mL 100 mM Tris-SO$_4$, pH 7.5. Weigh 16.3 mg NaN$_3$, add to the aqueous solution, and swirl to mix. To start the reaction, dispense 150 µL of substrate buffer into each well of the deep well plate. Seal the deep well reaction plate at 180° C. for 3 sec, then react 3 hrs at room temperature with shaking.

Sample preparation for HPLC analysis is done as follows. After 3 hrs, add 0.5 mL of MTBE to each well. Seal the plate, and shake at 850 rpm for 10 min at room temperature. Centrifuge the plate at 2,000 rpm (3220×g) for 2 min to separate the phases. Transfer 150 µL of the organic phase from each well to a shallow well plate (Costar 3365). Seal the plate with heat-sealer set at 170° C. for 2 sec.

Samples are analyzed by normal phase HPLC using the following conditions: 10 µL injection onto a Daicel Chiralcel AD-H column (0.46 cm×250 mm) equipped with AD-H guard column. Mobile Phase: 95:5 v/v Heptane/Ethanol; Flow-rate: 1 mL min-1 for 14 min runtime; Column Temperature: 25° C.; detection wavelength: 215 nm. Retention times: (R)-Styrene oxide: 3.3 min; (S)-Styrene oxide: 3.5 min; (R)-2-azido-1-phenylethanol: 8.0 min; (R)-1-azido-2-phenylethanol: 8.6 min; (S)-1-azido-2-phenylethanol: 9.3 min; (S)-2-azido-1-phenylethanol: 11.0 min.

The regioselectivity of the enzyme towards the alpha or beta position can be calculated from the percent conversion to beta product (1-azido-2-phenylethanol) and the percent conversion to alpha product (2-azido-1-phenylethanol). Engineered HHDH polypeptides exhibiting increased alpha or increased beta regioselectivity in catalyzing the ring opening reaction are listed below in Table 5.

TABLE 5

| SEQ ID NO: | Residue Differences (relative to SEQ ID NO: 244) | More alpha (relative to SEQ ID NO: 244) | More beta (relative to SEQ ID NO: 244) |
|---|---|---|---|
| 40 | W139S; | ++++ | |
| 116 | N113S; W139T; N176S; | | ++ |
| 120 | F243L; | + | |
| 122 | W139M; F243S; | + | |
| 124 | N176S; F243L; | | + |
| 130 | E85V; F243S; | + | |
| 132 | D99N; W139M; | ++++++ | |
| 136 | W139S; F243S; | + | |
| 140 | K121R; N176T; F243S; | | + |
| 142 | N176T; | | + |
| 144 | W139S; N176S; F243S; | + | |
| 146 | W139S; N176S; | | ++ |
| 148 | W139M; N176T; | | + |
| 154 | W139M; N176S; F243L; | | +++ |
| 156 | W139M; N176S; H201R; K204R; | | ++ |
| 158 | S146P; N176S; F243S; | + | |
| 162 | W139T; N176D; F243S; | | ++ |
| 164 | W139M; N176D; | | +++ |
| 166 | W139T; S180T; F243S; | | ++ |
| 172 | W139M; N176D; F243S; | | + |
| 268 | W139M; N176S; | | + |
| 268 | W139M; N176S; | | ++ |
| 270 | W139S; N176T; | | ++ |
| 272 | G25C; W139M; N176T; | | ++ |
| 274 | D80V; W139S; | +++ | |
| 276 | L62V; W139M; E197G; | ++++ | |
| 280 | W139T; N176D; | | ++ |
| 282 | T3S; W139M; N176S; | | ++ |
| 284 | W139T; N176S; | | ++ |
| 286 | W139M; | +++++++ | |
| 290 | E85D; W139M; I168V; | +++++ | |
| 294 | V112A; W139S; | +++ | |

+: 1 to <2 fold more
++: 2 to <3 fold more
+++: 3 to <4 fold more
++++: 4 to <5 fold more
+++++: 5 to <6 fold more
++++++: 6 to 7 fold more
+++++++: more than 7 fold more Example 4

Engineered HHDH Polypeptides Having Improved Refractoriness to Halide Inhibition in Catalyzing the Ring Closure Reaction Converting PNSHH to PNSO Assuming normal Michaelis Menten competitive inhibitive enzyme kinetics, from the ratio of initial reaction rate in the absence and presence of halide, it is possible to determine the degree of inhibition by halide formula below. $V_{obs}$ is the reaction rate in the presence of halide, $V_0$ is the uninhibited reaction rate, [I] is the halide concentration (100 mM in this example) and $K_i$ is the apparent inhibition constant.

$$V_{obs} = V_0 * \frac{1}{1 + \frac{[I]}{K_i}} \quad \text{Formula 1}$$

Determination of uninhibited reaction rate: To make the reaction mixture, mix 1 mL of PNSHH/DMSO stock solution (6.15 mg/mL PNSHH in DMSO) with 99 mL of 100 mM Tris-SO$_4$ buffer of pH 7.5 by manual shaking vigorously. Add 190 µL of the above solution and 10 µL of crude engineered HHDH enzyme lysate into UV assay plates using a Multimek or any other 96 channel liquid handler. The final concentration of PNSHH is 250 µM. Use a UV/Vis microtiter plate reader for kinetic study. Settings: Wavelength: 310 nm; reaction time 5 mins.

Determination of inhibited reaction rate: To make the reaction mixture, mix 1 mL of PNSHH/DMSO stock solution (6.15 mg/ml PNSHH in DMSO) with 99 mL of 100 mM Tris-Cl buffer of pH 7.5 by manual shaking vigorously. Add 190 µL of the above solution and 10 µL of crude engineered HHDH enzyme lysate into UV assay plates using a Multimek or any other 96 channel liquid handler. The final concentration of PNSHH is 250 µM. Use a UV/Vis microtiter plate reader for kinetic study. Settings: wavelength: 310 nm, reaction time 5 mins Engineered HHDH polypeptides exhibiting increased refractoriness to halide inhibition (e.g., decreased inhibition by halide as shown by increased apparent $K_i$) in catalyzing the ring closure reaction converting PNSHH (compound (VI)) to PNSO (compound (VII)) are listed below in Table 6.

TABLE 6

| SEQ ID NO: | Residue Differences (relative to SEQ ID NO: 244) | $K_i$ Fold Improved (relative to SEQ ID NO: 244) |
|---|---|---|
| 28 | F12G | ++ |
| 90 | N167H, L178V | ++++ |
| 94 | Y187S | ++ |
| 114 | F12Y | ++ |
| 118 | W139M, N176T, F223L, F243L | + |
| 148 | W139M, N176T | + |
| 172 | W139M, N176D, F243S | +++ |
| 254 | L178V | ++ |
| 256 | A114V, L178C | ++++ |
| 260 | W139S, W249V | +++ |
| 268 | W139M, N176S | + |

+: 1 to <2 fold higher $K_i$
++: 2 to <5 fold higher $K_i$
+++: 5 to <10 fold higher $K_i$
++++: 10 to 20 fold higher $K_i$ Example 5

Engineered HHDH Polypeptides Capable of Improved Activity in Catalyzing the Non-Terminal Epoxide Ring Closure Reaction of 2-Chloro-Cyclohexanol to Cyclohexene Oxide Thaw a deep well plate containing engineered HHDH cell lysate at room temperature for ~30 min and centrifuge the thawed plate at 4,000 rpm (3220×g) for 5 min at 4° C. to spin down any condensation.

A reaction mixture containing 50 mM 2-chloro-cyclohexanol in 100 mM Tris-SO$_4$, pH 7.5 was prepared. To start the reaction, dispense 150 µL of substrate buffer to each well containing 50 µL of crude engineered HHDH cell lysate. Seal the deep well reaction plate at 180° C. for 3 sec, then react 3 hrs at room temperature with shaking.

Sample preparation for achiral GC analysis is done as follows. After 3 hrs, add 1 mL of ethyl acetate to each well. Seal the plate, and shake at 850 rpm for 10 min at room temperature. Centrifuge the plate at 2,000 rpm (3220×g) for 2 min to separate the phases. Transfer 150 µL of the organic phase from each well to a shallow well plate (Costar 3365). Seal the plate (Heat-sealer set at 170° C. for 2 sec).

Analysis with achiral GC can be done using a standard Agilent HP5 column, 90° C., 10-15 psi, at a 100:1 split ratio, runtime 5 min. Epoxide (2.4 min) and haloalcohol (4.3 min) are easily separated.

Engineered HHDH polypeptides capable of improved activity in catalyzing the ring closure reaction of 2-chloro-cyclohexanol to cyclohexene oxide are listed below in Table 7.

TABLE 7

| SEQ ID NO: | Residue differences (relative to SEQ ID NO: 244) | Activity Fold Improvement (relative to SEQ ID NO: 244) |
|---|---|---|
| 62 | A134T; | ++ |
| 220 | V84I; | ++ |
| 228 | A134V; | + |
| 298 | V84F; | + |
| 302 | V84L; | +++ |
| 304 | V84M; | + |

+: 1 to <2 fold more active
++: 2 to 3 fold more active
+++: >3 fold more active Example 6

Engineered HHDH Polypeptides Capable of Improved Activity in the Non-Terminal Epoxide Ring Opening of Cis-2,3-Epoxybutane with Azide and Trans-2,3-Epoxybutane Thaw a deep well plate containing engineered HHDH cell lysate at room temperature for ~30 min and centrifuge the thawed plate at 4,000 rpm (3220×g) for 5 min at 4° C. to spin down any condensation.

A mixture of cis or trans epoxybutane in buffer and azide was prepared and dispensed in each well the deep well plate. Final concentrations epoxybutanes used: 20 mM cis-2,3-epoxy butane (or trans-2,3-epoxy butane) with 20 mM sodium azide. This mixture was reacted for 2 hrs at room temperature and extracted with MTBE (0.5 mL) containing 5 mM mesitylene as internal standard. GC analysis was done on a standard Agilent HP-1 column, 80° C., 13 psi, injector 250° C. at a 100:1 split ratio, run time 3.5 min. The epoxide is not retained on the column, but the retention times for the other analytes are: azidoalcohol from cis-2,3-epoxybutane: 2.24 min$^{-1}$; azidoalcohol from trans-2,3-epoxybutane: 2.33 min$^{-1}$; mesitylene standard: 3.32 min$^{-1}$.

Without having the analytically pure product standards, the fold improvement of conversion needed to be calculated as the rate of product peak formation relative to the rate of peak formation by parent.

Engineered HHDH polypeptides capable of at least 1.1-fold improved activity in the azidolysis of cis-2,3-epoxybutane relative to the HHDH polypeptide of SEQ ID NO:244 are listed below in Table 8.

TABLE 8

| SEQ ID NO: | Residue differences (relative to SEQ ID NO: 244) | Activity Fold Improvement (relative to SEQ ID NO: 244) |
|---|---|---|
| 30 | F12M; | + |
| 64 | N176H; | ++ |
| 66 | I63V; N176F; | + |
| 68 | N176M; | ++++ |
| 96 | Y187I; | ++ |
| 112 | D182S; | + |
| 178 | A82F; | + |
| 182 | A82L; | + |
| 186 | A82Y; | + |
| 210 | W86F; | + |
| 212 | R20C; W86H; G137W; | +++ |
| 214 | A134C; | + |
| 220 | V84I; | ++ |
| 226 | A134L; | +++ |
| 228 | A134V; | +++ |
| 238 | L142M; | + |
| 242 | L142C; | + |
| 246 | F12M; T67I; | + |

+: 1.1 to <1.5 fold improved
++: 1.5 to <2 fold improved
+++: 2 to 2.5 fold improved
++++: >2.5 fold improved Engineered HHDH polypeptides capable of at least 1.1-fold improved activity in the azidolysis of trans-2,3-epoxybutane relative to the HHDH polypeptide of SEQ ID NO:244 are listed below in Table 9.

TABLE 9

| SEQ ID NO: | Residue differences (relative to SEQ ID NO: 244) | Activity Fold Improvement (relative to SEQ ID NO: 244) |
|---|---|---|
| 30 | F12M; | + |
| 58 | P175C; | + |
| 64 | N176H; | + |
| 68 | N176M; | + |
| 82 | A82T; | + |
| 96 | Y187I; | ++ |
| 178 | A82F; | ++ |
| 180 | A82G; | + |
| 182 | A82L; | + |
| 184 | A82S; | + |
| 186 | A82Y; | ++ |
| 202 | A82I; | + |
| 204 | A82K; | + |
| 206 | A82M; | ++ |
| 210 | W86F; | ++ |
| 212 | R20C; W86H; G137W; | +++ |
| 214 | A134C; | ++ |
| 216 | A82N; | + |
| 218 | A82W; | ++ |
| 220 | V84I; | ++ |
| 226 | A134L; | +++ |
| 228 | A134V; | +++++ |
| 230 | L142G; | + |
| 232 | A134F; | + |
| 234 | A134M; | + |
| 236 | L142I; | + |
| 238 | L142M; | ++ |
| 242 | L142C; | ++ |
| 254 | L178V; | ++ |

TABLE 9-continued

| SEQ ID NO: | Residue differences (relative to SEQ ID NO: 244) | Activity Fold Improvement (relative to SEQ ID NO: 244) |
|---|---|---|
| 258 | Y186F; | + |
| 296 | V84C; | + |
| 300 | I81L; | + |

+: 1 to <1.5 fold improved
++: 1.5 to <3 fold improved
+++: 3 to <5 fold improved
++++: 5 to 10 fold improved
+++++: >10 fold improved Engineered HHDH polypeptides capable of at least 1.1-fold improved activity in the azidolysis of both cis- and trans-2,3-epoxybutane relative to the HHDH polypeptide of SEQ ID NO:244 are listed below in Table 10.

TABLE 10

| SEQ ID NO: | Residue differences (relative to SEQ ID NO: 244) | Activity Fold Improvement cis | Activity Fold Improvement trans |
|---|---|---|---|
| 30 | F12M; | + | + |
| 64 | N176H; | ++ | + |
| 68 | N176M; | ++ | + |
| 96 | Y187I; | ++ | ++ |
| 178 | A82F; | + | ++ |
| 182 | A82L; | + | + |
| 186 | A82Y; | + | ++ |
| 210 | W86F; | + | ++ |
| 212 | R20C; W86H; G137W; | ++ | +++ |
| 214 | A134C; | + | ++ |
| 220 | V84I; | ++ | ++ |
| 226 | A134L; | ++ | +++ |
| 228 | A134V; | ++ | +++++ |
| 238 | L142M; | + | ++ |
| 242 | L142C; | + | ++ |

+: 1 to <1.5 fold improved
++: 1.5 to <3 fold improved
+++: 3 to <5 fold improved
++++: 5 to 10 fold improved
+++++: >10 fold improved Example 7

Engineered HHDH Polypeptides Capable of Catalyzing the Ring Opening of an α,α-Disubstituted Styrene Oxide with Formate Nucleophile with Improved Enantioselectivity This example illustrates the ability of engineered HHDH polypeptides to catalyze the ring opening reaction of an α,α-disubstituted styrene oxide of compound of formula (X) using formate as nucleophile, as shown below in Scheme 12.

Scheme 12

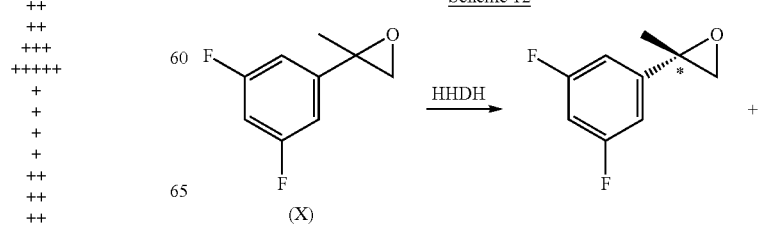

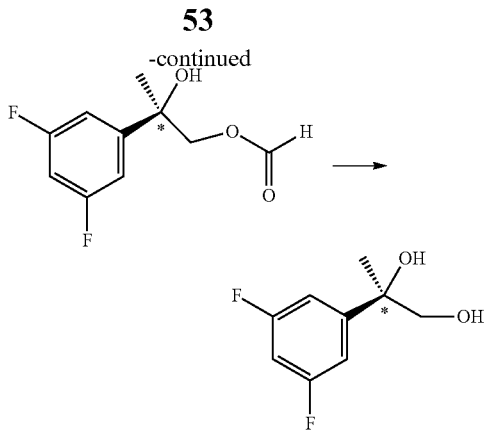

A deep well plate containing engineered HHDH polypeptides is thawed at room temperature for ~30 min and centrifuged at 4,000 rpm (3220×g) for 5 min at 4° C. to spin down any condensation.

A 40 g/L substrate stock solution of the α,α-disubstituted styrene oxide of compound (X) is prepared in DMSO. A 240 mM sodium formate solution is prepared in 100 mM phosphate at pH 6.5. Start the enzyme reaction by dispensing 250 µL of formate buffer and 15 µL of epoxide substrate stock solution in DMSO to each well of the plate containing the engineered HHDH polypeptides to give a final concentration in the screening of 2 g/L (11.8 mM) epoxide substrate of compound (X). The mixture is allowed to react for 18 hrs at 20° C. at which time it is analyzed by chiral chromatography.

In all samples, even negative control, peaks were detected representing epoxide, diol and two different carbonate esters indicating ring opening of the epoxide with subsequent hydrolysis of the labile formate ester product. However, since there was a relatively high rate of chemical ring opening by formate, it was impossible to distinguish between regioselectivity (i.e., alpha attack vs. beta attack) and transesterification of the resulting hydroxy ester. Consequently, this assay was only capable of identifying those HHDH variants having a relatively high degree of enantioselectivity in the enzymatic ring opening.

As shown in Table 11 below, enantiomeric enrichment in the remaining epoxide demonstrates that enantioselective ring opening of compound (X) using formate as nucleophile is catalyzed by the listed engineered HHDH polypeptides. Furthermore, the stereoselectivity varies depending on the variant HHDH used. Based on these results, at least the following positions and residue differences affect enantioselectivity of this reaction: X81E, M, or W; X82C, or S; X84I; X134I; X142G, or N; and X176D.

TABLE 11

| SEQ ID NO: | Residue Differences (relative to SEQ ID NO: 244) | % e.e. of remaining epoxide |
|---|---|---|
| 4 | WT HheC + W249F | 12 |
| 176 | A82C | −9 |
| 184 | A82S | −2 |
| 194 | I81E | −32 |
| 196 | I81M | −9 |
| 198 | I81W | −22 |
| 220 | V84I | −11 |
| 222 | A134I | 18 |
| 230 | L142G | −5 |
| 240 | L142N | −3 |

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An engineered halohydrin dehalogenase (HDDH) comprising an amino acid sequence at least 90% identical to SEQ ID NO: 244 and at least one amino acid residue difference at position 139 (X139) as compared to SEQ ID NO: 244, wherein said amino acid residue difference at X139 of SEQ ID NO: 244 is selected from amino acid residue G, I, L, M, P, S, T or V.

2. The engineered HHDH of claim 1, wherein the amino acid sequence has at least one residue difference as compared to SEQ ID NO:244 selected from:
   X12 is M, or S;
   X34 is G;
   X51 is P;
   X81 is E, F, M, W, or Y;
   X82 is C, G, K, L, M, N, or W;
   X83 is C or E;
   X84 is D;
   X85 is V;
   X86 is A or H;
   X110 is S,
   X131 is A;
   X134 is C, F, I, K, L, M, or V;
   X142 is C, M or N;
   X146 is P;
   X167 is H;
   X175 is C, G, I, L, M, N, or V;
   X176 is F, M, Q, or T;
   X177 is L, S or T;
   X178 is T;
   X182 is S;
   X186 is H;
   X187 is G, I, or S;
   X201 is R;
   X232 is S,
   X242 is A;
   X243 is C or L;
   X245 is S;
   X246 is S;
   X247 is N;
   X248 is V;
   X249 is A, G, H, I, or S;
   X252 is C; and
   X254 is N.

3. The engineered HHDH of claim 1 comprising an amino acid sequence selected from the group consisting of SEQ ID NO: 24, 32, 34, 36, 38, 40, 42, 100, 102, 104, 106, 108, 116, 118, 120, 122, 126, 128, 132, 134, 136, 138, 144, 146, 148, 150, 154, 156, 162, 164, 166, 168, 170, 172, 260, 262, 264, 266, 268, 270, 272, 274, 276, 278, 280, 282, 284, 286, 288, 290, 292, and 294.

4. The engineered HHDH of claim 1 which is capable of converting a racemic styrene oxide substrate to an S-azido alcohol product with an enantiomeric excess of at least 20% product and the amino acid sequence has one or more residue differences or groups of residue differences as compared to SEQ ID NO: 244 selected from:
   X62 is V, X139 is M and X197 is G;
   X80 is V and X139 is S;
   X85 is D, X139 is M and X 168 is V;
   X85 is V and X243 is S;
   X95 is G, X139 is M and X243 is S;
   X99 is N and X139 is M;
   X112 is A and X139 is S;
   X121 is R, X176 is T and X243 is S;
   X139 is S or M;
   X139 is T, X176 is D, and X243 is S;
   X139 is T, X180 is T, and X243 is S;
   X139 is T and X201 is R;
   X139 is S and X243 is S;
   X139 is M and X243 is S;
   X146 is P, X176 is S, and X243 is S; and
   X243 is L.

5. The engineered HHDH of claim 4, wherein the enantiomeric excess is at least 60% and the amino acid sequence has one or more residue differences or groups of residue differences as compared to SEQ ID NO: 244 selected from:
   X85 is D, X139 is M and X 168 is V;
   X85 is V and X243 is S;
   X99 is N and X139 is M;
   X139 is M;
   X139 is S and X243 is S; and
   X243 is L.

6. The engineered HHDH of any one of claim 1, wherein the HHDH is capable of producing R-azido alcohol from racemic styrene oxide with at least about 40% enantiomeric excess and the amino acid sequence has one or more residue differences or groups of residue differences as compared to SEQ ID NO: 244 selected from:
   X25 is C, X139 is M, and X176 is T;
   X33 is G, X139 is T, and X176 is S;
   X113 is S, X139 is T, and X176 is S;
   X139 is M, and X176 is S;
   X139 is M, and X176 is T;
   X139 is S, and X176 is S;
   X139 is T, and X176 is S;
   X139 is S, and X176 is T;
   X139 is M, X176 is S, X201 is R, and X204 is R;
   X139 is M, X176 is S, and X243 is L; and
   N176T.

7. The engineered HHDH of claim 6, wherein the HHDH is capable of producing R-azido alcohol from racemic styrene oxide with at least about 60% enantiomeric excess and the HHDH amino acid sequence one or more residue differences or groups of residue differences as compared to SEQ ID NO: 244 selected from:
   X25 is C, X139 is M, and X176 is T;
   X33 is G, X139 is T, and X176 is S;
   X113 is S, X139 is T, and X176 is S;
   X139 is M, and X176 is S;
   X139 is M, and X176 is T;

X139 is S, and X176 is S;
X139 is T, and X176 is S;
X139 is M, X176 is S, X201 is R, and X204 is R; and
X139 is M, X176 is S, and X243 is L.

8. The engineered HHDH of claim 1, wherein the HHDH has at least 3-fold increased α-regioselectivity as compared to the polypeptide of SEQ ID NO: 244 in the conversion of styrene oxide to the corresponding alcohol product and has one or more residue differences or groups of residue differences as compared to SEQ ID NO: 244 selected from:
X62 is V, X139 is M, and X197 is G;
X80 is V, and X139 is S;
X85 is D, X139 is M, and X168 is V;
X99 is N, and X139 is M;
X112 is A, and X139 is S;
X139 is M; and
X139 is S.

9. The engineered HHDH of claim 1, wherein the HHDH has at least 2-fold increased β-regioselectivity as compared to the polypeptide of SEQ ID NO: 244 in the conversion of styrene oxide to the corresponding alcohol product and has one or more residue differences or groups of residue differences as compared to SEQ ID NO: 244 selected from:
X3 is S, X139 is M, and X176 is S;
X25 is C, X139 is M, and X176 is T;
X113 is S, X139 is T, X176 is S;
X139 is S, X176 is S;
X139 is M, X176 is S, and X243 is L:
X139 is M, X176 is S, X201 is R, and X204 is R;
X139 is T, X176 is D, and X243 is S;
X139 is M, and X176 is D;
X139 is T, X180 is T, and X243 is S;
X139 is M, and X176 is S;
X139 is S, and X176 is T;
X139 is T, and X176 is D; and
X139 is T, and X176 is S.

10. The engineered HHDH of claim 1, wherein the HHDH has at least 5-fold increased $K_i$ for halide ion as compared to a reference HHDH polypeptide of SEQ ID NO: 4 and one or more residue differences or groups of residue differences as compared to SEQ ID NO: 244 selected from:
X12 is Y or G;
X114 is V, and X178 is C;
X139 is M and X176 is S;
X139 is M and X176 is T X139 is M, X176 is D, and X243 is S;
X139S and X249V;
X139 is M, X176 is T, X223 is L, and X243 is L;
X167 is H, and X178 is V;
X178 is V; and
X187 is S.

11. The engineered HHDH of claim 1, wherein the HHDH has an increased activity for converting an epoxide substrate of formula (I) to an alcohol product of formula (II) as compared to a reference polypeptide of SEQ ID NO: 4 or 244, wherein the epoxide substrate is cis- or trans-2,3-epoxybutane.

12. The engineered HHDH of claim 1, wherein the HHDH has at least 1.5 fold greater activity in the conversion of 2-chloro-cyclohexanol to cyclohexene oxide as compared to a reference polypeptide of SEQ ID NO: 244 amino acid sequence has one or more residue differences as compared to SEQ ID NO: 244 selected from:
X84 is L, I, M, or F;
X134 is T or V; and
X134 is T, X142 is L, and X245 is V.

13. The engineered HHDH of claim 1 which is capable of catalyzing a ring closure reaction converting para-nitro-styrene-hydroxy-halide (PNSHH) to para-nitro-styrene oxide (PNSO) with an enantiomeric excess corresponding to an E-value of at least 20 and has one or more residue differences or groups of residue differences as compared to SEQ ID NO: 244 selected from:
X114 is V and X178 is C;
X175 is G, L, M, or V; or
X175 is L, and X222 is A.

14. The engineered HHDH of claim 13, wherein the epoxide product in enantiomeric excess is S-para-nitro-styrene oxide (PNSO) and the amino acid sequence of the engineered HHDH has one or more residue differences or groups of residue differences as compared to SEQ ID NO: 244 selected from:
X139 is T;
X139 is S and X249 is V;
X139 is T and X249 is H; or
X139 is M, X223 is V, and X249 is P.

15. A method of converting an epoxide of formula (I) to an alcohol of formula (II),

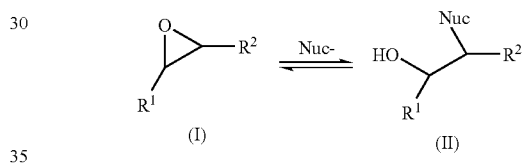

wherein,
$R^1$ is a substituted or unsubstituted alkyl, cylcoalkyl, heteocycloalkyl, aryl, or heteroaryl;
$R^2$ is H, or substituted or unsubstituted alkyl, cylcoalkyl, heteocycloalkyl, aryl, or heteroaryl; or wherein $R^1$ and $R^2$ forms a ring;
said method comprising contacting the epoxide of formula (I) with the engineered HHDH of claim 1 in the presence of a nucleophile (Nuc⁻) and under reaction conditions suitable for converting the epoxide to the alcohol product.

16. The method of claim 15, wherein $R^1$ is a substituted or unsubstituted aryl group, or substituted or unsubstituted phenyl group.

17. The method of claim 15, wherein the epoxide of formula (I) is a non-terminal epoxide.

18. The method of claim 15, wherein the epoxide is selected from the group consisting of: styrene oxide; para-nitrostyrene oxide; benzylethylene oxide; 1,2-epoxybutane; and 1,2 epoxyhexane.

19. The method of claim 15, wherein the nucleophile is selected from: Br⁻, Cl⁻, I⁻, $NO_2^-$, $N_3^-$, CN⁻, OCN⁻, SCN⁻, or formate.

* * * * *

SEQUENCE LISTING

```
<160> NUMBER OF SEQ ID NOS: 304

<210> SEQ ID NO 1
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 1
atgagcaccg ctattgtcac caacgtcaaa cattttggag gtatgggtag cgctctgcgt       60
ctgagcgaag ctggtcatac cgtcgcttgc catgatgaaa gctttaagca tcaggatgaa      120
ctagaagctt ttgctgaaac ctacccacag ctgataccaa tgagcgaaca ggaaccagct      180
gaactgattg aagctgtcac cagcgctctt ggtcatgtcg atgtcctggt cagcaacgat      240
atcgctcctg tggaatggcg gccaatcgat aaatacgctg tcgaggatta cagggatact      300
gtcgaagctc tgcagatcaa gccatttgct ctagtgaatg ctgtcgcttc gcaaatgaag      360
aagcgaaagt cggggcacat catcttcatc acttcggctg ccccgttcgg gccatggaag      420
gagatatcga cttactcttc ggctcgagct ggggctagtg cactagctaa tgccctatcg      480
aaggagctag gagagtacaa tatcccggtg ttcgctatcg ctccgaatta cctacactcg      540
```

```
gggggattcgc cgtactatta ccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg ccaggtgtt ttggttggca     720 ggcggctttc ccgctatcga acgttggccc ggcatgcccg aataa                    765
```

<210> SEQ ID NO 2
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 2

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Ile Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Ala Ile Glu Arg Trp Pro Gly Met Pro Glu
                245                 250
```

<210> SEQ ID NO 3
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 3

```
atgagcaccg ctatcgtcac caacgtcaaa cattttggag gtatgggtag cgctctgagg    60
```

```
ctgagcgaag ctggtcatac cgtcgcttgc catgatgaaa gctttaaaca gaaagatgaa      120
ctggaagctt ttgctgaaac ctacccacag ctgaaaccaa tgagcgaaca ggaaccagct      180
gaactgatcg aagctgtcac cagcgcttac ggtcaggtcg atgtcctggt cagcaacgat      240
atctttgctc cagaatttca gccaatcgat aaatacgctg tcgaagatta cagggtgct       300 gtcgaagctc tgcagatcag gccatttgct ctagtgaatg ctgtggcttc gcaaatgaag      360
aagcgaaagt cggggcacat catcttcatc acttcggcta ctccgttcgg gccatggaag      420
gagctatcga cttacacttc ggctcgagct ggggcttcta ctctagctaa tgctctatcg      480
aaggagctag agagtacaa tatcccggtg ttcgctatcg ggccgaatta cctacactcg        540
gaggattcgc cgtacttcta cccgactgag ccgtggaaga ctaatccgga gcacgtggct      600
cacgtgaaga aggtgactgc tctacaacga ctagggactc aaaaagagtt gggggaattg      660
gtggcatttt tggcatctgg ctcttgtgat tatttgactg gccaggtgtt ttggttggca      720
ggcggctttc ccatgataga acgtttcccc ggcatgcccg aataa                      765
```

<210> SEQ ID NO 4
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 4

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys Gln Lys Asp Glu Leu Glu Ala Phe Ala Glu Thr Tyr
        35                  40                  45

Pro Gln Leu Lys Pro Met Ser Glu Gln Glu Pro Ala Glu Leu Ile Glu
    50                  55                  60

Ala Val Thr Ser Ala Tyr Gly Gln Val Asp Val Leu Val Ser Asn Asp
65                  70                  75                  80

Ile Phe Ala Pro Glu Phe Gln Pro Ile Asp Lys Tyr Ala Val Glu Asp
                85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Thr Pro Phe Gly Pro Trp Lys Glu Leu Ser Thr
    130                 135                 140

Tyr Thr Ser Ala Arg Ala Gly Ala Ser Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240
```

Gly Gly Phe Pro Met Ile Glu Arg Phe Pro Gly Met Pro Glu
              245                 250

<210> SEQ ID NO 5
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 5

| | | |
|---|---|---|
| atgagcaccg ctattgtcac caacgtcaaa cattttggag gtatgggtag cgctctgcgt | 60 |
| ctgagcgaag ctggtcatac cgtcgcttgc catgatgaaa gctttaagca tcaggatgaa | 120 |
| ctagaagctt ttgctgaaac ctacccacag ctgataccaa tgagcgaaca ggaaccagct | 180 |
| gaactgattg aagctgtcac cagcgctctt ggtcatgtcg atgtcctggt cagcaacgat | 240 |
| atcgcgcctg tggaatggcg gccaatcgat aaatacgctg tcgaggatta cagggatact | 300 |
| gtcgaagctc tgcagatcaa gccatttgct ctagtgaatg ctgtcgcttc gcaaatgaag | 360 |
| aagcgaaagt cggggcacat catcttcatc acttcggctg ccccgttcgg gccatggaag | 420 |
| gagctatcga cttactcttc ggctcgagct ggggctagtg cactagctaa tgctctatcg | 480 |
| aaggagctag agagtacaa tatcccggtg ttcgctatcg ctccgaatta cctacactcg | 540 |
| ggggattcgc cgtactatta ccctctgag ccgtggaaga cttctccgga gcacgtggct | 600 |
| cacgtgcgta aggtgactgc tctacaacga ctagggactc aaaagagtt gggggaattg | 660 |
| gtgacgtttt tggcatctgg ctcttgtgat tatttgactg ccaggtgtt ttggttggca | 720 |
| ggcggctttc ccgtcatcga acgtcatccc ggcatgcccg aataa | 765 |

<210> SEQ ID NO 6
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 6

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser

```
           145                 150                 155                 160
Lys Glu Leu Gly Glu Tyr Asn Ile Pro Val Phe Ala Ile Ala Pro Asn
                165                 170                 175
Tyr Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
                195                 200                 205
Gln Arg Leu Gly Thr Gln Lys Glu Leu Gly Glu Leu Val Thr Phe Leu
            210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg His Pro Gly Met Pro Glu
                245                 250

<210> SEQ ID NO 7
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 7
atgagcaccg ctattgtcac caacgtcaaa cattttggag gtatgggtag cgctctgcgt      60
ctgagcgaag ctggtcatac cgtcgcttgc catgatgaaa gctttaagca tcagggtgaa     120
ctggaagctt ttgctgagac ctacccacag ctgataccaa tgagcgaaca ggaaccaact     180
gaactgattg aagctgtcac cggtgctctt ggtcaggtcg atgtcctggt cagcaacgat     240
atcgctcctg tggaatggcg gccaattgat aaatacgctg tcgaggatta cagggatact     300
gtcgaagctc tgcagatcaa gccatttttct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag gagagtacaa tatcccggtg ttcgctatcg ctccgaatta cctacactcg     540
ggggattcgc cgtactatta cccctctgag ccgtggaaga cttctccgga gcacgtggct     600
cacgtgcgta aggtgactgc tctacaacga ctagggactc aaaaagagtt gggggaattg     660
gtggcatttt tggcatctgg ctcttgtgat tatttgactg gccaggtgtt ttggttgaca     720
ggcggctttc ccgtcatcga acgttggccc ggcatgcccg aataa                     765

<210> SEQ ID NO 8
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 8

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Gly Glu Leu Glu Ala Phe Ala Glu Thr Tyr
        35                  40                  45

Pro Gln Leu Ile Pro Met Ser Glu Gln Glu Pro Thr Glu Leu Ile Glu
    50                  55                  60
```

```
Ala Val Thr Gly Ala Leu Gly Gln Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ser Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Leu Gly Leu Val Ala Phe Leu
    210                 215                 220

Ala Ser Gly Ser Cys Asp Tyr Leu Thr Gly Gln Val Phe Trp Leu Thr
225                 230                 235                 240

Gly Gly Phe Pro Val Ile Glu Arg Trp Pro Gly Met Pro Glu
                245                 250

<210> SEQ ID NO 9
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 9
atgagcaccg ctattgtcac caacgtccga cattttggag gtatgggtag cgctctgcgt        60
ctgagcgaag ctggtcatac cgtcgcttgc catgatgaaa gctttaagca tcaggatgaa       120
ctggaagctt ttgctgaaac ctacccacag ctgataccaa tgagcgaaca ggaaccaact       180
gaactgattg aagctgttac cagcgctctt ggtcatgtcg atgtcctggt cagcaacgat       240
atcgctgctg tggaatggcg gccaatcgat aaatacgctg tcgaggatta cagggatact       300
gtcgaagctc tgcagatcaa gccatttgct ctagtgaatg ctgtcgcttc gcaaatgaag       360
aagcgaaagt cggggcacat catcttcatc acttcggctg ccccgttcgg gccatggaag       420
gagctatcga cttactcttc ggctcgagct ggggctagtg cactagctaa tgctctatcg       480
aaggagctag agagtacaa tatcccggtg ttcgctatcg ctccgaatta cctacactcg        540
ggggattcgc cgtactatta ccctctgag ccgtggaaga cttctccgga gcacgtggct        600
cacgtgcgta aggtgactgc tctacaacga ctagggactc aacgcgagtt gggggaattg       660
gtggcatttt tggcatctgg ctcttgtgat tatttgactg gccaggtgtt ttggttggca       720
ggcggctttc ccgtcataga acgtcggccc ggcatgcccg aataa                      765

<210> SEQ ID NO 10
<211> LENGTH: 254
<212> TYPE: PRT
<213> ORGANISM: Artificial Sequence
<220> FEATURE:
<223> OTHER INFORMATION: Variant of halohydrin dehalogenase from A.
``` radiobacter

<400> SEQUENCE: 10

```
Met Ser Thr Ala Ile Val Thr Asn Val Arg His Phe Gly Gly Met Gly
1               5                  10                   15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Thr Glu Leu Ile Glu
    50                  55                  60
Ala Val Thr Ser Ala Leu Gly His Val Asp Val Leu Val Ser Asn Asp
65                  70                  75                  80
Ile Ala Ala Val Glu Trp Arg Pro Ile Asp Lys Tyr Ala Val Glu Asp
                85                  90                  95
Tyr Arg Asp Thr Val Glu Ala Leu Gln Ile Lys Pro Phe Ala Leu Val
            100                 105                 110
Asn Ala Val Ala Ser Gln Met Lys Lys Arg Lys Ser Gly His Ile Ile
        115                 120                 125
Phe Ile Thr Ser Ala Ala Pro Phe Gly Pro Trp Lys Glu Leu Ser Thr
    130                 135                 140
Tyr Ser Ser Ala Arg Ala Gly Ala Ser Ala Leu Ala Asn Ala Leu Ser
145                 150                 155                 160
Lys Glu Leu Gly Glu Tyr Asn Ile Pro Val Phe Ala Ile Ala Pro Asn
                165                 170                 175
Tyr Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
        195                 200                 205
Gln Arg Leu Gly Thr Gln Arg Glu Leu Gly Glu Leu Val Ala Phe Leu
    210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Arg Pro Gly Met Pro Glu
                245                 250
```

<210> SEQ ID NO 11
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 11

```
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttctg gccatggaag   420
gagctatcga cttactcttc ggctcgagct ggggctagtg cactagctaa tgctctatcg   480
aaggagctag agagtacaa tatcccggtg ttcgctatcg ctccgaatta cctacactcg   540
```

```
ggggattcgc cgtactatta ccctctgag ccgtggaaga cttctccgga gcacgtggct      600
cacgtgcgta aggtgactgc tctacaacga ctagggactc aaaaagagtt ggggggaattg    660 gtgacgtttt tggcatctgg ctcttgtgat tatttgactg ccaggtgtt ttggttggca      720 ggcggctttc ccgtcatcga acgttggccc ggcatacccg aataa                     765
```

<210> SEQ ID NO 12
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 12

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Trp Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Ile Pro Glu
                245                 250
```

<210> SEQ ID NO 13
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 13

```
atgagcaccg ctattgtcac caacgtcaaa cattttggag gtatgggtag cgctctgcgt    60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag gagagtacaa tatcccggtg ttcgctatcg ctccgaatta cgtacactcg    540
ggggattcgc cgtactatta cccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt tttgttggca    720
ggcggctttc ccgtcatcga acgttggccc ggcatgcccg aataa              765
```

<210> SEQ ID NO 14
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 14

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Val His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Leu Leu Ala
225                 230                 235                 240
```

Gly Gly Phe Pro Val Ile Glu Arg Trp Pro Gly Met Pro Glu
                245                 250

<210> SEQ ID NO 15
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 15

| | | |
|---|---|---|
| atgagcaccg ctattgtcac caacgtcaaa cattttggag gtatgggtag cgctctgcgt | 60 |
| ctgagcgaag ctggtcatac cgtcgcttgc catgatgaaa gctttaagca tcaggatgaa | 120 |
| ctagaagctt ttgctgaaac ctacccacag ctgataccaa tgagcgaaca ggaaccagct | 180 |
| gaactgattg aagctgtcac cagcgctctt ggtcatgtcg atatcctggt cagcaacgat | 240 |
| atcgcgcctg tggaatggcg gccaatcgat aaatacgctg tcgaggatta cagggatact | 300 |
| gtcgaagctc tgcagatcaa gccatttgct ctagtgaatg ctgtcgcttc gcaaatgaag | 360 |
| aagcgaaagt cggggcacat catcttcatc acttcggctg ccccgttcgg gccatggaag | 420 |
| gagctatcga cttactcttc ggctcgagct ggggctagtg cactagctaa tgctctatcg | 480 |
| aaggagctag agagtacaa tatcccggtg ttcgctatcg ctccgaatta cctacactcg | 540 |
| ggggattcgc cgtactatta cccctctgag ccgtggaaga cttctccgga gcacgtggct | 600 |
| cacgtgcgta aggtgactgc tctacaacga ctagggactc aaaaagagtt gggggaattg | 660 |
| gtgacgtttt tggcatctgg ctcttgtgat tatttgactg ccaggtgtt tttgttggca | 720 |
| ggcggctttc ccgtcatcga acgttggccc ggcatgcccg aataa | 765 |

<210> SEQ ID NO 16
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 16

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Ile Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser

```
                145                 150                 155                 160
Lys Glu Leu Gly Glu Tyr Asn Ile Pro Val Phe Ala Ile Ala Pro Asn
                    165                 170                 175

Tyr Leu His Ser Gly Asp Ser Pro Tyr Tyr Pro Ser Glu Pro Trp
                180                 185                 190

Lys Thr Ser Pro Glu His Val Ala His Val Arg Lys Val Thr Ala Leu
            195                 200                 205

Gln Arg Leu Gly Thr Gln Lys Glu Leu Gly Glu Leu Val Thr Phe Leu
        210                 215                 220

Ala Ser Gly Ser Cys Asp Tyr Leu Thr Gly Gln Val Phe Leu Leu Ala
225                 230                 235                 240

Gly Gly Phe Pro Val Ile Glu Arg Trp Pro Gly Met Pro Glu
                    245                 250

<210> SEQ ID NO 17
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 17
atgagcaccg ctattgtcac caacgtcaaa cattttggag gtatgggtag cgctctgcgt     60
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat agatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag gagagtacaa tatcccggtg ttcgctatcg ctccgaatta cctacactcg    540
ggggattcgc cgtactatta ccccactgag ccgtggaaga cttctctgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttgaca    720
ggcggctttc ccgtcatcga acgttggccc ggcatgcccg aataa                   765

<210> SEQ ID NO 18
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 18

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Arg Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Thr Glu Pro Trp
            180                 185                 190

Lys Thr Ser Leu Glu His Val Ala His Val Arg Lys Val Thr Ala Leu
        195                 200                 205

Gln Arg Leu Gly Thr Gln Lys Glu Leu Gly Leu Val Thr Phe Leu
    210                 215                 220

Ala Ser Gly Ser Cys Asp Tyr Leu Thr Gly Gln Val Phe Trp Leu Thr
225                 230                 235                 240

Gly Gly Phe Pro Val Ile Glu Arg Trp Pro Gly Met Pro Glu
                245                 250

<210> SEQ ID NO 19
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 19
atgagcacct ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt tgctgaaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat agatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta ccccactgag ccgtggaaga cttctctgga gcacgtggct     600
cacgtgcgca aggtgactgc tctacaacga ctagggactc aagaagagtt gggggaattg     660
gtaacctttt tggcatctgg ctcttgtgat tatttgactg gccaggtgtt ttggttgaca     720
ggcggctttc ccgtcatcga acgttggccc ggcatgcccg aataa                    765

<210> SEQ ID NO 20
<211> LENGTH: 254
<212> TYPE: PRT
<213> ORGANISM: Artificial Sequence
<220> FEATURE:
<223> OTHER INFORMATION: Variant of halohydrin dehalogenase from A.
```

-continued radiobacter

<400> SEQUENCE: 20

Met Ser Thr Ser Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Arg Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Thr Glu Pro Trp
            180                 185                 190

Lys Thr Ser Leu Glu His Val Ala His Val Arg Lys Val Thr Ala Leu
        195                 200                 205

Gln Arg Leu Gly Thr Gln Glu Glu Leu Gly Glu Leu Val Thr Phe Leu
    210                 215                 220

Ala Ser Gly Ser Cys Asp Tyr Leu Thr Gly Gln Val Phe Trp Leu Thr
225                 230                 235                 240

Gly Gly Phe Pro Val Ile Glu Arg Trp Pro Gly Met Pro Glu
                245                 250

<210> SEQ ID NO 21
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 21
atgagcaccg ctattgtcac caacgtcaaa cattttggag gtatgggtag cgctctgcgt     60
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcaggtcg atgtcctggt cagcaacgat    240
atcgctcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctctcga cttactcttc ggctcgagct ggggctagtg cactagctaa tgccctatcg    480
aaggagctag gagagtacaa tatcccggtg ttcgctatcg ctccgaatta cctacactcg    540

```
ggggattcgc cgtactatta ccoctctgag ccgtggaaga cttctccgga gcacgtggct    600
cacgtgcgta aggtgactgc tctacaacga ctagggactc aaaaagagtt ggggggaattg   660 gtgacgtttt tggcatctgg ctcttgtgat tatttgactg gccaggtgtt ttggttgaca    720
ggcggctttc ccgtcatcga acgttggccc ggcatgcccg aataa                   765
```

```
<210> SEQ ID NO 22
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 22
```

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly Gln Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Thr
225                 230                 235                 240

Gly Gly Phe Pro Val Ile Glu Arg Trp Pro Gly Met Pro Glu
                245                 250
```

```
<210> SEQ ID NO 23
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 23
```

```
atgagcaccg ctattgtcac caacgtcaaa cattttggag gtatgggtag cgctctgcgt    60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcgtgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatataag    420
gagttgtcga cttactcttc ggctcgagct ggggctagtg cactagctaa tgctctatcg    480
aaggagctag gagagtacaa tatcccggtg ttcgctatcg ctccgaatta cctacactcg    540
ggggattcgc cgtactacta cccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctttc ccgtcatcga acgtaggccc ggcatgcccg aataa               765
```

<210> SEQ ID NO 24
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 24

```
Met Ser Thr Ala Ile Val Thr Asn Val Lys His Phe Gly Gly Met Gly
 1               5                  10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly Arg Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Tyr Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

```
Gly Gly Phe Pro Val Ile Glu Arg Arg Pro Gly Met Pro Glu
                245                 250
```

<210> SEQ ID NO 25
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 25

```
atgagcaccg ctattgtcac caacgtcaaa cattcgggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgttctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgtttc gcaaatgaag   360
aagcgaaagt cggggcacat catcttcatc acttcggctg ccccgttcgg gccatggaag   420
gagctatcga cttactcttc ggctcgagct ggggctagtg cactagctaa tgctctatcg   480
aaggagctag agagtacaa tatcccggtg ttcgctatcg ctccgaatta cctacactcg   540
ggggattcgc cgtactatta ccctctgag ccgtggaaga cttctccgga gcacgtggct   600
cacgtgcgta aggtgactgc tctacaacga ctagggactc aaaaagagtt gggggaattg   660
gtgacgtttt tggcatctgg ctcttgtgat tatttgactg ccaggtgtt ttggttggca   720
ggcggctttc ccgtcatcga acgttggccc ggcatgcccg aataa             765
```

<210> SEQ ID NO 26
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 26

```
Met Ser Thr Ala Ile Val Thr Asn Val Lys His Ser Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Val Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Val Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
```

```
                145                 150                 155                 160
Lys Glu Leu Gly Glu Tyr Asn Ile Pro Val Phe Ala Ile Ala Pro Asn
                    165                 170                 175

Tyr Leu His Ser Gly Asp Ser Pro Tyr Tyr Pro Ser Glu Pro Trp
                180                 185                 190

Lys Thr Ser Pro Glu His Val Ala His Val Arg Lys Val Thr Ala Leu
            195                 200                 205

Gln Arg Leu Gly Thr Gln Lys Glu Leu Gly Glu Leu Val Thr Phe Leu
        210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                    245                 250
```

<210> SEQ ID NO 27
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 27

```
atgagcaccg ctattgtcac caacgtcaaa catgggggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccatggaag   420
gagctatcga cttactcttc ggctcgagct ggggctagtg cactagctaa tgctctatcg   480
aaggagctag gagagtacaa tatcccggtg ttcgctatcg ctccgaatta cctacactcg   540
ggggattcgc cgtactatta ccccctctga gccgtggaaga cttctccgga gcacgtggct   600
cacgtgcgta aggtgactgc tctacaacga ctagggactc aaaaagagtt ggggaattg    660
gtgacgtttt tggcatctgg ctcttgtgat tatttgactg gccaggtgtt ttggttggca   720
ggcggctttc ccgtcatcga acgttggccc ggcatgcccg aataa                   765
```

<210> SEQ ID NO 28
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 28

```
Met Ser Thr Ala Ile Val Thr Asn Val Lys His Gly Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
            195                 200                 205

Gln Arg Leu Gly Thr Lys Glu Leu Gly Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 29
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 29

```
atgagcaccg ctattgtcac caacgtcaaa catatgggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta ccctctgag ccgtggaaga cttctccgga gcacgtggct     600
cacgtgcgta aggtgactgc tctacaacga ctagggactc aaaaagagtt ggggaattg     660
gtgacgtttt tggcatctgg ctcttgtgat tatttgactg gccaggtgtt ttggttggca     720
ggcggctttc ccgtcatcga acgttggccc ggcatgcccg aataa                    765
```

<210> SEQ ID NO 30
<211> LENGTH: 254
<212> TYPE: PRT
<213> ORGANISM: Artificial Sequence
<220> FEATURE:
<223> OTHER INFORMATION: Variant of halohydrin dehalogenase from A.

radiobacter

<400> SEQUENCE: 30

```
Met Ser Thr Ala Ile Val Thr Asn Val Lys His Met Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 31
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 31

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaattaag     420
gagctatcga cttactcttc ggctcgagct ggggctagtg cactagctaa tgctctatcg     480
aaggagctag gagagtacaa tatcccggtg ttcgctatcg ctccgaatta cctacactcg     540
```

```
ggggattcgc cgtactatta ccctctgag ccgtggaaga cttctccgga gcacgtggct      600
cacgtgcgta aggtgactgc tctacaacga ctagggactc aaaaagagtt gggggaattg      660
gtgacgtttt tggcatctgg ctcttgtgat tatttgactg gccaggtgtt ttggttggca      720
ggcggctttc ccgtcatcga acgttggccc ggcatgcccg aataa                     765
```

```
<210> SEQ ID NO 32
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 32
```

```
Met Ser Thr Ala Ile Val Thr Asn Val Lys His Phe Gly Gly Met Gly
 1               5                  10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Ile Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

```
<210> SEQ ID NO 33
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 33
atgagcaccg ctattgtcac caacgtcaaa cattttggag gtatgggtag cgctctgcgt      60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccactgaag    420
gagctatcga cttactcttc ggctcgagct ggggctagtg cactagctaa tgctctatcg    480
aaggagctag gagagtacaa tatcccggtg ttcgctatcg ctccgaatta cctacactcg    540
ggggattcgc cgtactatta cccctctgag ccgtggaaga cttctccgga gcacgtggct    600
cacgtgcgta aggtgactgc tctacaacga ctagggactc aaaaagagtt ggggaattg    660
gtgacgtttt tggcatctgg ctcttgtgat tatttgactg ccaggtgtt ttggttggca    720
ggcggctttc ccgtcatcga acgttggccc ggcatgcccg aataa                   765
```

<210> SEQ ID NO 34
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 34

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Leu Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

```
Gly Gly Phe Pro Val Ile Glu Arg Trp Pro Gly Met Pro Glu
                245                 250
```

<210> SEQ ID NO 35
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 35

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccagttaag     420
gagctatcga cttactcttc ggctcgagct ggggctagtg cactagctaa tgctctatcg     480
aaggagctag agagtacaa tatcccggtg ttcgctatcg ctccgaatta cctacactcg      540
ggggattcgc cgtactatta cccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg ccaggtgtt ttggttggca     720
ggcggctttc ccgtcatcga acgttggccc ggcatgcccg aataa                    765
```

<210> SEQ ID NO 36
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 36

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Val Lys Glu Leu Ser Thr
    130                 135                 140

Tyr Ser Ser Ala Arg Ala Gly Ala Ser Ala Leu Ala Asn Ala Leu Ser
```

```
            145                 150                 155                 160
Lys Glu Leu Gly Glu Tyr Asn Ile Pro Val Phe Ala Ile Ala Pro Asn
                165                 170                 175
Tyr Leu His Ser Gly Asp Ser Pro Tyr Tyr Pro Ser Glu Pro Trp
                180                 185                 190
Lys Thr Ser Pro Glu His Val Ala His Val Arg Lys Val Thr Ala Leu
                195                 200                 205
Gln Arg Leu Gly Thr Gln Lys Glu Leu Gly Glu Leu Val Thr Phe Leu
                210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                245                 250
```

<210> SEQ ID NO 37
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 37

```
atgggcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggcgg ccccgttcgg gccaacgaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta cccctctgag ccgtggaaga cttctccgga gcacgtggct     600
cacgtgcgta aggtgactgc tctacaacga ctagggactc aaaaagagtt ggggaattg     660
gtgacgtttt tggcatctgg ctcttgtgat tatttgactg gccaggtgtt ttggttggca     720
ggcggctttc ccgtcatcga acgttggccc ggcatgcccg aataa                    765
```

<210> SEQ ID NO 38
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 38

```
Met Gly Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
                20                  25                  30
Glu Ser Phe Lys His Gln Asp Glu Leu Glu Ala Phe Ala Glu Thr Tyr
            35                  40                  45
Pro Gln Leu Ile Pro Met Ser Glu Gln Glu Pro Ala Glu Leu Ile Glu
        50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Arg Lys Ser Gly His Ile Ile
        115                 120                 125

Phe Ile Thr Ser Ala Ala Pro Phe Gly Pro Thr Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 39
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 39
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaagtaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta ccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                     765

<210> SEQ ID NO 40
<211> LENGTH: 254
<212> TYPE: PRT
<213> ORGANISM: Artificial Sequence
<220> FEATURE:
<223> OTHER INFORMATION: Variant of halohydrin dehalogenase from A.
``` radiobacter

<400> SEQUENCE: 40

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Ser Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 41
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 41

| | | | | | |
|---|---|---|---|---|---|
| atgagcaccg | ctattgtcac | caacgtcaaa | cattttggag | gtatgggtag | cgctctgcgt | 60 |
| ctgagcgaag | ctggtcatac | cgtcgcttgc | catgatgaaa | gctttaagca | tcaggatgaa | 120 |
| ctagaagctt | ttgctgaaac | ctacccacag | ctgataccaa | tgagcgaaca | ggaaccagct | 180 |
| gaactgattg | aagctgtcac | cagcgctctt | ggtcatgtcg | atgtcctggt | cagcaacgat | 240 |
| atcgcgcctg | tggaatggcg | gccaatcgat | aaatacgctg | tcgaggatta | cagggatact | 300 |
| gtcgaagctc | tgcagatcaa | gccatttgct | ctagtgaatg | ctgtcgcttc | gcaaatgaag | 360 |
| aagcgaaagt | cggggcacat | catcttcatc | acttcggctg | ccccgttcgg | gccaaataag | 420 |
| gagctatcga | cttactcttc | ggctcgagct | ggggctagtg | cactagctaa | tgctctatcg | 480 |
| aaggagctag | gagagtacaa | tatcccggtg | ttcgctatcg | ctccgaatta | cctacactcg | 540 |

```
gggggattcgc cgtactatta ccccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctttc ccgtcatcga acgttggccc ggcatgcccg aataa                     765
```

<210> SEQ ID NO 42
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 42

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Asn Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 43
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 43

```
atgagcaccg ctattgtcac caacgtcaaa cattttggag gtatgggtag cgctctgcgt    60
```

-continued

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag gagagtacaa tatcccggtg ttcgctatcg ctatgaatta cctacactcg    540
ggggattcgc cgtactatta cccctctgag ccgtggaaga cttctccgga gcacgtggct    600
cacgtgcgta aggtgactgc tctacaacga ctagggactc aaaaagagtt ggggaattg    660 gtgacgtttt tggcatctgg ctcttgtgat tatttgactg gccaggtgtt ttggttggca    720
ggcggctttc ccgtcatcga acgttggccc ggcatgcccg aataa                   765
```

<210> SEQ ID NO 44
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 44

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
                20                  25                  30

Glu Ser Phe Lys His Gln Asp Glu Leu Glu Ala Phe Ala Glu Thr Tyr
            35                  40                  45

Pro Gln Leu Ile Pro Met Ser Glu Gln Glu Pro Ala Glu Leu Ile Glu
        50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Met Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

Gly Gly Phe Pro Val Ile Glu Arg Trp Pro Gly Met Pro Glu
                245                 250

<210> SEQ ID NO 45
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 45

| | | | |
|---|---|---|---|
| atgagcaccg ctattgtcac caacgtcaaa cattttggag gtatgggtag cgctctgcgt | 60 |
| ctgagcgaag ctggtcatac cgtcgcttgc catgatgaaa gctttaagca tcaggatgaa | 120 |
| ctagaagctt ttgctgaaac ctacccacag ctgataccaa tgagcgaaca ggaaccagct | 180 |
| gaactgattg aagctgtcac cagcgctctt ggtcatgtcg atgtcctggt cagcaacgat | 240 |
| atcgcgcctg tggaatggcg gccaatcgat aaatacgctg tcgaggatta cagggatact | 300 |
| gtcgaagctc tgcagatcaa gccatttgct ctagtgaatg ctgtcgcttc gcaaatgaag | 360 |
| aagcgaaagt cggggcacat catcttcatc acttcggctg ccccgttcgg gccatggaag | 420 |
| gagctatcga cttactcttc ggctcgagct ggggctagtg cactagctaa tgctctatcg | 480 |
| aaggagctag agagtacaa tatcccggtg ttcgctatcg ctctgaatta cctacactcg | 540 |
| ggggattcgc cgtactatta ccctctgag ccgtggaaga cttctccgga gcacgtggct | 600 |
| cacgtgcgta aggtgactgc tctacaacga ctagggactc aaaaagagtt gggggaattg | 660 |
| gtgacgtttt tggcatctgg ctcttgtgat tatttgactg ccaggtgtt ttggttggca | 720 |
| ggcggctttc ccgtcatcga acgttggccc ggcatgcccg aataa | 765 |

<210> SEQ ID NO 46
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 46

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser

```
                145                 150                 155                 160
Lys Glu Leu Gly Glu Tyr Asn Ile Pro Val Phe Ala Ile Ala Leu Asn
                    165                 170                 175

Tyr Leu His Ser Gly Asp Ser Pro Tyr Tyr Pro Ser Glu Pro Trp
                180                 185                 190

Lys Thr Ser Pro Glu His Val Ala His Val Arg Lys Val Thr Ala Leu
                195                 200                 205

Gln Arg Leu Gly Thr Gln Lys Glu Leu Gly Glu Leu Val Thr Phe Leu
            210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                    245                 250

<210> SEQ ID NO 47
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 47
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctgtgaatta cctacactcg     540
ggggattcgc cgtactatta ccctctgag ccgtggaaga cttctccgga gcacgtggct     600
cacgtgcgta aggtgactgc tctacaacga ctagggactc aaaaagagtt ggggaattg     660 gtgacgtttt tggcatctgg ctcttgtgat tatttgactg gccaggtgtt ttggttggca     720
ggcggctttc ccgtcatcga acgttggccc ggcatgcccg aataa                    765

<210> SEQ ID NO 48
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 48

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60
```

Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Val Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 49
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 49
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctggtaatta cctacactcg     540
ggggattcgc cgtactatta ccccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                     765

<210> SEQ ID NO 50
<211> LENGTH: 254
<212> TYPE: PRT
<213> ORGANISM: Artificial Sequence
<220> FEATURE:
<223> OTHER INFORMATION: Variant of halohydrin dehalogenase from A.

radiobacter

<400> SEQUENCE: 50

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Gly Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 51
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 51
atgagcaccg ctattgtcac caacgtcaaa cattttggag gtatgggtag cgctctgcgt        60
ctgagcgaag ctggtcatac cgtcgcttgc catgatgaaa gctttaagca tcaggatgaa       120
ctagaagctt ttgctgaaac ctacccacag ctgataccaa tgagcgaaca ggaaccagct       180
gaactgattg aagctgtcac cagcgctctt ggtcatgtcg atgtcctggt cagcaacgat       240
atcgcgcctg tggaatggcg gccaatcgat aaatacgctg tcgaggatta cagggatact       300
gtcgaagctc tgcagatcaa gccatttgct ctagtgaatg ctgtcgcttc gcaaatgaag       360
aagcgaaagt cggggcacat catcttcatc acttcggctg ccccgttcgg gccatggaag       420
gagctatcga cttactcttc ggctcgagct ggggctagtg cactagctaa tgctctatcg       480
aaggagctag gagagtacaa tatcccggtg ttcgctatcg ctattaatta cctacactcg       540

```
ggggattcgc cgtactatta ccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg ccaggtgtt ttggttggca     720 ggcggctttc ccgtcatcga acgttggccc ggcatgcccg aataa                    765
```

```
<210> SEQ ID NO 52
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 52
```

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Ile Asn
                165                 170                 175

Tyr Leu His Ser Gly Asp Ser Pro Tyr Tyr Pro Ser Glu Pro Trp
            180                 185                 190

Lys Thr Ser Pro Glu His Val His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

```
<210> SEQ ID NO 53
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 53
```

```
atgagcaccg ctattgtcac caacgtcaaa cattttggag gtatgggtag cgctctgcgt    60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggcta ccccgttcgg gccatggaag    420
gagctatcga cttactcttc ggctcgagct ggggctagtg cactagctaa tgctctatcg    480
aaggagctag gagagtacaa tatcccggtg ttcgctatcg ctctgaatta cctacactcg    540
ggggattcgc cgtactatta cccctctgag ccgtggaaga cttctccgga gcacgtggct    600
cacgtgcgta aggtgactgc tctacaacga ctagggactc aaaaagagtt ggggaattg     660 gtgacgtttt tggcatctgg ctcttgtgat tatttgactg gccaggtgtt ttggttggca    720
ggcggctttc ccgtcatcga acgttggccc ggcatgcccg aataa                    765
```

<210> SEQ ID NO 54
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 54

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Thr Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Leu Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

Gly Gly Phe Pro Val Ile Glu Arg Trp Pro Gly Met Pro Glu
                245                 250

<210> SEQ ID NO 55
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 55
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccatggaag   420
gagctatcga cttactcttc ggctcgagct ggggctagtg cactagctaa tgctctatcg   480
aaggagctag agagtacaa tatcccggtg ttcgctatcg ctagtaatta cctacactcg   540
ggggattcgc cgtactatta ccctctgag ccgtggaaga cttctccgga gcacgtggct   600
cacgtgcgta aggtgactgc tctacaacga ctagggactc aaaaagagtt gggggaattg   660
gtgacgtttt tggcatctgg ctcttgtgat tatttgactg ccaggtgtt ttggttggca   720 ggcggctttc ccgtcatcga acgttggccc ggcatgcccg aataa             765

<210> SEQ ID NO 56
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 56

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser

```
145                 150                 155                 160
Lys Glu Leu Gly Glu Tyr Asn Ile Pro Val Phe Ala Ile Ala Ser Asn
                165                 170                 175
Tyr Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
            195                 200                 205
Gln Arg Leu Gly Thr Gln Lys Glu Leu Gly Glu Leu Val Thr Phe Leu
        210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                245                 250
```

<210> SEQ ID NO 57
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 57

```
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccatggaag   420
gagctatcga cttactcttc ggctcgagct ggggctagtg cactagctaa tgctctatcg   480
aaggagctag agagtacaa tatcccggtg ttcgctatcg cttgtaatta cctacactcg   540
ggggattcgc cgtactatta ccctctgag ccgtggaaga cttctccgga gcacgtggct   600
cacgtgcgta aggtgactgc tctacaacga ctagggactc aaaaagagtt ggggaattg   660
gtgacgtttt tggcatctgg ctcttgtgat tatttgactg gccaggtgtt ttggttggca   720
ggcggctttc ccgtcatcga acgttggccc ggcatgcccg aataa              765
```

<210> SEQ ID NO 58
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 58

```
Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Cys Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 59
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 59
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctaataatta cctacactcg     540
ggggattcgc cgtactatta ccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tattgactg gccaggtgtt ttggttggca     720
ggcggctttc ccgtcatcga acgttggccc ggcatgcccg aataa                    765

<210> SEQ ID NO 60
<211> LENGTH: 254
<212> TYPE: PRT
<213> ORGANISM: Artificial Sequence
<220> FEATURE:
<223> OTHER INFORMATION: Variant of halohydrin dehalogenase from A.
``` radiobacter

<400> SEQUENCE: 60

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Asn Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
            195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 61
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 61
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggcta ccccgttcgg gccatggaag     420
gagctatcga cttactcttc ggctcgagct ggggctagtg cactagctaa tgctctatcg     480
aaggagctag gagagtacaa tatcccggtg ttcgctatcg ctccgaatta cctacactcg     540

```
ggggattcgc cgtactatta cccctctgag ccgtggaaga cttctccgga gcacgtggct    600
cacgtgcgta aggtgactgc tctacaacga ctagggactc aaaaagagtt ggggggaattg    660 gtgacgtttt tggcatctgg ctcttgtgat tatttgactg gccaggtgtt ttggttggca    720
ggcggctttc ccgtcatcga acgttggccc ggcatgcccg aataa                    765
```

<210> SEQ ID NO 62
<211> LENGTH: 254
<212> TYPE: PRT
<213> ORGANISM: Artificial Sequence
<220> FEATURE:
<223> OTHER INFORMATION: Variant of halohydrin dehalogenase from A.
       radiobacter

<400> SEQUENCE: 62

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Thr Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 63
<211> LENGTH: 765
<212> TYPE: DNA
<213> ORGANISM: Artificial Sequence
<220> FEATURE:
<223> OTHER INFORMATION: Variant of halohydrin dehalogenase from A.
       radiobacter

<400> SEQUENCE: 63

```
atgagcaccg ctattgtcac caacgtcaaa cattttggag gtatgggtag cgctctgcgt    60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag gagagtacaa tatcccggtg ttcgctatcg ctccgcatta cctacactcg    540
ggggattcgc cgtactatta cccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctttc ccgtcatcga acgttggccc ggcatgcccg aataa                    765
```

<210> SEQ ID NO 64
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 64

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro His
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

Gly Gly Phe Pro Val Ile Glu Arg Trp Pro Gly Met Pro Glu
            245                 250

<210> SEQ ID NO 65
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 65

| | | |
|---|---|---|
| atgagcaccg ctattgtcac caacgtcaaa cattttggag gtatgggtag cgctctgcgt | 60 |
| ctgagcgaag ctggtcatac cgtcgcttgc catgatgaaa gctttaagca tcaggatgaa | 120 |
| ctagaagctt ttgctgaaac ctacccacag ctgataccaa tgagcgaaca ggaaccagct | 180 |
| gaactggttg aagctgtcac cagcgctctt ggtcatgtcg atgtcctggt cagcaacgat | 240 |
| atcgcgcctg tggaatggcg gccaatcgat aaatacgctg tcgaggatta cagggatact | 300 |
| gtcgaagctc tgcagatcaa gccatttgct ctagtgaatg ctgtcgcttc gcaaatgaag | 360 |
| aagcgaaagt cggggcacat catcttcatc acttcggctg ccccgttcgg gccatggaag | 420 |
| gagctatcga cttactcttc ggctcgagct ggggctagtg cactagctaa tgctctatcg | 480 |
| aaggagctag agagtacaa tatcccggtg ttcgctatcg ctccgtttta cctacactcg | 540 |
| ggggattcgc cgtactatta ccctctgag ccgtggaaga cttctccgga gcacgtggct | 600 |
| cacgtgcgta aggtgactgc tctacaacga ctagggactc aaaaagagtt gggggaattg | 660 |
| gtgacgtttt tggcatctgg ctcttgtgat tatttgactg gccaggtgtt ttggttggca | 720 |
| ggcggctttc ccgtcatcga acgttggccc ggcatgcccg aataa | 765 |

<210> SEQ ID NO 66
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 66

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Val Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser

```
          145                 150                 155                 160
Lys Glu Leu Gly Glu Tyr Asn Ile Pro Val Phe Ala Ile Ala Pro Phe
                    165                 170                 175
Tyr Leu His Ser Gly Asp Ser Pro Tyr Tyr Pro Ser Glu Pro Trp
                180                 185                 190
Lys Thr Ser Pro Glu His Val Ala His Val Arg Lys Val Thr Ala Leu
            195                 200                 205
Gln Arg Leu Gly Thr Gln Lys Glu Leu Gly Glu Leu Val Thr Phe Leu
        210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                    245                 250

<210> SEQ ID NO 67
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 67
atgagcaccg ctattgtcac caacgtcaaa cattttggag gtatgggtag cgctctgcgt     60
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag agagtacaa tatcccggtg ttcgctatcg ctccgatgta cctacactcg    540
ggggattcgc cgtactatta ccctctgag ccgtggaaga cttctccgga gcacgtggct    600
cacgtgcgta aggtgactgc tctacaacga ctagggactc aaaaagagtt ggggggaattg    660
gtgacgtttt tggcatctgg ctcttgtgat tatttgactg gccaggtgtt ttggttggca    720
ggcggctttc ccgtcatcga acgttggccc ggcatgcccg aataa               765

<210> SEQ ID NO 68
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 68

Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Met
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 69
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 69
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgcagta cctacactcg     540
ggggattcgc cgtactatta ccccctctgag ccgtggaaga cttctccgga gcacgtggct     600
cacgtgcgta aggtgactgc tctacaacga ctagggactc aaaaagagtt ggggaattg      660 gtgacgtttt tggcatctgg ctcttgtgat tatttgactg gccaggtgtt ttggttggca     720
ggcggctttc ccgtcatcga acgttggccc ggcatgcccg aataa                    765

<210> SEQ ID NO 70
<211> LENGTH: 254
<212> TYPE: PRT
<213> ORGANISM: Artificial Sequence
<220> FEATURE:
<223> OTHER INFORMATION: Variant of halohydrin dehalogenase from A.
``` radiobacter

<400> SEQUENCE: 70

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Gln
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 71
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 71
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag gagagtacaa tatcccggtg ttcgctatcg ctccgaattc gctacactcg     540

-continued

```
ggggattcgc cgtactatta cccctctgag ccgtggaaga cttctccgga gcacgtggct     600
cacgtgcgta aggtgactgc tctacaacga ctagggactc aaaaagagtt ggggaattg      660 gtgacgtttt tggcatctgg ctcttgtgat tatttgactg gccaggtgtt ttggttggca     720
ggcggctttc ccgtcatcga acgttggccc ggcatgcccg aataa                    765
```

<210> SEQ ID NO 72
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 72

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Ser Leu His Ser Gly Asp Ser Pro Tyr Tyr Pro Ser Glu Pro Trp
            180                 185                 190

Lys Thr Ser Pro Glu His Val His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 73
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 73

```
atgagcaccg ctattgtcac caacgtcaat cattttggag gtatgggtag cgctctgcgt     60
```

```
ctgagcgaag ctggtcatac cgtcgcttgc catgatgaaa gttttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag gagagtacaa tatcccggtg ttcgctatcg ctccgaatta cctacactcg    540
ggggattcgc cgtactatta cccctctgag ccgtggaaga cttctccgga gcacgtggct    600
cacgtgcgta aggtgactgc tctacaacga ctagggactc aaaaagagtt ggggaattg    660 gtgacgtttt tggcatctgg ctcttgtgat tatttgactg gccaggtgtt ttggttggca    720
ggcggctttc ccgtcatcga acgttggccc ggcatgcccg aataa              765
```

<210> SEQ ID NO 74
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 74

```
Met Ser Thr Ala Ile Val Thr Asn Val Asn His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

```
Gly Gly Phe Pro Val Ile Glu Arg Trp Pro Gly Met Pro Glu
                245                 250
```

<210> SEQ ID NO 75
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 75

```
atgagcaccg ctattgtcac caacgtcaga cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccatggaag   420
gagctatcga cttactcttc ggctcgagct ggggctagtg cactagctaa tgctctatcg   480
aaggagctag agagtacaa  tatcccggtg ttcgctatcg ctccgaataa tctacactcg   540
ggggattcgc cgtactatta ccctctgag  ccgtggaaga cttctccgga gcacgtggct   600
cacgtgcgta aggtgactgc tctacaacga ctagggactc aaaaagagtt gggggaattg   660
gtgacgtttt tggcatctgg ctcttgtgat tatttgactg ccaggtgtt  ttggttggca   720
ggcggctttc ccgtcatcga acgttggccc ggcatgcccg aataa                   765
```

<210> SEQ ID NO 76
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 76

```
Met Ser Thr Ala Ile Val Thr Asn Val Arg His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
```

```
                145                 150                 155                 160
Lys Glu Leu Gly Glu Tyr Asn Ile Pro Val Phe Ala Ile Ala Pro Asn
                    165                 170                 175

Asn Leu His Ser Gly Asp Ser Pro Tyr Tyr Pro Ser Glu Pro Trp
                180                 185                 190

Lys Thr Ser Pro Glu His Val Ala His Val Arg Lys Val Thr Ala Leu
            195                 200                 205

Gln Arg Leu Gly Thr Gln Lys Glu Leu Gly Glu Leu Val Thr Phe Leu
        210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 77
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 77
atgagcaccg ctattgtcac caacgtcaaa catttttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgaatac tctacactcg     540
ggggattcgc cgtactatta ccccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                    765

<210> SEQ ID NO 78
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 78

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Thr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 79
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 79
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag gagagtacaa tatcccggtg ttcgctatcg ctccgaattt gctacactcg     540
ggggattcgc cgtactatta cccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                    765

<210> SEQ ID NO 80
<211> LENGTH: 254
<212> TYPE: PRT
<213> ORGANISM: Artificial Sequence
<220> FEATURE:
<223> OTHER INFORMATION: Variant of halohydrin dehalogenase from A.
``` radiobacter

<400> SEQUENCE: 80

```
Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
Ala Val Thr Ser Ala Leu Gly His Val Asp Val Leu Val Ser Asn Asp
65                  70                  75                  80
Ile Ala Pro Val Glu Trp Arg Pro Ile Asp Lys Tyr Ala Val Glu Asp
                85                  90                  95
Tyr Arg Asp Thr Val Glu Ala Leu Gln Ile Lys Pro Phe Ala Leu Val
            100                 105                 110
Asn Ala Val Ala Ser Gln Met Lys Lys Arg Lys Ser Gly His Ile Ile
        115                 120                 125
Phe Ile Thr Ser Ala Ala Pro Phe Gly Pro Trp Lys Glu Leu Ser Thr
130                 135                 140
Tyr Ser Ser Ala Arg Ala Gly Ala Ser Ala Leu Ala Asn Ala Leu Ser
145                 150                 155                 160
Lys Glu Leu Gly Glu Tyr Asn Ile Pro Val Phe Ala Ile Ala Pro Asn
                165                 170                 175
Leu Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
        195                 200                 205
Gln Arg Leu Gly Thr Gln Lys Glu Leu Gly Glu Leu Val Thr Phe Leu
    210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                245                 250
```

<210> SEQ ID NO 81
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 81

| | | | | | |
|---|---|---|---|---|---|
| atgagcaccg | ctattgtcac | caacgtcaaa | cattttggag | gtatgggtag | cgctctgcgt | 60 |
| ctgagcgaag | ctggtcatac | cgtcgcttgc | catgatgaaa | gctttaagca | tcaggatgaa | 120 |
| ctagaagctt | ttgctgaaac | ctacccacag | ctgataccaa | tgagcgaaca | ggaaccagct | 180 |
| gaactgattg | aagctgtcac | cagcgctctt | ggtcatgtcg | atgtcctggt | cagcaacgat | 240 |
| atcacgcctg | tggaatggcg | gccaatcgat | aaatacgctg | tcgaggatta | cagggatact | 300 |
| gtcgaagctc | tgcagatcaa | gccatttgct | ctagtgaatg | ctgtcgcttc | gcaaatgaag | 360 |
| aagcgaaagt | cggggcacat | catcttcatc | acttcggctg | ccccgttcgg | gccatggaag | 420 |
| gagctatcga | cttactcttc | ggctcgagct | ggggctagtg | cactagctaa | tgctctatcg | 480 |
| aaggagctag | gagagtacaa | tatcccggtg | ttcgctatcg | ctccgaatta | cctacactcg | 540 |

```
ggggattcgc cgtactatta cccctctgag ccgtggaaga cttctccgga gcacgtggct    600
cacgtgcgta aggtgactgc tctacaacga ctagggactc aaaaagagtt ggggaattg    660 gtgacgtttt tggcatctgg ctcttgtgat tatttgactg gccaggtgtt ttggttggca    720
ggcggctttc ccgtcatcga acgttggccc ggcatgcccg aataa                   765
```

<210> SEQ ID NO 82
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 82

```
Met Ser Thr Ala Ile Val Thr Asn Val Lys His Phe Gly Gly Met Gly
 1               5                  10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Thr Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 83
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 83

```
atgagcaccg ctattgtcac caacgtcaaa cattttggag gtatgggtag cgctctgcgt    60
```

```
ctgagcgaag ctggtcatac cgtcgcttgc catgatgaag gctttaagca tcaggatgaa      120
ctagaagctt ttgctgaaac ctacccacag ctgataccaa tgagcgaaca ggaaccagct      180
gaactgattg aagctgtcac cagcgctctt ggtcatgtcg atgtcctggt cagcaacgat      240
atcgcgcctg tggaatggcg gccaatcgat aaatacgctg tcgaggatta cagggatact      300
gtcgaagctc tgcagatcaa gccatttgct ctagtgaatg ctgtcgcttc gcaaatgaag      360
aagcgaaagt cggggcacat catcttcatc acttcggctg ccccgttcgg gccatggaag      420
gagctatcga cttactcttc ggctcgagct ggggctagtg cactagctaa tgctctatcg      480
aaggagctag gagagtacaa tatcccggtg ttcgctatcg ctccgaatta cctacactcg      540
ggggattcgc cgtactatta cccctctgag ccgtggaaga cttctccgga gcacgtggct      600
cacgtgcgta aggtgactgc tctacaacga ctagggactc aaaaagagtt ggggaattg       660 gtgacgtttt tggcatctgg ctcttgtgat tatttgactg gccaggtgtt ttggttggca      720
ggcggctttc ccgtcatcga acgttggccc ggcatgcccg aataa                      765
```

<210> SEQ ID NO 84
<211> LENGTH: 254
<212> TYPE: PRT
<213> ORGANISM: Artificial Sequence
<220> FEATURE:
<223> OTHER INFORMATION: Variant of halohydrin dehalogenase from A.
    radiobacter

<400> SEQUENCE: 84

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Gly Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

Gly Gly Phe Pro Val Ile Glu Arg Trp Pro Gly Met Pro Glu
                245                 250

<210> SEQ ID NO 85
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 85

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat cgtcttcatc acttcggctg ccccgttcgg gccatggaag    420
gagctatcga cttactcttc ggctcgagct ggggctagtg cactagctaa tgctctatcg    480
aaggagctag agagtacaa tatcccggtg ttcgctatcg ctccgaatta ctgtcactcg    540
ggggattcgc cgtactatta cccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg ccaggtgtt ttggttggca    720 ggcggctttc ccgtcatcga acgttggccc ggcatgcccg aataa                    765
```

<210> SEQ ID NO 86
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 86

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Val
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser

```
                145                 150                 155                 160
Lys Glu Leu Gly Glu Tyr Asn Ile Pro Val Phe Ala Ile Ala Pro Asn
                    165                 170                 175

Tyr Cys His Ser Gly Asp Ser Pro Tyr Tyr Pro Ser Glu Pro Trp
                180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 87
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 87
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgaatta cacgcactcg     540
ggggattcgc cgtactatta ccccctctgag ccgtggaaga cttctccgga gcacgtggct     600
cacgtgcgta aggtgactgc tctacaacga ctagggactc aaaaagagtt ggggaattg      660 gtgacgtttt tggcatctgg ctcttgtgat tatttgactg gccaggtgtt ttggttggca     720
ggcggctttc ccgtcatcga acgttggccc ggcatgcccg aataa                     765

<210> SEQ ID NO 88
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 88

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Thr His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 89
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 89
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtaccaa tatcccggtg ttcgccatcg ctccgaatta cgtgcactcg     540
ggggattcgc cgtactatta cccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                    765

<210> SEQ ID NO 90
<211> LENGTH: 254
<212> TYPE: PRT
<213> ORGANISM: Artificial Sequence
<220> FEATURE:
<223> OTHER INFORMATION: Variant of halohydrin dehalogenase from A.
```

-continued radiobacter

<400> SEQUENCE: 90

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr His Ile Pro Val Phe Ala Ile Ala Pro Asn
                165                 170                 175

Tyr Val His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 91
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 91
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccatggaag   420
gagctatcga cttactcttc ggctcgagct ggggctagtg cactagctaa tgctctatcg   480
aaggagctag agagtacaa tatcccggtg ttcgctatcg ctccgaatta cctacactcg   540

```
ggggattcgc cgtactatgg gccctctgag ccgtggaaga cttctccgga gcacgtggct    600
cacgtgcgta aggtgactgc tctacaacga ctagggactc aaaaagagtt ggggaattg     660 gtgacgtttt tggcatctgg ctcttgtgat tatttgactg gccaggtgtt ttggttggca    720
ggcggctttc ccgtcatcga acgttggccc ggcatgcccg aataa                    765
```

<210> SEQ ID NO 92
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 92

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Gly Pro Ser Glu Pro Trp
            180                 185                 190

Lys Thr Ser Pro Glu His Val His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 93
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 93

```
atgagcaccg ctattgtcac caacgtcaaa cattttggag gtatgggtag cgctctgcgt    60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag gagagtacaa tatcccggtg ttcgctatcg ctccgaatta cctacactcg    540
ggggattcgc cgtactattc gccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctttc ccgtcatcga acgttggccc ggcatgcccg aataa                    765
```

<210> SEQ ID NO 94
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 94

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Ser Pro Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

```
Gly Gly Phe Pro Val Ile Glu Arg Trp Pro Gly Met Pro Glu
                245                 250
```

<210> SEQ ID NO 95
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 95

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatat tccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                    765
```

<210> SEQ ID NO 96
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 96

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
```

```
145                 150                 155                 160
Lys Glu Leu Gly Glu Tyr Asn Ile Pro Val Phe Ala Ile Ala Pro Asn
                165                 170                 175

Tyr Leu His Ser Gly Asp Ser Pro Tyr Ile Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 97
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 97

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatca cccctctgag ccgtggaaga cttctccgga gcacgtggct     600
cacgtgcgta aggtgactgc tctacaacga ctagggactc aaaaagagtt ggggaattg      660
gtgacgtttt tggcatctgg ctcttgtgat tatttgactg gccaggtgtt ttggttggca     720
ggcggctttc ccgtcatcga acgttggccc ggcatgcccg aataa                    765
```

<210> SEQ ID NO 98
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 98

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60
```

-continued

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr His Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 99
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 99
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaattaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta ccccctctgag ccgtggaaga cttctccgga gcacgtggct     600
cacgtgcgta aggtgactgc tctacaacga ctagggactc aaaaagagtt ggggaattg      660
gtgacgtttt tggcatctgg ctcttgtgat tatttgactg gccaggtgtt ttggttggca     720
ggcggctttc ccgtcatcga acgtgggccc ggcatgcccg aataa                     765

<210> SEQ ID NO 100
<211> LENGTH: 254
<212> TYPE: PRT
<213> ORGANISM: Artificial Sequence
<220> FEATURE:
<223> OTHER INFORMATION: Variant of halohydrin dehalogenase from A.

radiobacter

<400> SEQUENCE: 100

```
Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
Ala Val Thr Ser Ala Leu Gly His Val Asp Val Leu Val Ser Asn Asp
65              70                  75                  80
Ile Ala Pro Val Glu Trp Arg Pro Ile Asp Lys Tyr Ala Val Glu Asp
                85                  90                  95
Tyr Arg Asp Thr Val Glu Ala Leu Gln Ile Lys Pro Phe Ala Leu Val
            100                 105                 110
Asn Ala Val Ala Ser Gln Met Lys Lys Arg Lys Ser Gly His Ile Ile
        115                 120                 125
Phe Ile Thr Ser Ala Ala Pro Phe Gly Pro Ile Lys Glu Leu Ser Thr
    130                 135                 140
Tyr Ser Ser Ala Arg Ala Gly Ala Ser Ala Leu Ala Asn Ala Leu Ser
145             150                 155                 160
Lys Glu Leu Gly Glu Tyr Asn Ile Pro Val Phe Ala Ile Ala Pro Asn
                165                 170                 175
Tyr Leu His Ser Gly Asp Ser Pro Tyr Tyr Tyr Pro Ser Glu Pro Trp
            180                 185                 190
Lys Thr Ser Pro Glu His Val Ala His Val Arg Lys Val Thr Ala Leu
        195                 200                 205
Gln Arg Leu Gly Thr Gln Lys Glu Leu Gly Glu Leu Val Thr Phe Leu
    210                 215                 220
Ala Ser Gly Ser Cys Asp Tyr Leu Thr Gly Gln Val Phe Trp Leu Ala
225             230                 235                 240
Gly Gly Phe Pro Val Ile Glu Arg Gly Pro Gly Met Pro Glu
                245                 250
```

<210> SEQ ID NO 101
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 101

```
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccattgaag   420
gagctatcga cttactcttc ggctcgagtt ggggctagtg cactagctaa tgctctatcg   480
aaggagctag gagagtacaa tatcccggtg ttcgctatcg ctccgaatta cctacactcg   540
```

```
ggggattcgc cgtactatta cccctctgag ccgtggaaga cttctccgga gcacgtggct      600
cacgtgcgta aggtgactgc tctacaacga ctagggactc aaaaagagtt gggggaattg      660
gtgacgtttt tggcatctgg ctcttgtgat tatttgactg gccaggtgtt ttggttggca      720
ggcggctttc ccgtcatcga acgtattccc ggcatgcccg aataa                      765
```

<210> SEQ ID NO 102
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 102

```
Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
Ala Val Thr Ser Ala Leu Gly His Val Asp Val Leu Val Ser Asn Asp
65                  70                  75                  80
Ile Ala Pro Val Glu Trp Arg Pro Ile Asp Lys Tyr Ala Val Glu Asp
                85                  90                  95
Tyr Arg Asp Thr Val Glu Ala Leu Gln Ile Lys Pro Phe Ala Leu Val
            100                 105                 110
Asn Ala Val Ala Ser Gln Met Lys Lys Arg Lys Ser Gly His Ile Ile
        115                 120                 125
Phe Ile Thr Ser Ala Ala Pro Phe Gly Pro Leu Lys Glu Leu Ser Thr
    130                 135                 140
Tyr Ser Ser Ala Arg Val Gly Ala Ser Ala Leu Ala Asn Ala Leu Ser
145                 150                 155                 160
Lys Glu Leu Gly Glu Tyr Asn Ile Pro Val Phe Ala Ile Ala Pro Asn
                165                 170                 175
Tyr Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
        195                 200                 205
Gln Arg Leu Gly Thr Gln Lys Glu Leu Gly Glu Leu Val Thr Phe Leu
    210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Ile Pro Gly Met Pro Glu
                245                 250
```

<210> SEQ ID NO 103
<211> LENGTH: 744
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 103

```
atgagcaccg ctattgtcac caacgtcaaa cattttggag gtatgggtag cgctctgcgt      60
```

```
ctgagcgaag ctggtcatac cgtcgcttgc catgatgaaa gctttaagca tcaggatgaa      120
ctagaagctt ttgctgaaac ctacccacag ctgataccaa tgagcgaaca ggaaccagct      180
gaactgattg aagctgtcac cagcgctctt ggtcatgtcg atgtcctggt cagcaacgat      240
atcgcgcctg tggaatggcg gccaatcgat aaatacgctg tcgaggatta cagggatact      300
gtcgaagctc tgcagatcaa gccatttgct ctagtgaatg ctgtcgcttc gcaaatgaag      360
aagcgaaagt cggggcacat catcttcatc acttcggctg ccccgttcgg gccacttaag      420
gagctatcga cttactcttc ggctcgagct ggggctagtg cactagctaa tgctctatcg      480
aaggagctag gagagtacaa tatcccggtg ttcgctatcg ctccgaatta cctacactcg      540
ggggattcgc cgtactatta cccctctgag ccgtggaaga cttctccgga gcacgtggct      600
cacgtgcgta aggtgactgc tctacaacga ctagggactc aaaaagagtt gggggaattg      660
gtgacgtttt tggcatctgg ctcttgtgat tatttgactg gccaggtgtt ttggttggca      720
ggcggctttc ccgtcatcga acgt                                              744
```

<210> SEQ ID NO 104
<211> LENGTH: 248
<212> TYPE: PRT
<213> ORGANISM: Artificial Sequence
<220> FEATURE:
<223> OTHER INFORMATION: Variant of halohydrin dehalogenase from A.
    radiobacter

<400> SEQUENCE: 104

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Leu Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

Gly Gly Phe Pro Val Ile Glu Arg
                245

<210> SEQ ID NO 105
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 105
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccaccgaag   420
gagctatcga cttactcttc ggctcgagct ggggctagtg cactagctaa tgctctatcg   480
aaggagctag agagtacaa tatcccggtg ttcgctatcg ctccgaatta cctacactcg    540
ggggattcgc cgtactatta cccctctgag ccgtggaaga cttctccgga gcacgtggct   600
cacgtgcgta aggtgactgc tctacaacga ctagggactc aaaaagagtt gggggaattg   660
gtgacgtttt tggcatctgg ctcttgtgat tatttgactg ccaggtgtt ttggttggca    720 ggcggctttc ccgtcatcga acgtgctccc ggcatgcccg aataa                   765

<210> SEQ ID NO 106
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 106

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Pro Lys Glu Leu Ser Thr
    130                 135                 140

Tyr Ser Ser Ala Arg Ala Gly Ala Ser Ala Leu Ala Asn Ala Leu Ser

```
        145                 150                 155                 160
Lys Glu Leu Gly Glu Tyr Asn Ile Pro Val Phe Ala Ile Ala Pro Asn
                    165                 170                 175

Tyr Leu His Ser Gly Asp Ser Pro Tyr Tyr Pro Ser Glu Pro Trp
                180                 185                 190

Lys Thr Ser Pro Glu His Val Ala His Val Arg Lys Val Thr Ala Leu
            195                 200                 205

Gln Arg Leu Gly Thr Gln Lys Glu Leu Gly Glu Leu Val Thr Phe Leu
        210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Ala Pro Gly Met Pro Glu
                245                 250

<210> SEQ ID NO 107
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 107
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaggtaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta cccctctgag ccgtggaaga cttctccgga gcacgtggct     600
cacgtgcgta aggtgactgc tctacaacga ctagggactc aaaaagagtt ggggaattg      660 gtgacgtttt tggcatctgg ctcttgtgat tatttgactg gccaggtgtt ttggttggca     720
ggcggctttc ccgtcatcga acgtagtccc ggcatgcccg aataa                    765

<210> SEQ ID NO 108
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 108

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Arg Lys Ser Gly His Ile Ile
        115                 120                 125

Phe Ile Thr Ser Ala Ala Pro Phe Gly Pro Gly Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Ser Pro Gly Met Pro Glu
                245                 250

<210> SEQ ID NO 109
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 109
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag gagagtacaa tatcccggtg ttcgctatcg ctccgaatta cctacactcg     540
ggggattcgc cgtaccatta cccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                    765

<210> SEQ ID NO 110
<211> LENGTH: 254
<212> TYPE: PRT
<213> ORGANISM: Artificial Sequence
<220> FEATURE:
<223> OTHER INFORMATION: Variant of halohydrin dehalogenase from A.
```

-continued radiobacter

<400> SEQUENCE: 110

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65              70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr His Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 111
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 111

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag gagagtacaa tatcccggtg ttcgctatcg ctccgaatta cctacactcg     540
```

```
gggagttcgc cgtactatta cccctctgag ccgtggaaga cttctccgga gcacgtggct      600
cacgtgcgta aggtgactgc tctacaacga ctagggactc aaaaagagtt ggggaattg       660 gtgacgtttt tggcatctgg ctcttgtgat tatttgactg ccaggtgtt  ttggttggca      720 ggcggctttc ccgtcatcga acgttggccc ggcatgcccg aataa                      765
```

<210> SEQ ID NO 112
<211> LENGTH: 254
<212> TYPE: PRT
<213> ORGANISM: Artificial Sequence
<220> FEATURE:
<223> OTHER INFORMATION: Variant of halohydrin dehalogenase from A.
    radiobacter

<400> SEQUENCE: 112

```
Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
Ala Val Thr Ser Ala Leu Gly His Val Asp Leu Val Ser Asn Asp
65                  70                  75                  80
Ile Ala Pro Val Glu Trp Arg Pro Ile Asp Lys Tyr Ala Val Glu Asp
                85                  90                  95
Tyr Arg Asp Thr Val Glu Ala Leu Gln Ile Lys Pro Phe Ala Leu Val
            100                 105                 110
Asn Ala Val Ala Ser Gln Met Lys Lys Arg Lys Ser Gly His Ile Ile
        115                 120                 125
Phe Ile Thr Ser Ala Ala Pro Phe Gly Pro Trp Lys Glu Leu Ser Thr
    130                 135                 140
Tyr Ser Ser Ala Arg Ala Gly Ala Ser Ala Leu Ala Asn Ala Leu Ser
145                 150                 155                 160
Lys Glu Leu Gly Glu Tyr Asn Ile Pro Val Phe Ala Ile Ala Pro Asn
                165                 170                 175
Tyr Leu His Ser Gly Ser Ser Pro Tyr Tyr Pro Ser Glu Pro Trp
            180                 185                 190
Lys Thr Ser Pro Glu His Val Ala His Val Arg Lys Val Thr Ala Leu
        195                 200                 205
Gln Arg Leu Gly Thr Gln Lys Glu Leu Gly Glu Leu Val Thr Phe Leu
    210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                245                 250
```

<210> SEQ ID NO 113
<211> LENGTH: 765
<212> TYPE: DNA
<213> ORGANISM: Artificial Sequence
<220> FEATURE:
<223> OTHER INFORMATION: Variant of halohydrin dehalogenase from A.
    radiobacter

<400> SEQUENCE: 113

```
atgagcaccg ctattgtcac caacgtcaaa cattacggag gtatgggtag cgctctgcgt      60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag gagagtacaa tatcccggtg ttcgctatcg ctccgaatta cctacactcg    540
ggggattcgc cgtactatta ccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctttc ccgtcatcga acgttggccc ggcatgcccg aataa                    765
```

<210> SEQ ID NO 114
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 114

```
Met Ser Thr Ala Ile Val Thr Asn Val Lys His Tyr Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

Gly Gly Phe Pro Val Ile Glu Arg Trp Pro Gly Met Pro Glu
                245                 250

<210> SEQ ID NO 115
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 115
atgagcaccg ctattgtcac caacgtcaaa cattttggag gtatgggtag cgctctgcgt     60
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgagtg ctgtcgcttc gcaaatgaag    360
aagcgaaagt cggggcacat catcttcatc acttcggctg ccccgttcgg gccaacgaag    420
gagctatcga cttactcttc ggctcgagct ggggctagtg cactagctaa tgctctatcg    480
aaggagctag agagtacaa tatcccggtg ttcgctatcg ctccgagtta cctacactcg    540
ggggattcgc cgtactatta ccctctgag ccgtggaaga cttctccgga gcacgtggct    600
cacgtgcgta aggtgactgc tctacaacga ctagggactc aaaaagagtt ggggaattg    660 gtgacgtttt tggcatctgg ctcctgtgat tatttgactg gccaggtgtt ttggttggca    720
ggcggctttc ccgtcatcga acgttggccc ggcatgcccg aataa                    765

<210> SEQ ID NO 116
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 116

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Ser Ala Val Ala Ser Gln Met Lys Lys Arg Lys Ser Gly His Ile Ile
        115                 120                 125

Phe Ile Thr Ser Ala Ala Pro Phe Gly Pro Thr Lys Glu Leu Ser Thr
    130                 135                 140

Tyr Ser Ser Ala Arg Ala Gly Ala Ser Ala Leu Ala Asn Ala Leu Ser

```
            145                 150                 155                 160
Lys Glu Leu Gly Glu Tyr Asn Ile Pro Val Phe Ala Ile Ala Pro Ser
                165                 170                 175
Tyr Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
        195                 200                 205
Gln Arg Leu Gly Thr Gln Lys Glu Leu Gly Glu Leu Val Thr Phe Leu
    210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                245                 250

<210> SEQ ID NO 117
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 117
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaatgaag     420
gagctatcga cttactcttc ggctcgagct ggggctagtg cactagctaa tgctctatcg     480
aaggagctag gagagtacaa tatcccggtg ttcgctatcg ctccgactta cctacactcg     540
ggggattcgc cgtactatta ccccctctga gccgtggaaga cttctccgga gcacgtggct     600
cacgtgcgta aggtgactgc tctacaacga ctagggactc aaaaagagtt ggggaattg      660 gtgacgcttt tggcatctgg ctcttgtgat tatttgactg gccaggtgtt ttggttggca     720
ggcggtttgc ccgtcatcga acgttggccc ggcatgcccg aataa                     765

<210> SEQ ID NO 118
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 118

Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Met Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Thr
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Leu Val Thr Leu Leu
    210                 215                 220

Ala Ser Gly Ser Cys Asp Tyr Leu Thr Gly Gln Val Phe Trp Leu Ala
225                 230                 235                 240

Gly Gly Leu Pro Val Ile Glu Arg Trp Pro Gly Met Pro Glu
                245                 250

<210> SEQ ID NO 119
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 119
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta ccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggcttgc ccgtcatcga acgttggccc ggcatgcccg aataa                     765

<210> SEQ ID NO 120
<211> LENGTH: 254
<212> TYPE: PRT
<213> ORGANISM: Artificial Sequence
<220> FEATURE:
<223> OTHER INFORMATION: Variant of halohydrin dehalogenase from A.
``` radiobacter

<400> SEQUENCE: 120

```
Met Ser Thr Ala Ile Val Thr Asn Val Lys His Phe Gly Gly Met Gly
1               5                  10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65              70                  75                  80

Ile Ala Pro Val Glu Trp Arg Pro Ile Asp Lys Tyr Ala Val Glu Asp
            85                  90                  95

Tyr Arg Asp Thr Val Glu Ala Leu Gln Ile Lys Pro Phe Ala Leu Val
        100                 105                 110

Asn Ala Val Ala Ser Gln Met Lys Lys Arg Lys Ser Gly His Ile Ile
    115                 120                 125

Phe Ile Thr Ser Ala Ala Pro Phe Gly Pro Trp Lys Glu Leu Ser Thr
130             135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Leu Pro Val Ile Glu Arg Trp Pro Gly Met Pro Glu
                245                 250
```

<210> SEQ ID NO 121
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 121

| | |
|---|---|
| atgagcaccg ctattgtcac caacgtcaaa cattttgggg gtatgggtag cgctctgcgt | 60 |
| ctgagcgaag ctggtcatac cgtcgcttgc catgatgaaa gctttaagca tcaggatgaa | 120 |
| ctagaagctt ttgctgaaac ctacccacag ctgataccaa tgagcgaaca ggaaccagct | 180 |
| gaactgattg aagctgtcac cagcgctctt ggtcatgtcg atgtcctggt cagcaacgat | 240 |
| atcgcgcctg tggaatggcg gccaatcgat aaatacgctg tcgaggatta cagggatact | 300 |
| gtcgaagctc tgcagatcaa gccatttgct ctagtgaatg ctgtcgcttc gcaaatgaag | 360 |
| aagcgaaagt cggggcacat catcttcatc acttcggctg ccccgttcgg gccaatgaag | 420 |
| gagctatcga cttactcttc ggctcgagct ggggctagtg cactagctaa tgctctatcg | 480 |
| aaggagctag gagagtacaa tatcccggtg ttcgctatcg ctccgaatta cctacactcg | 540 |

```
gggattcgc cgtactatta cccctctgag ccgtggaaga cttctccgga gcacgtggct    600
cacgtgcgta aggtgactgc tctacaacga ctagggactc aaaaagagtt ggggaattg    660 gtgacgtttt tggcatctgg ctcttgtgat tatttgactg gccaggtgtt ttggttggca    720
ggcggctcgc ccgtcatcga acgttggccc ggcatgcccg aataa                   765
```

<210> SEQ ID NO 122
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 122

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Met Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Ser Pro Val Ile Glu Arg Trp Pro Gly Met Pro Glu
                245                 250
```

<210> SEQ ID NO 123
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 123

```
atgagcaccg ctattgtcac caacgtcaaa cattttggag gtatgggtag cgctctgcgt    60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag gagagtacaa tatcccggtg ttcgctatcg ctccgagtta cctacactcg    540
ggggattcgc cgtactatta cccctctgag ccgtggaaga cttctccgga gcacgtggct    600
cacgtgcgta aggtgactgc tctacaacga ctagggactc aaaaagagtt ggggggaattg    660 gtgacgtttt tggcatctgg ctcttgtgat tatttgactg gccaggtgtt ttggttggca    720
ggcggcttgc ccgtcatcga acgttggccc ggcatgcccg aataa                    765
```

<210> SEQ ID NO 124
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 124

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Ser
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

Gly Gly Leu Pro Val Ile Glu Arg Trp Pro Gly Met Pro Glu
            245                 250

<210> SEQ ID NO 125
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 125

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaacgaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta ccccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggcttgc ccgtcatcga acgttggccc ggcatgcccg aataa                      765
```

<210> SEQ ID NO 126
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 126

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Thr Lys Glu Leu Ser Thr
    130                 135                 140

Tyr Ser Ser Ala Arg Ala Gly Ala Ser Ala Leu Ala Asn Ala Leu Ser

```
                145                 150                 155                 160
Lys Glu Leu Gly Glu Tyr Asn Ile Pro Val Phe Ala Ile Ala Pro Asn
                    165                 170                 175

Tyr Leu His Ser Gly Asp Ser Pro Tyr Tyr Pro Ser Glu Pro Trp
                180                 185                 190

Lys Thr Ser Pro Glu His Val Ala His Val Arg Lys Val Thr Ala Leu
                195                 200                 205

Gln Arg Leu Gly Thr Gln Lys Glu Leu Gly Glu Leu Val Thr Phe Leu
                210                 215                 220

Ala Ser Gly Ser Cys Asp Tyr Leu Thr Gly Gln Val Phe Trp Leu Ala
225                 230                 235                 240

Gly Gly Leu Pro Val Ile Glu Arg Trp Pro Gly Met Pro Glu
                    245                 250

<210> SEQ ID NO 127
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 127
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatcgaag     420
gagctatcga cttactcttc ggctcgagct ggggctagtg cattagctaa tgctctatcg     480
aaggagctag agagtacaa tatcccggtg ttcgctatcg ctccggatta cctacactcg     540
ggggattcgc cgtactatta ccctctgag ccgtggaaga cttctccgga gcacgtggct     600
cacgtgcgta aggtgactgc tctacaacga ctagggactc aaaaagagtt ggggaattg     660 gtgacgtttt tggcatctgg ctcttgtgat tatttgactg gccaggtgtt ttggttggca     720
ggcggctttc ccgtcatcga acgttggccc ggcatgcccg aataa                     765

<210> SEQ ID NO 128
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 128

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
                20                  25                  30

Glu Ser Phe Lys His Gln Asp Glu Leu Glu Ala Phe Ala Glu Thr Tyr
            35                  40                  45

Pro Gln Leu Ile Pro Met Ser Glu Gln Glu Pro Ala Glu Leu Ile Glu
        50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Arg Lys Ser Gly His Ile Ile
        115                 120                 125

Phe Ile Thr Ser Ala Ala Pro Phe Gly Pro Ser Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asp
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Leu Gly Glu Leu Gly Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 129
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 129
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggtatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cgggacacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta cccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctcgc ccgtcatcga acgttggccc ggcatgcccg aataa                    765

<210> SEQ ID NO 130
<211> LENGTH: 254
<212> TYPE: PRT
<213> ORGANISM: Artificial Sequence
<220> FEATURE:
<223> OTHER INFORMATION: Variant of halohydrin dehalogenase from A.
``` radiobacter

<400> SEQUENCE: 130

| | | | | | | | | | | | | | | | |
|---|---|---|---|---|---|---|---|---|---|---|---|---|---|---|---|
|Met|Ser|Thr|Ala|Ile|Val|Thr|Asn|Val|Lys|His|Phe|Gly|Gly|Met|Gly|
|1| | | |5| | | |10| | | |15| | | |

| | | | | | | | | | | | | | | | |
|---|---|---|---|---|---|---|---|---|---|---|---|---|---|---|---|
|Ser|Ala|Leu|Arg|Leu|Ser|Glu|Ala|Gly|His|Thr|Val|Ala|Cys|His|Asp|
| | | |20| | | | |25| | | | |30| | |

| | | | | | | | | | | | | |
|---|---|---|---|---|---|---|---|---|---|---|---|---|
|Glu|Ser|Phe|Lys|His|Gln|Asp|Glu|Leu|Glu|Ala|Phe|Ala|Glu|Thr|Tyr|
| | | | |35| | | | |40| | | | |45| |

| | | | | | | | | | | | | | | | |
|---|---|---|---|---|---|---|---|---|---|---|---|---|---|---|---|
|Pro|Gln|Leu|Ile|Pro|Met|Ser|Glu|Gln|Glu|Pro|Ala|Glu|Leu|Ile|Glu|
| |50| | | | |55| | | | |60| | | | |

Ala Val Thr Ser Ala Leu Gly His Val Asp Val Leu Val Ser Asn Asp
65              70                  75                  80

Ile Ala Pro Val Val Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Ser Pro Val Ile Glu Arg Trp Pro Gly Met Pro Glu
                245                 250

<210> SEQ ID NO 131
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 131

| | |
|---|---|
|atgagcaccg ctattgtcac caacgtcaaa cattttggag gtatgggtag cgctctgcgt|60|
|ctgagcgaag ctggtcatac cgtcgcttgc catgatgaaa gctttaagca tcaggatgaa|120|
|ctagaagctt ttgctgaaac ctacccacag ctgataccaa tgagcgaaca ggaaccagct|180|
|gaactgattg aagctgtcac cagcgctctt ggtcatgtcg atgtcctggt cagcaacgat|240|
|atcgcgcctg tggaatggcg gccaatcgat aaatacgctg tcgaggatta caggaatact|300|
|gtcgaagctc tgcagatcaa gccatttgct ctagtgaatg ctgtcgcttc gcaaatgaag|360|
|aagcgaaagt cggggcacat catcttcatc acttcggctg ccccgttcgg gccaatgaag|420|
|gagctatcga cttactcttc ggctcgagct ggggctagtg cactagctaa tgctctatcg|480|
|aaggagctag gagagtacaa tatcccggtg ttcgctatcg ctccgaatta cctacactcg|540|

```
ggggattcgc cgtactatta ccctctgag ccgtggaaga cttctccgga gcacgtggct      600
cacgtgcgta aggtgactgc tctacaacga ctagggactc aaaaagagtt ggggaattg      660 gtgacgtttt tggcatctgg ctcttgtgat tatttgactg ccaggtgtt ttggttggca      720 ggcggctttc ccgtcatcga acgttggccc ggcatgcccg aataa                    765
```

<210> SEQ ID NO 132
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 132

```
Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
Ala Val Thr Ser Ala Leu Gly His Val Asp Leu Val Ser Asn Asp
65                  70                  75                  80
Ile Ala Pro Val Glu Trp Arg Pro Ile Asp Lys Tyr Ala Val Glu Asp
                85                  90                  95
Tyr Arg Asn Thr Val Glu Ala Leu Gln Ile Lys Pro Phe Ala Leu Val
            100                 105                 110
Asn Ala Val Ala Ser Gln Met Lys Lys Arg Lys Ser Gly His Ile Ile
        115                 120                 125
Phe Ile Thr Ser Ala Ala Pro Phe Gly Pro Met Lys Glu Leu Ser Thr
    130                 135                 140
Tyr Ser Ser Ala Arg Ala Gly Ala Ser Ala Leu Ala Asn Ala Leu Ser
145                 150                 155                 160
Lys Glu Leu Gly Glu Tyr Asn Ile Pro Val Phe Ala Ile Ala Pro Asn
                165                 170                 175
Tyr Leu His Ser Gly Asp Ser Pro Tyr Tyr Pro Ser Glu Pro Trp
            180                 185                 190
Lys Thr Ser Pro Glu His Val His Val Arg Lys Val Thr Ala Leu
                195                 200                 205
Gln Arg Leu Gly Thr Gln Lys Glu Leu Gly Glu Leu Val Thr Phe Leu
    210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                245                 250
```

<210> SEQ ID NO 133
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 133

```
atgagcaccg ctattgtcac caacgtcaaa cattttggag gtatgggtag cgctctgcgt      60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc gcttcggctg ccccgttcgg gccaacgaag    420
gagctatcga cttactcttc ggctcgagct ggggctagtg cactagctaa tgctctatcg    480
aaggagctag gagagtacaa tatcccggtg ttcgctatcg ctccggatta cctacactcg    540
ggggattcgc cgtactatta cccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctttc ccgtcatcga acgttggccc ggcatgcccg aataa                    765
```

<210> SEQ ID NO 134
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 134

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Ala Ser Ala Ala Pro Phe Gly Pro Thr Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asp
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

Gly Gly Phe Pro Val Ile Glu Arg Trp Pro Gly Met Pro Glu
                245                 250

<210> SEQ ID NO 135
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 135

```
atgagcaccg ctattgtcac caacgtcaaa cattttgggg gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatcgaag     420
gagctatcga cttactcttc ggctcgagct ggggctagtg cactagctaa tgctctatcg     480
aaggagctag gagagtacaa tatcccggtg ttcgctatcg ctccgaatta cctacactcg     540 gggattcgc cgtactatta ccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctcgc ccgtcatcga acgttggccc ggcatgcccg aataa                    765
```

<210> SEQ ID NO 136
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 136

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Ser Lys Glu Leu Ser Thr
    130                 135                 140

Tyr Ser Ser Ala Arg Ala Gly Ala Ser Ala Leu Ala Asn Ala Leu Ser

```
145                 150                 155                 160
Lys Glu Leu Gly Glu Tyr Asn Ile Pro Val Phe Ala Ile Ala Pro Asn
                165                 170                 175
Tyr Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
        195                 200                 205
Gln Arg Leu Gly Thr Gln Lys Glu Leu Gly Glu Leu Val Thr Phe Leu
    210                 215                 220
Ala Ser Gly Ser Cys Asp Tyr Leu Thr Gly Gln Val Phe Trp Leu Ala
225                 230                 235                 240
Gly Gly Ser Pro Val Ile Glu Arg Trp Pro Gly Met Pro Glu
                245                 250

<210> SEQ ID NO 137
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 137
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccaacgaag   420
gagctatcga cttactcttc ggctcgagct ggggctagtg cactagctaa tgctctatcg   480
aaggagctag agagtacaa tatcccggtg ttcgctatcg ctccgagtta cctacactcg   540
ggggattcgc cgtactatta ccctctgag ccgtggaaga cttctccgga gcacgtggct   600
cacgtgcgta aggtgactgc tctacaacga ctagggactc aaaaagagtt ggggaattg   660 gtgacgtttt tggcatctgg ctcttgtgat tatttgactg gccaggtgtt ttggttggca   720
ggcggctcgc ccgtcatcga acgttggccc ggcatgcccg aataa                  765

<210> SEQ ID NO 138
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 138

Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Thr Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Ser
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Ser Pro Val Ile Glu Arg Trp Pro Gly Met Pro Glu
                245                 250

<210> SEQ ID NO 139
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 139
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aggcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgactta cctacactcg     540
ggggattcgc cgtactatta ccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctcgc ccgtcatcga acgttggccc ggcatgcccg aataa                    765

<210> SEQ ID NO 140
<211> LENGTH: 254
<212> TYPE: PRT
<213> ORGANISM: Artificial Sequence
<220> FEATURE:
<223> OTHER INFORMATION: Variant of halohydrin dehalogenase from A.
``` radiobacter

<400> SEQUENCE: 140

```
Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
Ala Val Thr Ser Ala Leu Gly His Val Asp Val Leu Val Ser Asn Asp
65                  70                  75                  80
Ile Ala Pro Val Glu Trp Arg Pro Ile Asp Lys Tyr Ala Val Glu Asp
                85                  90                  95
Tyr Arg Asp Thr Val Glu Ala Leu Gln Ile Lys Pro Phe Ala Leu Val
            100                 105                 110
Asn Ala Val Ala Ser Gln Met Lys Arg Arg Lys Ser Gly His Ile Ile
        115                 120                 125
Phe Ile Thr Ser Ala Ala Pro Phe Gly Pro Trp Lys Glu Leu Ser Thr
    130                 135                 140
Tyr Ser Ser Ala Arg Ala Gly Ala Ser Ala Leu Ala Asn Ala Leu Ser
145                 150                 155                 160
Lys Glu Leu Gly Glu Tyr Asn Ile Pro Val Phe Ala Ile Ala Pro Thr
                165                 170                 175
Tyr Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
        195                 200                 205
Gln Arg Leu Gly Thr Gln Lys Glu Leu Gly Glu Leu Val Thr Phe Leu
    210                 215                 220
Ala Ser Gly Ser Cys Asp Tyr Leu Thr Gly Gln Val Phe Trp Leu Ala
225                 230                 235                 240
Gly Gly Ser Pro Val Ile Glu Arg Trp Pro Gly Met Pro Glu
                245                 250
```

<210> SEQ ID NO 141
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 141

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag gagagtacaa tatcccggtg ttcgctatcg ctccgactta cctacactcg     540
```

```
ggggattcgc cgtactatta ccsctctgag ccgtggaaga cttctccgga gcacgtggct    600
cacgtgcgta aggtgactgc tctacaacga ctagggactc aaaaagagtt ggggaattg     660 gtgacgtttt tggcatctgg ctcttgtgat tatttgactg gccaggtgtt ttggttggca    720
ggcggctttc ccgtcatcga acgttggccc ggcatgcccg aataa                   765
```

<210> SEQ ID NO 142
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 142

```
Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
Ala Val Thr Ser Ala Leu Gly His Val Asp Val Leu Val Ser Asn Asp
65                  70                  75                  80
Ile Ala Pro Val Glu Trp Arg Pro Ile Asp Lys Tyr Ala Val Glu Asp
                85                  90                  95
Tyr Arg Asp Thr Val Glu Ala Leu Gln Ile Lys Pro Phe Ala Leu Val
            100                 105                 110
Asn Ala Val Ala Ser Gln Met Lys Lys Arg Lys Ser Gly His Ile Ile
        115                 120                 125
Phe Ile Thr Ser Ala Ala Pro Phe Gly Pro Trp Lys Glu Leu Ser Thr
    130                 135                 140
Tyr Ser Ser Ala Arg Ala Gly Ala Ser Ala Leu Ala Asn Ala Leu Ser
145                 150                 155                 160
Lys Glu Leu Gly Glu Tyr Asn Ile Pro Val Phe Ala Ile Ala Pro Thr
                165                 170                 175
Tyr Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
        195                 200                 205
Gln Arg Leu Gly Thr Gln Lys Glu Leu Gly Glu Leu Val Thr Phe Leu
    210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                245                 250
```

<210> SEQ ID NO 143
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 143

```
atgagcaccg ctattgtcac caacgtcaaa cattttggag gtatgggtag cgctctgcgt    60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatcgaag    420
gagctatcga cttactcttc ggctcgagct ggggctagtg cactagctaa tgctctatcg    480
aaggagctag gagagtacaa tatcccggtg ttcgctatcg ctccgagtta cctacactcg    540
ggggattcgc cgtactatta cccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctcgc ccgtcatcga acgttggccc ggcatgcccg aataa                    765
```

<210> SEQ ID NO 144
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 144

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Ser Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Ser
                165                 170                 175

Tyr Leu His Ser Gly Asp Ser Pro Tyr Tyr Tyr Pro Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

Gly Gly Ser Pro Val Ile Glu Arg Trp Pro Gly Met Pro Glu
                245                 250

<210> SEQ ID NO 145
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 145

```
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccatcgaag   420
gagctatcga cttactcttc ggctcgagct ggggctagtg cactagctaa tgctctatcg   480
aaggagctag agagtacaa tatcccggtg ttcgctatcg ctccgagtta cctacactcg   540
ggggattcgc cgtactatta ccctctgag ccgtggaaga cttctccgga gcacgtggct   600
cacgtgcgta aggtgactgc tctacaacga ctagggactc aaaagagtt ggggaattg   660 gtgacgtttt tggcatctgg ctcttgtgat tatttgactg gccaggtgtt ttggttggca   720
ggcggctttc ccgtcatcga acgttggccc ggcatgcccg aataa              765
```

<210> SEQ ID NO 146
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 146

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Ser Lys Glu Leu Ser Thr
    130                 135                 140

Tyr Ser Ser Ala Arg Ala Gly Ala Ser Ala Leu Ala Asn Ala Leu Ser

```
145                 150                 155                 160
Lys Glu Leu Gly Glu Tyr Asn Ile Pro Val Phe Ala Ile Ala Pro Ser
                165                 170                 175
Tyr Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
                195                 200                 205
Gln Arg Leu Gly Thr Gln Lys Glu Leu Gly Glu Leu Val Thr Phe Leu
            210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                245                 250

<210> SEQ ID NO 147
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 147
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaatgaag     420
gagctatcga cttactcttc ggctcgagct ggggctagtg cactagctaa tgctctatcg     480
aaggagctag gagagtacaa tatcccggtg ttcgctatcg ctccgactta cctacactcg     540
ggggattcgc cgtactatta cccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                    765

<210> SEQ ID NO 148
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 148

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Arg Lys Ser Gly His Ile Ile
        115                 120                 125

Phe Ile Thr Ser Ala Ala Pro Phe Gly Pro Met Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Thr
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
            195                 200                 205

Gln Arg Leu Gly Thr Lys Glu Leu Gly Glu Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 149
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 149

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ccgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaatgaag     420
gagctatcga cttactcttc ggctcgagct ggggctagtg cactagctaa tgctctatcg     480
aaggagctag agagtacaa tatcccggtg ttcgctatcg ctccgactta cctacactcg     540
ggggattcgc cgtactatta cccctctgag ccgtggaaga cttctccgga gcacgtgact     600
cacgtgcgta aggtgactgc tctacaacga ctagggactc aaaaagagtt ggggaattg     660
gtgacgtttt tggcatctgg ctcttgtgat tatttgactg gccaggtgtt ttggttggca     720
ggcggctcgc ccgtcatcga acgttggccc ggcatgcccg aataa                    765
```

<210> SEQ ID NO 150
<211> LENGTH: 254
<212> TYPE: PRT
<213> ORGANISM: Artificial Sequence
<220> FEATURE:
<223> OTHER INFORMATION: Variant of halohydrin dehalogenase from A.

-continued radiobacter

<400> SEQUENCE: 150

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Pro Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Met Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Thr
                165                 170                 175

Tyr Leu His Ser Gly Asp Ser Pro Tyr Tyr Tyr Pro Ser Glu Pro Trp
            180                 185                 190

Lys Thr Ser Pro Glu His Val Thr His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Ser Pro Val Ile Glu Arg Trp Pro Gly Met Pro Glu
                245                 250

<210> SEQ ID NO 151
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 151
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat gaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgagtta cctacactcg     540

```
ggggattcgc cgtactatta ccctctgag ccgtggaaga cttctccgga gcacgtggct    600
cacgtgcgta aggtgactgc tctacaacga ctagggactc aaaaagagtt ggggaattg    660 gtgacgtttt tggcatctgg ctcttgtgat tattcgactg ccaggtgtt ttggttggca    720 ggcggctttc ccgtcatcga acgttggccc ggcatgcccg aataa                  765
```

<210> SEQ ID NO 152
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 152

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Leu Val Ser Asn Asp
65                  70                  75                  80

Ile Ala Pro Val Glu Trp Arg Pro Ile Asp Glu Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Ser
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Ser Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 153
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 153

```
atgagcaccg ctattgtcac caacgtcaaa cattttggag gtatgggtag cgctctgcgt    60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccaatgaag    420
gagctatcga cttactcttc ggctcgagct ggggctagtg cactagctaa tgctctatcg    480
aaggagctag gagagtacaa tatcccggtg ttcgctatcg ctccgagtta cctacactcg    540
ggggattcgc cgtactatta cccctctgag ccgtggaaga cttctccgga gcacgtggct    600
cacgtgcgta aggtgactgc tctacaacga ctagggactc aaaaagagtt ggggaattg    660 gtgacgtttt tggcatctgg ctcttgtgat tatttgactg gccaggtgtt ttggttggca    720
ggcggcttgc ccgtcatcga acgttggccc ggcatgcccg aataa                    765
```

<210> SEQ ID NO 154
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 154

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Met Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Ser
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

```
Gly Gly Leu Pro Val Ile Glu Arg Trp Pro Gly Met Pro Glu
                245                 250
```

<210> SEQ ID NO 155
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 155

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaatgaag     420
gagctatcga cttactcttc ggctcgagct ggggctagtg cactagctaa tgctctatcg     480
aaggagctag agagtacaa tatcccggtg ttcgctatcg ctccgagtta cctacactcg     540
ggggattcgc cgtactatta cccctctgag ccgtggaaga cttctccgga gcacgtggct     600
cgcgtgcgta gggtgactgc tctacaacga ctagggactc aaaaagagtt ggggaattg     660
gtgacgtttt tggcatctgg ctcttgtgat tatttgactg ccaggtgtt ttggttggca     720
ggcggctttc ccgtcatcga acgttggccc ggcatgcccg aataa                     765
```

<210> SEQ ID NO 156
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 156

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Met Lys Glu Leu Ser Thr
    130                 135                 140

Tyr Ser Ser Ala Arg Ala Gly Ala Ser Ala Leu Ala Asn Ala Leu Ser
```

```
               145                 150                 155                 160
Lys Glu Leu Gly Glu Tyr Asn Ile Pro Val Phe Ala Ile Ala Pro Ser
                    165                 170                 175

Tyr Leu His Ser Gly Asp Ser Pro Tyr Tyr Pro Ser Glu Pro Trp
            180                 185                 190

Lys Thr Ser Pro Glu His Val Ala Arg Val Arg Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 157
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 157
atgagcaccg ctattgtcac caacgtcaaa cattttggag gtatgggtag cgctctgcgt        60
ctgagcgaag ctggtcatac cgtcgcttgc catgatgaaa gctttaagca tcaggatgaa       120
ctagaagctt ttgctgaaac ctacccacag ctgataccaa tgagcgaaca ggaaccagct       180
gaactgattg aagctgtcac cagcgctctt ggtcatgtcg atgtcctggt cagcaacgat       240
atcgcgcctg tggaatggcg gccaatcgat aaatacgctg tcgaggatta cagggatact       300
gtcgaagctc tgcagatcaa gccatttgct ctagtgaatg ctgtcgcttc gcaaatgaag       360
aagcgaaagt cggggcacat catcttcatc acttcggctg ccccgttcgg gccatggaag       420
gagctatcga cttacccttc ggctcgagct ggggctagtg cactagctaa tgctctatcg       480
aaggagctag agagtacaaa tatcccggtg ttcgctatcg ctccgagtta cctacactcg       540
ggggattcgc cgtactatta cccctctgag ccgtggaaga cttctccgga gcacgtggct       600
cacgtgcgta aggtgactgc tctacaacga ctagggactc aaaaagagtt ggggaaattg       660
gtgacgtttt tggcatctgg ctcttgtgat tatttgactg gccaggtgtt ttggttggca       720
ggcggctcgc ccgtcatcga acgttggccc ggcatgcccg aataa                      765

<210> SEQ ID NO 158
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 158

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60
```

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
            85                  90                  95

Tyr Arg Asp Thr Val Glu Ala Leu Gln Ile Lys Pro Phe Ala Leu Val
        100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Pro Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Ser
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Glu Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Ser Pro Val Ile Glu Arg Trp Pro Gly Met Pro Glu
                245                 250

<210> SEQ ID NO 159
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 159
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccggatta cctacactcg     540
ggggattcgc cgtactatta cccctctgag ccgtggaaga cttctccgga gcacgtggct     600
cacgtgcgta aggtgactgc tctacaacga ctagggactc aaaaagagtt ggggaattg     660
gtgacgtttt tggcatctgg ctcttgtgat tatttgactg gccaggtgtt ttggttggca     720
ggcggctcgc ccgtcatcga acgttggccc ggcatgcccg aataa     765

<210> SEQ ID NO 160
<211> LENGTH: 254
<212> TYPE: PRT
<213> ORGANISM: Artificial Sequence
<220> FEATURE:
<223> OTHER INFORMATION: Variant of halohydrin dehalogenase from A.

radiobacter

<400> SEQUENCE: 160

| | | | | | | | | | | | | | | | |
|---|---|---|---|---|---|---|---|---|---|---|---|---|---|---|---|
|Met|Ser|Thr|Ala|Ile|Val|Thr|Asn|Val|Lys|His|Phe|Gly|Gly|Met|Gly|
|1| | | |5| | | | |10| | | | |15| |

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asp
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Ser Pro Val Ile Glu Arg Trp Pro Gly Met Pro Glu
                245                 250

<210> SEQ ID NO 161
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 161

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg ttgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaacgaag     420
gagctatcga cttactcttc ggctcgagct ggggctagtg cactagctaa tgctctatcg     480
aaggagctag gagagtacaa tatcccggtg ttcgctatcg ctccggatta cctacactcg     540
```

```
ggggattcgc cgtactatta cccctctgag ccgtggaaga cttctccgga gcacgtggct    600
cacgtgcgta aggtgactgc tctacaacga ctagggactc aaaaagagtt ggggaattg     660 gtgacgtttt tggcatctgg ctcttgtgat tatttgactg ccaggtgtt ttggttggca     720 ggcggctcgc ccgtcatcga acgttggccg ggcatgcccg aataa                    765
```

<210> SEQ ID NO 162
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 162

```
Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
Ala Val Thr Ser Ala Leu Gly His Val Asp Leu Val Ser Asn Asp
65                  70                  75                  80
Ile Ala Pro Val Glu Trp Arg Pro Ile Asp Lys Tyr Ala Val Glu Asp
                85                  90                  95
Tyr Arg Asp Thr Val Glu Ala Leu Gln Ile Lys Pro Phe Ala Leu Val
            100                 105                 110
Asn Ala Val Ala Ser Gln Met Lys Lys Arg Lys Ser Gly His Ile Ile
        115                 120                 125
Phe Ile Thr Ser Ala Ala Pro Phe Gly Pro Thr Lys Glu Leu Ser Thr
    130                 135                 140
Tyr Ser Ser Ala Arg Ala Gly Ala Ser Ala Leu Ala Asn Ala Leu Ser
145                 150                 155                 160
Lys Glu Leu Gly Glu Tyr Asn Ile Pro Val Phe Ala Ile Ala Pro Asp
                165                 170                 175
Tyr Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
        195                 200                 205
Gln Arg Leu Gly Thr Gln Lys Glu Leu Gly Glu Leu Val Thr Phe Leu
    210                 215                 220
Ala Ser Gly Ser Cys Asp Tyr Leu Thr Gly Gln Val Phe Trp Leu Ala
225                 230                 235                 240
Gly Gly Ser Pro Val Ile Glu Arg Trp Pro Gly Met Pro Glu
                245                 250
```

<210> SEQ ID NO 163
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 163

```
atgagcaccg ctattgtcac caacgtcaaa cattttggag gtatgggtag cgctctgcgt    60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccaatgaag    420
gagctatcga cttactcttc ggctcgagct ggggctagtg cactagctaa tgctctatcg    480
aaggagctag gagagtacaa tatcccggtg ttcgctatcg ctccggatta cctacactcg    540
ggggattcgc cgtactatta cccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctttc ccgtcatcga acgttggccc ggcatgcccg aataa                    765
```

<210> SEQ ID NO 164
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 164

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Met Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asp
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

Gly Gly Phe Pro Val Ile Glu Arg Trp Pro Gly Met Pro Glu
              245                 250

<210> SEQ ID NO 165
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 165

```
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg ccaacgaag    420
gagctatcga cttactcttc ggctcgagct ggggctagtg cactagctaa tgctctatcg   480
aaggagctag agagtacaa tatcccggtg ttcgctatcg ctccgaatta cctacacacg   540
ggggattcgc cgtactatta ccctctgag ccgtggaaga cttctccgga gcacgtggct   600
cacgtgcgta aggtgactgc tctacaacga ctagggactc aaaaagagtt gggggaattg   660
gtgacgtttt tggcatctgg ctcttgtgat tatttgactg ccaggtgtt ttggttggca    720
ggcggctcgc ccgtcatcga acgttggccc ggcatgcccg aataa                   765
```

<210> SEQ ID NO 166
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 166

Met Ser Thr Ala Ile Val Thr Asn Val Lys His Phe Gly Gly Met Gly
 1               5                  10                  15

Ser Ala Leu Arg Leu Ser Glu Ala Gly His Thr Val Ala Cys His Asp
             20                  25                  30

Glu Ser Phe Lys His Gln Asp Glu Leu Glu Ala Phe Ala Glu Thr Tyr
         35                  40                  45

Pro Gln Leu Ile Pro Met Ser Glu Gln Glu Pro Ala Glu Leu Ile Glu
     50                  55                  60

Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Thr Lys Glu Leu Ser Thr
    130                 135                 140

Tyr Ser Ser Ala Arg Ala Gly Ala Ser Ala Leu Ala Asn Ala Leu Ser

```
                145                 150                 155                 160
Lys Glu Leu Gly Glu Tyr Asn Ile Pro Val Phe Ala Ile Ala Pro Asn
                    165                 170                 175

Tyr Leu His Thr Gly Asp Ser Pro Tyr Tyr Pro Ser Glu Pro Trp
                180                 185                 190

Lys Thr Ser Pro Glu His Val Ala His Val Arg Lys Val Thr Ala Leu
            195                 200                 205

Gln Arg Leu Gly Thr Gln Lys Glu Leu Gly Glu Leu Val Thr Phe Leu
        210                 215                 220

Ala Ser Gly Ser Cys Asp Tyr Leu Thr Gly Gln Val Phe Trp Leu Ala
225                 230                 235                 240

Gly Gly Ser Pro Val Ile Glu Arg Trp Pro Gly Met Pro Glu
                    245                 250

<210> SEQ ID NO 167
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 167
atgagcaccg ctattgtcac caacgtcaaa catttTggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatcgaag     420
gagctatcga cttactcttc ggctcgagct ggggctagtg cactagctaa tgctctatcg     480
aaggagctag gagagtacaa tatcccggtg ttcgctatcg ctccggatta cctacactcg     540
ggggattcgc cgtactatta cccctctgag ccgtggaaga cttctccgga gcacgtggct     600
cacgtgcgta aggtgactgc tctacaacga ctagggactc aaaaagagtt ggggaattg     660 gtgacgtttt tggcatctgg ctcttgtgat tatttgactg gccaggtgtt ttggttggca     720
ggcggctcgc ccgtcatcga acgttggccc ggcatgcccg aataa                    765

<210> SEQ ID NO 168
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 168

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Ser Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asp
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Glu Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Ser Pro Val Ile Glu Arg Trp Pro Gly Met Pro Glu
                245                 250

<210> SEQ ID NO 169
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 169
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaatgaag     420
gagctatcga cttactcttc ggctcgagct ggggctagtg cactagctaa tgctctatcg     480
aaggagctag gagagtacaa tatcccggtg ttcgctatcg ctccggatta cctacactcg     540
ggggattcgc cgtaccatta cccctctgag ccgtggaaga cttctccgga gcacgtggct     600
cacgtgcgta aggtgactgc tctacaacga ctagggactc aaaaagagtt ggggggaattg     660
gtgacgtttt tggcatctgg ctcttgtgat tatttgactg gccaggtgtt ttggttggca     720
ggcggcttgc ccgtcatcga acgttggccc ggcatgcccg aataa                    765

<210> SEQ ID NO 170
<211> LENGTH: 254
<212> TYPE: PRT
<213> ORGANISM: Artificial Sequence
<220> FEATURE:
<223> OTHER INFORMATION: Variant of halohydrin dehalogenase from A.
``` radiobacter

<400> SEQUENCE: 170

| | | | | | | | | | | | | | | | |
|---|---|---|---|---|---|---|---|---|---|---|---|---|---|---|---|
| Met | Ser | Thr | Ala | Ile | Val | Thr | Asn | Val | Lys | His | Phe | Gly | Gly | Met | Gly |
| 1 | | | | 5 | | | | | 10 | | | | | 15 | |

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Met Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asp
                165                 170                 175

Tyr Leu His Ser Gly Asp Ser Pro Tyr His Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Leu Pro Val Ile Glu Arg Trp Pro Gly Met Pro Glu
                245                 250

<210> SEQ ID NO 171
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 171

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaatgaag     420
gagctatcga cttactcttc ggctcgagct ggggctagtg cactagctaa tgctctatcg     480
aaggagctag gagagtacaa tatcccggtg ttcgctatcg ctccggatta cctacactcg     540
```

```
ggggattcgc cgtactatta ccctctgag ccgtggaaga cttctccgga gcacgtggct    600
cacgtgcgta aggtgactgc tctacaacga ctagggactc aaaaagagtt ggggaattg    660 gtgacgtttt tggcatctgg ctcttgtgat tatttgactg gccaggtgtt ttggttggca    720
ggcggctcgc ccgtcatcga acgttggccc ggcatgcccg aataa                   765
```

<210> SEQ ID NO 172
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 172

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Met Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asp
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Ser Pro Val Ile Glu Arg Trp Pro Gly Met Pro Glu
                245                 250
```

<210> SEQ ID NO 173
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 173

```
atgagcaccg ctattgtcac caacgtcaaa cattttggag gtatgggtag cgctctgcgt    60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
tttgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag gagagtacaa tatcccggtg ttcgctatcg ctccgaatta cctacactcg    540
ggggattcgc cgtactatta cccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctttc ccgtcatcga acgttggccc ggcatgcccg aataa              765
```

<210> SEQ ID NO 174
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 174

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Phe Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

-continued

```
Gly Gly Phe Pro Val Ile Glu Arg Trp Pro Gly Met Pro Glu
                245                 250
```

<210> SEQ ID NO 175
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 175

```
atgagcaccg ctattgtcac caacgtcaaa catttggag gtatgggtag cgctctgcgt      60
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atctgccctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag agagtacaa tatcccggtg ttcgctatcg ctccgaatta cctacactcg    540
ggggattcgc cgtactatta ccccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg ccaggtgtt ttggttggca    720
ggcggctttc ccgtcatcga acgttggccc ggcatgcccg aataa                    765
```

<210> SEQ ID NO 176
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 176

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Cys Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
```

```
145                 150                 155                 160
Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
                195                 200                 205

Gln Arg Leu Gly Thr Gln Lys Glu Leu Gly Glu Leu Val Thr Phe Leu
            210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 177
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 177

```
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atctttcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccatggaag   420
gagctatcga cttactcttc ggctcgagct ggggctagtg cactagctaa tgctctatcg   480
aaggagctag gagagtacaa tatcccggtg ttcgctatcg ctccgaatta cctacactcg   540
ggggattcgc cgtactatta ccccctctgag ccgtggaaga cttctccgga gcacgtggct   600
cacgtgcgta aggtgactgc tctacaacga ctagggactc aaaaagagtt ggggaattg   660
gtgacgtttt tggcatctgg ctcttgtgat tatttgactg gccaggtgtt ttggttggca   720
ggcggctttc ccgtcatcga acgttggccc ggcatgcccg aataa              765
```

<210> SEQ ID NO 178
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 178

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60
```

-continued

```
Ala Val Thr Ser Ala Leu Gly His Val Asp Val Leu Val Ser Asn Asp
 65                  70                  75                  80

Ile Phe Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 179
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 179

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcggccctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta ccctctgag ccgtggaaga cttctccgga gcacgtggct     600
cacgtgcgta aggtgactgc tctacaacga ctagggactc aaaaagagtt ggggaattg      660
gtgacgtttt tggcatctgg ctcttgtgat tatttgactg gccaggtgtt ttggttggca     720
ggcggctttc ccgtcatcga acgttggccc ggcatgcccg aataa                      765
```

<210> SEQ ID NO 180
<211> LENGTH: 254
<212> TYPE: PRT
<213> ORGANISM: Artificial Sequence
<220> FEATURE:
<223> OTHER INFORMATION: Variant of halohydrin dehalogenase from A.

radiobacter

<400> SEQUENCE: 180

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65              70                  75                  80

Ile Gly Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 181
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 181

| | |
|---|---|
| atgagcaccg ctattgtcac caacgtcaaa cattttggag gtatgggtag cgctctgcgt | 60 |
| ctgagcgaag ctggtcatac cgtcgcttgc catgatgaaa gctttaagca tcaggatgaa | 120 |
| ctagaagctt ttgctgaaac ctacccacag ctgataccaa tgagcgaaca ggaaccagct | 180 |
| gaactgattg aagctgtcac cagcgctctt ggtcatgtcg atgtcctggt cagcaacgat | 240 |
| atcctgcctg tggaatggcg gccaatcgat aaatacgctg tcgaggatta cagggatact | 300 |
| gtcgaagctc tgcagatcaa gccatttgct ctagtgaatg ctgtcgcttc gcaaatgaag | 360 |
| aagcgaaagt cggggcacat catcttcatc acttcggctg ccccgttcgg gccatggaag | 420 |
| gagctatcga cttactcttc ggctcgagct ggggctagtg cactagctaa tgctctatcg | 480 |
| aaggagctag gagagtacaa tatcccggtg ttcgctatcg ctccgaatta cctacactcg | 540 |

```
ggggattcgc cgtactatta cccctctgag ccgtggaaga cttctccgga gcacgtggct    600
cacgtgcgta aggtgactgc tctacaacga ctagggactc aaaaagagtt ggggaattg     660 gtgacgtttt tggcatctgg ctcttgtgat tatttgactg gccaggtgtt ttggttggca    720
ggcggctttc ccgtcatcga acgttggccc ggcatgcccg aataa                    765
```

<210> SEQ ID NO 182
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 182

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Leu Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 183
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 183

```
atgagcaccg ctattgtcac caacgtcaaa cattttggag gtatgggtag cgctctgcgt    60
```

```
ctgagcgaag ctggtcatac cgtcgcttgc catgatgaaa gctttaagca tcaggatgaa      120
ctagaagctt ttgctgaaac ctacccacag ctgataccaa tgagcgaaca ggaaccagct      180
gaactgattg aagctgtcac cagcgctctt ggtcatgtcg atgtcctggt cagcaacgat      240
atcagccctg tggaatggcg gccaatcgat aaatacgctg tcgaggatta cagggatact      300
gtcgaagctc tgcagatcaa gccatttgct ctagtgaatg ctgtcgcttc gcaaatgaag      360
aagcgaaagt cggggcacat catcttcatc acttcggctg ccccgttcgg gccatggaag      420
gagctatcga cttactcttc ggctcgagct ggggctagtg cactagctaa tgctctatcg      480
aaggagctag gagagtacaa tatcccggtg ttcgctatcg ctccgaatta cctacactcg      540
ggggattcgc cgtactatta cccctctgag ccgtggaaga cttctccgga gcacgtggct      600
cacgtgcgta aggtgactgc tctacaacga ctagggactc aaaaagagtt gggggaattg      660
gtgacgtttt tggcatctgg ctcttgtgat tatttgactg gccaggtgtt ttggttggca      720
ggcggctttc ccgtcatcga acgttggccc ggcatgcccg aataa                     765
```

<210> SEQ ID NO 184
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 184

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ser Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

```
Gly Gly Phe Pro Val Ile Glu Arg Trp Pro Gly Met Pro Glu
                245                 250
```

<210> SEQ ID NO 185
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 185

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atctatcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgaatta cctacactcg      540
ggggattcgc cgtactatta cccctctgag ccgtggaaga cttctccgga gcacgtggct     600
cacgtgcgta aggtgactgc tctacaacga ctagggactc aaaagagtt gggggaattg      660
gtgacgtttt tggcatctgg ctcttgtgat tatttgactg gccaggtgtt ttggttggca     720
ggcggctttc ccgtcatcga acgttggccc ggcatgcccg aataa                    765
```

<210> SEQ ID NO 186
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 186

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Tyr Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
```

```
                145                 150                 155                 160
Lys Glu Leu Gly Glu Tyr Asn Ile Pro Val Phe Ala Ile Ala Pro Asn
                    165                 170                 175
Tyr Leu His Ser Gly Asp Ser Pro Tyr Tyr Pro Ser Glu Pro Trp
                180                 185                 190
Lys Thr Ser Pro Glu His Val Ala His Val Arg Lys Val Thr Ala Leu
                    195                 200                 205
Gln Arg Leu Gly Thr Gln Lys Glu Leu Gly Glu Leu Val Thr Phe Leu
                210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                    245                 250

<210> SEQ ID NO 187
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 187
atgagcaccg ctattgtcac caacgtcaaa cattttggag gtatgggtag cgctctgcgt       60
ctgagcgaag ctggtcatac cgtcgcttgc catgatgaaa gctttaagca tcaggatgaa      120
ctagaagctt ttgctgaaac ctacccacag ctgataccaa tgagcgaaca ggaaccagct      180
gaactgattg aagctgtcac cagcgctctt ggtcatgtcg atgtcctggt cagcaacgat      240
atcgcgtgcg tggaatggcg gccaatcgat aaatacgctg tcgaggatta cagggatact      300
gtcgaagctc tgcagatcaa gccatttgct ctagtgaatg ctgtcgcttc gcaaatgaag      360
aagcgaaagt cggggcacat catcttcatc acttcggctg ccccgttcgg gccatggaag      420
gagctatcga cttactcttc ggctcgagct ggggctagtg cactagctaa tgctctatcg      480
aaggagctag gagagtacaa tatcccggtg ttcgctatcg ctccgaatta cctacactcg      540
ggggattcgc cgtactatta ccctctgag ccgtggaaga cttctccgga gcacgtggct      600
cacgtgcgta aggtgactgc tctacaacga ctagggactc aaaaagagtt ggggaattg       660
gtgacgtttt tggcatctgg ctcttgtgat tatttgactg gccaggtgtt ttggttggca      720
ggcggctttc ccgtcatcga acgttggccc ggcatgcccg aataa                      765

<210> SEQ ID NO 188
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 188

Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
                20                  25                  30
Glu Ser Phe Lys His Gln Asp Glu Leu Glu Ala Phe Ala Glu Thr Tyr
            35                  40                  45
Pro Gln Leu Ile Pro Met Ser Glu Gln Glu Pro Ala Glu Leu Ile Glu
        50                  55                  60
```

```
Ala Val Thr Ser Ala Leu Gly His Val Asp Val Leu Val Ser Asn Asp
 65                  70                  75                  80

Ile Ala Cys Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
            195                 200                 205

Gln Arg Leu Gly Thr Lys Glu Leu Gly Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 189
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 189

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcggaag tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta ccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                    765
```

<210> SEQ ID NO 190
<211> LENGTH: 254
<212> TYPE: PRT
<213> ORGANISM: Artificial Sequence
<220> FEATURE:
<223> OTHER INFORMATION: Variant of halohydrin dehalogenase from A.

radiobacter

<400> SEQUENCE: 190

| Met | Ser | Thr | Ala | Ile | Val | Thr | Asn | Val | Lys | His | Phe | Gly | Gly | Met | Gly |
|---|---|---|---|---|---|---|---|---|---|---|---|---|---|---|---|
| 1 | | | | 5 | | | | | 10 | | | | | 15 | |

| Ser | Ala | Leu | Arg | Leu | Ser | Glu | Ala | Gly | His | Thr | Val | Ala | Cys | His | Asp |
|---|---|---|---|---|---|---|---|---|---|---|---|---|---|---|---|
| | | | 20 | | | | | 25 | | | | | 30 | | |

| Glu | Ser | Phe | Lys | His | Gln | Asp | Glu | Leu | Glu | Ala | Phe | Ala | Glu | Thr | Tyr |
|---|---|---|---|---|---|---|---|---|---|---|---|---|---|---|---|
| | | | | 35 | | | | | 40 | | | | | 45 | |

| Pro | Gln | Leu | Ile | Pro | Met | Ser | Glu | Gln | Glu | Pro | Ala | Glu | Leu | Ile | Glu |
|---|---|---|---|---|---|---|---|---|---|---|---|---|---|---|---|
| | 50 | | | | | 55 | | | | | 60 | | | | |

| Ala | Val | Thr | Ser | Ala | Leu | Gly | His | Val | Asp | Val | Leu | Val | Ser | Asn | Asp |
|---|---|---|---|---|---|---|---|---|---|---|---|---|---|---|---|
| 65 | | | | | 70 | | | | | 75 | | | | | 80 |

| Ile | Ala | Glu | Val | Glu | Trp | Arg | Pro | Ile | Asp | Lys | Tyr | Ala | Val | Glu | Asp |
|---|---|---|---|---|---|---|---|---|---|---|---|---|---|---|---|
| | | | | 85 | | | | | 90 | | | | | 95 | |

| Tyr | Arg | Asp | Thr | Val | Glu | Ala | Leu | Gln | Ile | Lys | Pro | Phe | Ala | Leu | Val |
|---|---|---|---|---|---|---|---|---|---|---|---|---|---|---|---|
| | | | 100 | | | | | 105 | | | | | 110 | | |

| Asn | Ala | Val | Ala | Ser | Gln | Met | Lys | Lys | Arg | Lys | Ser | Gly | His | Ile | Ile |
|---|---|---|---|---|---|---|---|---|---|---|---|---|---|---|---|
| | | 115 | | | | | 120 | | | | | 125 | | | |

| Phe | Ile | Thr | Ser | Ala | Ala | Pro | Phe | Gly | Pro | Trp | Lys | Glu | Leu | Ser | Thr |
|---|---|---|---|---|---|---|---|---|---|---|---|---|---|---|---|
| 130 | | | | | 135 | | | | | 140 | | | | | |

| Tyr | Ser | Ser | Ala | Arg | Ala | Gly | Ala | Ser | Ala | Leu | Ala | Asn | Ala | Leu | Ser |
|---|---|---|---|---|---|---|---|---|---|---|---|---|---|---|---|
| 145 | | | | | 150 | | | | | 155 | | | | | 160 |

| Lys | Glu | Leu | Gly | Glu | Tyr | Asn | Ile | Pro | Val | Phe | Ala | Ile | Ala | Pro | Asn |
|---|---|---|---|---|---|---|---|---|---|---|---|---|---|---|---|
| | | | | 165 | | | | | 170 | | | | | 175 | |

| Tyr | Leu | His | Ser | Gly | Asp | Ser | Pro | Tyr | Tyr | Tyr | Pro | Ser | Glu | Pro | Trp |
|---|---|---|---|---|---|---|---|---|---|---|---|---|---|---|---|
| | | | 180 | | | | | 185 | | | | | 190 | | |

| Lys | Thr | Ser | Pro | Glu | His | Val | Ala | His | Val | Arg | Lys | Val | Thr | Ala | Leu |
|---|---|---|---|---|---|---|---|---|---|---|---|---|---|---|---|
| | | | 195 | | | | | 200 | | | | | 205 | | |

| Gln | Arg | Leu | Gly | Thr | Gln | Lys | Glu | Leu | Gly | Glu | Leu | Val | Thr | Phe | Leu |
|---|---|---|---|---|---|---|---|---|---|---|---|---|---|---|---|
| | 210 | | | | | 215 | | | | | 220 | | | | |

| Ala | Ser | Gly | Ser | Cys | Asp | Tyr | Leu | Thr | Gly | Gln | Val | Phe | Trp | Leu | Ala |
|---|---|---|---|---|---|---|---|---|---|---|---|---|---|---|---|
| 225 | | | | | 230 | | | | | 235 | | | | | 240 |

| Gly | Gly | Phe | Pro | Val | Ile | Glu | Arg | Trp | Pro | Gly | Met | Pro | Glu | | |
|---|---|---|---|---|---|---|---|---|---|---|---|---|---|---|---|
| | | | | 245 | | | | | 250 | | | | | | |

<210> SEQ ID NO 191
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 191

| atgagcaccg ctattgtcac caacgtcaaa cattttggag gtatgggtag cgctctgcgt | 60 |
|---|---|
| ctgagcgaag ctggtcatac cgtcgcttgc catgatgaaa gctttaagca tcaggatgaa | 120 |
| ctagaagctt ttgctgaaac ctacccacag ctgataccaa tgagcgaaca ggaaccagct | 180 |
| gaactgattg aagctgtcac cagcgctctt ggtcatgtcg atgtcctggt cagcaacgat | 240 |
| atcgcgcctg tggaagcgcg gccaatcgat aaatacgctg tcgaggatta cagggatact | 300 |
| gtcgaagctc tgcagatcaa gccatttgct ctagtgaatg ctgtcgcttc gcaaatgaag | 360 |
| aagcgaaagt cggggcacat catcttcatc acttcggctg ccccgttcgg gccatggaag | 420 |
| gagctatcga cttactcttc ggctcgagct ggggctagtg cactagctaa tgctctatcg | 480 |
| aaggagctag gagagtacaa tatcccggtg ttcgctatcg ctccgaatta cctacactcg | 540 |

```
ggggattcgc cgtactatta cccctctgag ccgtggaaga cttctccgga gcacgtggct      600
cacgtgcgta aggtgactgc tctacaacga ctagggactc aaaaagagtt gggggaattg      660
gtgacgtttt tggcatctgg ctcttgtgat tatttgactg gccaggtgtt ttggttggca      720
ggcggctttc ccgtcatcga acgttggccc ggcatgcccg aataa                     765
```

<210> SEQ ID NO 192
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 192

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Leu Val Ser Asn Asp
65                  70                  75                  80

Ile Ala Pro Val Glu Ala Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 193
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 193

```
atgagcaccg ctattgtcac caacgtcaaa cattttggag gtatgggtag cgctctgcgt      60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
gaagcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag gagagtacaa tatcccggtg ttcgctatcg ctccgaatta cctacactcg    540
ggggattcgc cgtactatta cccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctttc ccgtcatcga acgttggccc ggcatgcccg aataa                    765
```

<210> SEQ ID NO 194
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 194

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Glu Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

Gly Gly Phe Pro Val Ile Glu Arg Trp Pro Gly Met Pro Glu
                245                 250

<210> SEQ ID NO 195
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 195

```
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atggcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccatggaag   420
gagctatcga cttactcttc ggctcgagct ggggctagtg cactagctaa tgctctatcg   480
aaggagctag agagtacaa tatcccggtg ttcgctatcg ctccgaatta cctacactcg   540
ggggattcgc cgtactatta ccccctctgag ccgtggaaga cttctccgga gcacgtggct   600
cacgtgcgta aggtgactgc tctacaacga ctagggactc aaaaagagtt gggggaattg   660
gtgacgtttt tggcatctgg ctcttgtgat tatttgactg ccaggtgtt ttggttggca   720
ggcggctttc ccgtcatcga acgttggccc ggcatgcccg aataa              765
```

<210> SEQ ID NO 196
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 196

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Met Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser

```
                145                 150                 155                 160
Lys Glu Leu Gly Glu Tyr Asn Ile Pro Val Phe Ala Ile Ala Pro Asn
                    165                 170                 175
Tyr Leu His Ser Gly Asp Ser Pro Tyr Tyr Pro Ser Glu Pro Trp
                180                 185                 190
Lys Thr Ser Pro Glu His Val Ala His Val Arg Lys Val Thr Ala Leu
                195                 200                 205
Gln Arg Leu Gly Thr Gln Lys Glu Leu Gly Glu Leu Val Thr Phe Leu
        210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                    245                 250

<210> SEQ ID NO 197
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 197
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
tgggcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa atcccggtg ttcgctatcg ctccgaatta cctacactcg      540
ggggattcgc cgtactatta ccctctgag ccgtggaaga cttctccgga gcacgtggct      600
cacgtgcgta aggtgactgc tctacaacga ctagggactc aaaaagagtt ggggaattg      660 gtgacgtttt tggcatctgg ctcttgtgat tatttgactg gccaggtgtt ttggttggca     720
ggcggctttc ccgtcatcga acgttggccc ggcatgcccg aataa                    765

<210> SEQ ID NO 198
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 198

Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Trp Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Leu Glu Leu Gly Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 199
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 199
atgagcaccg ctattgtcac caacgtcaaa cattttggag gtatgggtag cgctctgcgt        60
ctgagcgaag ctggtcatac cgtcgcttgc catgatgaaa gctttaagca tcaggatgaa       120
ctagaagctt ttgctgaaac ctacccacaa ctgataccaa tgagcgaaca ggaaccagct       180
gaactgattg aagctgtcac cagcgctctt ggtcatgtcg atgtcctggt cagcaacgat       240
tatgcgcctg tggaatggcg gccaatcgat aaatacgctg tcgaggatta cagggatact       300
gtcgaagctc tgcagatcaa gccatttgct ctagtgaatg ctgtcgcttc gcaaatgaag       360
aagcgaaagt cggggcacat catcttcatc acttcggctg ccccgttcgg gccatggaag       420
gagctatcga cttactcttc ggctcgagct ggggctagtg cactagctaa tgctctatcg       480
aaggagctag agagtacaa tatcccggtg ttcgctatcg ctccgaatta cctacactcg       540
ggggattcgc cgtactatta ccctctgag ccgtggaaga cttctccgga gcacgtggct       600
cacgtgcgta aggtgactgc tctacaacga ctagggactc aaaaagagtt gggggaattg       660
gtgacgtttt tggcatctgg ctcttgtgat tatttgactg gccaggtgtt ttggttggca       720
ggcggctttc ccgtcatcga acgttggccc ggcatgcccg aataa                      765

<210> SEQ ID NO 200
<211> LENGTH: 254
<212> TYPE: PRT
<213> ORGANISM: Artificial Sequence
<220> FEATURE:
<223> OTHER INFORMATION: Variant of halohydrin dehalogenase from A.
``` radiobacter

<400> SEQUENCE: 200

| | | | | | | | | | | | | | | | |
|---|---|---|---|---|---|---|---|---|---|---|---|---|---|---|---|
| Met | Ser | Thr | Ala | Ile | Val | Thr | Asn | Val | Lys | His | Phe | Gly | Gly | Met | Gly |
| 1 | | | | 5 | | | | | 10 | | | | | 15 | |

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
            35                  40                  45

Pro Gln Leu Ile Pro Met Ser Glu Gln Glu Pro Ala Glu Leu Ile Glu
            50                  55                  60

Ala Val Thr Ser Ala Leu Gly His Val Asp Val Leu Val Ser Asn Asp
65                  70                  75                  80

Tyr Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
            115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
            195                 200                 205

Gln Arg Leu Gly Thr Gln Lys Glu Leu Gly Glu Leu Val Thr Phe Leu
            210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 201
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 201

| | |
|---|---|
| atgagcaccg ctattgtcac caacgtcaaa cattttggag gtatgggtag cgctctgcgt | 60 |
| ctgagcgaag ctggtcatac cgtcgcttgc catgatgaaa gctttaagca tcaggatgaa | 120 |
| ctagaagctt ttgctgaaac ctacccacag ctgataccaa tgagcgaaca ggaaccagct | 180 |
| gaactgattg aagctgtcac cagcgctctt ggtcatgtcg atgtcctggt cagcaacgat | 240 |
| atcattcctg tggaatggcg gccaatcgat aaatacgctg tcgaggatta cagggatact | 300 |
| gtcgaagctc tgcagatcaa gccatttgct ctagtgaatg ctgtcgcttc gcaaatgaag | 360 |
| aagcgaaagt cggggcacat catcttcatc acttcggctg ccccgttcgg gccatggaag | 420 |
| gagctatcga cttactcttc ggctcgagct ggggctagtg cactagctaa tgctctatcg | 480 |
| aaggagctag gagagtacaa tatcccggtg ttcgctatcg ctccgaatta cctacactcg | 540 |

```
ggggattcgc cgtactatta ccctctgag ccgtggaaga cttctccgga gcacgtggct      600
cacgtgcgta aggtgactgc tctacaacga ctagggactc aaaaagagtt ggggaattg      660 gtgacgtttt tggcatctgg ctcttgtgat tatttgactg ccaggtgtt ttggttggca      720 ggcggctttc ccgtcatcga acgttggccc ggcatgcccg aataa                    765
```

<210> SEQ ID NO 202
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 202

```
Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
Ala Val Thr Ser Ala Leu Gly His Val Asp Leu Val Ser Asn Asp
65                  70                  75                  80
Ile Ile Pro Val Glu Trp Arg Pro Ile Asp Lys Tyr Ala Val Glu Asp
                85                  90                  95
Tyr Arg Asp Thr Val Glu Ala Leu Gln Ile Lys Pro Phe Ala Leu Val
            100                 105                 110
Asn Ala Val Ala Ser Gln Met Lys Lys Arg Lys Ser Gly His Ile Ile
        115                 120                 125
Phe Ile Thr Ser Ala Ala Pro Phe Gly Pro Trp Lys Glu Leu Ser Thr
    130                 135                 140
Tyr Ser Ser Ala Arg Ala Gly Ala Ser Ala Leu Ala Asn Ala Leu Ser
145                 150                 155                 160
Lys Glu Leu Gly Glu Tyr Asn Ile Pro Val Phe Ala Ile Ala Pro Asn
                165                 170                 175
Tyr Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
        195                 200                 205
Gln Arg Leu Gly Thr Gln Lys Glu Leu Gly Glu Leu Val Thr Phe Leu
    210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                245                 250
```

<210> SEQ ID NO 203
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 203

```
atgagcaccg ctattgtcac caacgtcaaa cattttggag gtatgggtag cgctctgcgt      60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcaaacctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag gagagtacaa tatcccggtg ttcgctatcg ctccgaatta cctacactcg    540
ggggattcgc cgtactatta cccctctgag ccgtggaaga cttctccgga gcacgtggct    600
cacgtgcgta aggtgactgc tctacaacga ctagggactc aaaaagagtt ggggaattg     660 gtgacgtttt tggcatctgg ctcttgtgat tatttgactg gccaggtgtt ttggttggca    720
ggcggctttc ccgtcatcga acgttggccc ggcatgcccg aataa                     765
```

<210> SEQ ID NO 204
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 204

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Lys Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

Gly Gly Phe Pro Val Ile Glu Arg Trp Pro Gly Met Pro Glu
            245                 250

<210> SEQ ID NO 205
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 205
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcatgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccatggaag   420
gagctatcga cttactcttc ggctcgagct ggggctagtg cactagctaa tgctctatcg   480
aaggagctag agagtacaa tatcccggtg ttcgctatcg ctccgaatta cctacactcg   540
ggggattcgc cgtactatta cccctctgag ccgtggaaga cttctccgga gcacgtggct   600
cacgtgcgta aggtgactgc tctacaacga ctagggactc aaaaagagtt ggggaattg   660 gtgacgtttt tggcatctgg ctcttgtgat tatttgactg ccaggtgtt ttggttggca   720 ggcggctttc ccgtcatcga acgttggccc ggcatgcccg aataa              765

<210> SEQ ID NO 206
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 206

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Met Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser

```
                145                 150                 155                 160
Lys Glu Leu Gly Glu Tyr Asn Ile Pro Val Phe Ala Ile Ala Pro Asn
                    165                 170                 175

Tyr Leu His Ser Gly Asp Ser Pro Tyr Tyr Pro Ser Glu Pro Trp
                180                 185                 190

Lys Thr Ser Pro Glu His Val Ala His Val Arg Lys Val Thr Ala Leu
                    195                 200                 205

Gln Arg Leu Gly Thr Gln Lys Glu Leu Gly Glu Leu Val Thr Phe Leu
                    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                    245                 250

<210> SEQ ID NO 207
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 207
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg atgaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccatggaag   420
gagctatcga cttactcttc ggctcgagct ggggctagtg cactagctaa tgctctatcg   480
aaggagctag agagtacaa tatcccggtg ttcgctatcg ctccgaatta cctacactcg   540
ggggattcgc cgtactatta cccctctgag ccgtggaaga cttctccgga gcacgtggct   600
cacgtgcgta aggtgactgc tctacaacga ctagggactc aaaaagagtt ggggaaattg   660
gtgacgtttt tggcatctgg ctcttgtgat tatttgactg gccaggtgtt ttggttggca   720
ggcggctttc ccgtcatcga acgttggccc ggcatgcccg aataa              765

<210> SEQ ID NO 208
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 208

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
                20                  25                  30

Glu Ser Phe Lys His Gln Asp Glu Leu Glu Ala Phe Ala Glu Thr Tyr
            35                  40                  45

Pro Gln Leu Ile Pro Met Ser Glu Gln Glu Pro Ala Glu Leu Ile Glu
        50                  55                  60
```

Ala Val Thr Ser Ala Leu Gly His Val Asp Val Leu Val Ser Asn Asp
65                  70                  75                  80

Ile Ala Pro Asp Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Glu Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 209
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 209
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatttcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccatggaag   420
gagctatcga cttactcttc ggctcgagct ggggctagtg cactagctaa tgctctatcg   480
aaggagctag agagtacaa tatcccggtg ttcgctatcg ctccgaatta cctacactcg   540
ggggattcgc cgtactatta ccctctgag ccgtggaaga cttctccgga gcacgtggct   600
cacgtgcgta aggtgactgc tctacaacga ctagggactc aaaaagagtt gggggaattg   660
gtgacgtttt tggcatctgg ctcttgtgat tatttgactg gccaggtgtt ttggttggca   720
ggcggctttc ccgtcatcga acgttggccc ggcatgcccg aataa              765

<210> SEQ ID NO 210
<211> LENGTH: 254
<212> TYPE: PRT
<213> ORGANISM: Artificial Sequence
<220> FEATURE:
<223> OTHER INFORMATION: Variant of halohydrin dehalogenase from A.

radiobacter

<400> SEQUENCE: 210

| Met<br>1 | Ser | Thr | Ala | Ile<br>5 | Val | Thr | Asn | Val | Lys<br>10 | His | Phe | Gly | Gly | Met<br>15 | Gly |
|---|---|---|---|---|---|---|---|---|---|---|---|---|---|---|---|
| Ser | Ala | Leu | Arg<br>20 | Leu | Ser | Glu | Ala | Gly<br>25 | His | Thr | Val | Ala | Cys<br>30 | His | Asp |
| Glu | Ser | Phe<br>35 | Lys | His | Gln | Asp | Glu<br>40 | Leu | Glu | Ala | Phe | Ala<br>45 | Glu | Thr | Tyr |
| Pro | Gln<br>50 | Leu | Ile | Pro | Met | Ser<br>55 | Glu | Gln | Glu | Pro | Ala<br>60 | Glu | Leu | Ile | Glu |
| Ala<br>65 | Val | Thr | Ser | Ala | Leu<br>70 | Gly | His | Val | Asp | Val<br>75 | Leu | Val | Ser | Asn | Asp<br>80 |
| Ile | Ala | Pro | Val | Glu<br>85 | Phe | Arg | Pro | Ile | Asp<br>90 | Lys | Tyr | Ala | Val | Glu<br>95 | Asp |
| Tyr | Arg | Asp | Thr<br>100 | Val | Glu | Ala | Leu | Gln<br>105 | Ile | Lys | Pro | Phe | Ala<br>110 | Leu | Val |
| Asn | Ala | Val<br>115 | Ala | Ser | Gln | Met | Lys<br>120 | Lys | Arg | Lys | Ser | Gly<br>125 | His | Ile | Ile |
| Phe | Ile<br>130 | Thr | Ser | Ala | Ala | Pro<br>135 | Phe | Gly | Pro | Trp | Lys<br>140 | Glu | Leu | Ser | Thr |
| Tyr<br>145 | Ser | Ser | Ala | Arg | Ala<br>150 | Gly | Ala | Ser | Ala | Leu<br>155 | Ala | Asn | Ala | Leu | Ser<br>160 |
| Lys | Glu | Leu | Gly | Glu<br>165 | Tyr | Asn | Ile | Pro | Val<br>170 | Phe | Ala | Ile | Ala | Pro<br>175 | Asn |
| Tyr | Leu | His | Ser<br>180 | Gly | Asp | Ser | Pro | Tyr<br>185 | Tyr | Tyr | Pro | Ser | Glu<br>190 | Pro | Trp |
| Lys | Thr | Ser<br>195 | Pro | Glu | His | Val | Ala<br>200 | His | Val | Arg | Lys | Val<br>205 | Thr | Ala | Leu |
| Gln | Arg<br>210 | Leu | Gly | Thr | Gln | Lys<br>215 | Glu | Leu | Gly | Glu | Leu<br>220 | Val | Thr | Phe | Leu |
| Ala<br>225 | Ser | Gly | Ser | Cys | Asp<br>230 | Tyr | Leu | Thr | Gly | Gln<br>235 | Val | Phe | Trp | Leu | Ala<br>240 |
| Gly | Gly | Phe | Pro | Val<br>245 | Ile | Glu | Arg | Trp | Pro<br>250 | Gly | Met | Pro | Glu | | |

<210> SEQ ID NO 211
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 211

```
atgagcaccg ctattgtcac caacgtcaaa cattttggag gtatgggtag cgctctgtgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaacatcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttctg gccatggaag     420
gagctatcga cttactcttc ggctcgagct ggggctagtg cactagctaa tgctctatcg     480
aaggagctag gagagtacaa tatcccggtg ttcgctatcg ctccgaatta cctacactcg     540
```

```
ggggattcgc cgtactatta cccctctgag ccgtggaaga cttctccgga gcacgtggct    600
cacgtgcgta aggtgactgc tctacaacga ctagggactc aaaaagagtt ggggaattg     660 gtgacgtttt tggcatctgg ctcttgtgat tatttgactg ccaggtgtt ttggttggca     720 ggcggctttc ccgtcatcga acgttggccc ggcatgcccg aataa                     765
```

<210> SEQ ID NO 212
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 212

```
Met Ser Thr Ala Ile Val Thr Asn Val Lys His Phe Gly Gly Met Gly
1               5                   10                  15

Ser Ala Leu Cys Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Leu Val Ser Asn Asp
65                  70                  75                  80

Ile Ala Pro Val Glu His Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Trp Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 213
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 213

```
atgagcaccg ctattgtcac caacgtcaaa cattttggag gtatgggtag cgctctgcgt    60
```

-continued

```
ctgagcgaag ctggtcatac cgtcgcttgc catgatgaaa gctttaagca tcaggatgaa      120
ctagaagctt ttgctgaaac ctacccacag ctgataccaa tgagcgaaca ggaaccagct      180
gaactgattg aagctgtcac cagcgctctt ggtcatgtcg atgtcctggt cagcaacgat      240
atcgcgcctg tggaatggcg gccaatcgat aaatacgctg tcgaggatta cagggatact      300
gtcgaagctc tgcagatcaa gccatttgct ctagtgaatg ctgtcgcttc gcaaatgaag      360
aagcgaaagt cggggcacat catcttcatc acttcggctt gcccgttcgg gccatggaag      420
gagctatcga cttactcttc ggctcgagct ggggctagtg cactagctaa tgctctatcg      480
aaggagctag gagagtacaa tatcccggtg ttcgctatcg ctccgaatta cctacactcg      540
ggggattcgc cgtactatta cccctctgag ccgtggaaga cttctccgga gcacgtggct      600
cacgtgcgta aggtgactgc tctacaacga ctagggactc aaaaagagtt gggggaattg      660
gtgacgtttt tggcatctgg ctcttgtgat tatttgactg gccaggtgtt ttggttggca      720
ggcggctttc ccgtcatcga acgttggccc ggcatgcccg aataa                      765
```

<210> SEQ ID NO 214
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 214

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
                20                  25                  30

Glu Ser Phe Lys His Gln Asp Glu Leu Glu Ala Phe Ala Glu Thr Tyr
            35                  40                  45

Pro Gln Leu Ile Pro Met Ser Glu Gln Glu Pro Ala Glu Leu Ile Glu
        50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Cys Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

```
Gly Gly Phe Pro Val Ile Glu Arg Trp Pro Gly Met Pro Glu
                245                 250

<210> SEQ ID NO 215
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 215
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcaaccctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgaatta cctacactcg      540
ggggattcgc cgtactatta cccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                     765

<210> SEQ ID NO 216
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 216

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Asn Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
```

```
         145                 150                 155                 160
Lys Glu Leu Gly Glu Tyr Asn Ile Pro Val Phe Ala Ile Ala Pro Asn
                165                 170                 175
Tyr Leu His Ser Gly Asp Ser Pro Tyr Tyr Pro Ser Glu Pro Trp
                180                 185                 190
Lys Thr Ser Pro Glu His Val Ala His Val Arg Lys Val Thr Ala Leu
                195                 200                 205
Gln Arg Leu Gly Thr Gln Lys Glu Leu Gly Glu Leu Val Thr Phe Leu
        210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                245                 250

<210> SEQ ID NO 217
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 217
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atctggcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccatggaag   420
gagctatcga cttactcttc ggctcgagct ggggctagtg cactagctaa tgctctatcg   480
aaggagctag agagtacaa tatcccggtg ttcgctatcg ctccgaatta cctacactcg   540
ggggattcgc cgtactatta cccctctgag ccgtggaaga cttctccgga gcacgtggct   600
cacgtgcgta aggtgactgc tctacaacga ctagggactc aaaaagagtt ggggaattg   660 gtgacgtttt tggcatctgg ctcttgtgat tatttgactg gccaggtgtt ttggttggca   720
ggcggctttc ccgtcatcga acgttggccc ggcatgcccg aataa              765

<210> SEQ ID NO 218
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 218

Met Ser Thr Ala Ile Val Thr Asn Val Lys His Phe Gly Gly Met Gly
1               5                  10                  15
Ser Ala Leu Arg Leu Ser Glu Ala Gly His Thr Val Ala Cys His Asp
                20                  25                  30
Glu Ser Phe Lys His Gln Asp Glu Leu Glu Ala Phe Ala Glu Thr Tyr
            35                  40                  45
Pro Gln Leu Ile Pro Met Ser Glu Gln Glu Pro Ala Glu Leu Ile Glu
        50                  55                  60
```

```
Ala Val Thr Ser Ala Leu Gly His Val Asp Val Leu Val Ser Asn Asp
 65                  70                  75                  80

Ile Trp Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 219
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 219

```
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgccta ttgaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccatggaag   420
gagctatcga cttactcttc ggctcgagct ggggctagtg cactagctaa tgctctatcg   480
aaggagctag agagtacaa tatcccggtg ttcgctatcg ctccgaatta cctacactcg   540
ggggattcgc cgtactatta ccctctgag ccgtggaaga cttctccgga gcacgtggct   600
cacgtgcgta aggtgactgc tctacaacga ctagggactc aaaaagagtt ggggggaattg   660
gtgacgtttt tggcatctgg ctcttgtgat tatttgactg gccaggtgtt ttggttggca   720
ggcggctttc ccgtcatcga acgttggccc ggcatgcccg aataa              765
```

<210> SEQ ID NO 220
<211> LENGTH: 254
<212> TYPE: PRT
<213> ORGANISM: Artificial Sequence
<220> FEATURE:
<223> OTHER INFORMATION: Variant of halohydrin dehalogenase from A.

radiobacter

<400> SEQUENCE: 220

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65              70                  75                  80

Ile Ala Pro Ile Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 221
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 221
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggcta ttccgttcgg gccatggaag   420
gagctatcga cttactcttc ggctcgagct ggggctagtg cactagctaa tgctctatcg   480
aaggagctag gagagtacaa tatcccggtg ttcgctatcg ctccgaatta cctacactcg   540

```
ggggattcgc cgtactatta cccctctgag ccgtggaaga cttctccgga gcacgtggct    600
cacgtgcgta aggtgactgc tctacaacga ctagggactc aaaaagagtt ggggaattg     660 gtgacgtttt tggcatctgg ctcttgtgat tatttgactg ccaggtgtt ttggttggca     720 ggcggctttc ccgtcatcga acgttggccc ggcatgcccg aataa                    765
```

<210> SEQ ID NO 222
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 222

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ile Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 223
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 223

```
atgagcaccg ctattgtcac caacgtcaaa cattttggag gtatgggtag cgctctgcgt    60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggcta aaccgttcgg gccatggaag    420
gagctatcga cttactcttc ggctcgagct ggggctagtg cactagctaa tgctctatcg    480
aaggagctag gagagtacaa tatcccggtg ttcgctatcg ctccgaatta cctacactcg    540
ggggattcgc cgtactatta cccctctgag ccgtggaaga cttctccgga gcacgtggct    600
cacgtgcgta aggtgactgc tctacaacga ctagggactc aaaaagagtt ggggaattg    660 gtgacgtttt tggcatctgg ctcttgtgat tatttgactg gccaggtgtt ttggttggca    720
ggcggctttc ccgtcatcga acgttggccc ggcatgcccg aataa              765
```

<210> SEQ ID NO 224
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 224

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Lys Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

```
Gly Gly Phe Pro Val Ile Glu Arg Trp Pro Gly Met Pro Glu
                245                 250

<210> SEQ ID NO 225
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 225
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctc tgccgttcgg accatggaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta cccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                    765

<210> SEQ ID NO 226
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 226

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Leu Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
```

```
                145                 150                 155                 160
Lys Glu Leu Gly Glu Tyr Asn Ile Pro Val Phe Ala Ile Ala Pro Asn
                    165                 170                 175
Tyr Leu His Ser Gly Asp Ser Pro Tyr Tyr Pro Ser Glu Pro Trp
                180                 185                 190
Lys Thr Ser Pro Glu His Val Ala His Val Arg Lys Val Thr Ala Leu
                    195                 200                 205
Gln Arg Leu Gly Thr Gln Lys Glu Leu Gly Glu Leu Val Thr Phe Leu
        210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                    245                 250

<210> SEQ ID NO 227
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 227
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg tgccgttcgg accatggaag   420
gagctatcga cttactcttc ggctcgagct ggggctagtg cactagctaa tgctctatcg   480
aaggagctag agagtacaa tatcccggtg ttcgctatcg ctccgaatta cctacactcg   540
ggggattcgc cgtactatta cccctctgag ccgtggaaga cttctccgga gcacgtggct   600
cacgtgcgta aggtgactgc tctacaacga ctagggactc aaaaagagtt ggggaattg   660
gtgacgtttt tggcatctgg ctcttgtgat tatttgactg gccaggtgtt ttggttggca   720
ggcggctttc ccgtcatcga acgttggccc ggcatgcccg aataa              765

<210> SEQ ID NO 228
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 228

Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
                20                  25                  30
Glu Ser Phe Lys His Gln Asp Glu Leu Glu Ala Phe Ala Glu Thr Tyr
            35                  40                  45
Pro Gln Leu Ile Pro Met Ser Glu Gln Glu Pro Ala Glu Leu Ile Glu
        50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Arg Lys Ser Gly His Ile Ile
        115                 120                 125

Phe Ile Thr Ser Ala Val Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
            195                 200                 205

Gln Arg Leu Gly Thr Lys Glu Leu Gly Glu Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 229
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 229
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagggctcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta ccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                     765

<210> SEQ ID NO 230
<211> LENGTH: 254
<212> TYPE: PRT
<213> ORGANISM: Artificial Sequence
<220> FEATURE:
<223> OTHER INFORMATION: Variant of halohydrin dehalogenase from A.
``` radiobacter

<400> SEQUENCE: 230

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65              70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Gly Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 231
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 231
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctt ttccgttcgg gccatggaag     420
gagctatcga cttactcttc ggctcgagct ggggctagtg cactagctaa tgctctatcg     480
aaggagctag gagagtacaa tatcccggtg ttcgctatcg ctccgaatta cctacactcg     540

```
ggggattcgc cgtactatta cccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctttc ccgtcatcga acgttggccc ggcatgcccg aataa                    765
```

<210> SEQ ID NO 232
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 232

```
Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
Ala Val Thr Ser Ala Leu Gly His Val Asp Val Leu Val Ser Asn Asp
65                  70                  75                  80
Ile Ala Pro Val Glu Trp Arg Pro Ile Asp Lys Tyr Ala Val Glu Asp
                85                  90                  95
Tyr Arg Asp Thr Val Glu Ala Leu Gln Ile Lys Pro Phe Ala Leu Val
            100                 105                 110
Asn Ala Val Ala Ser Gln Met Lys Lys Arg Lys Ser Gly His Ile Ile
        115                 120                 125
Phe Ile Thr Ser Ala Phe Pro Phe Gly Pro Trp Lys Glu Leu Ser Thr
    130                 135                 140
Tyr Ser Ser Ala Arg Ala Gly Ala Ser Ala Leu Ala Asn Ala Leu Ser
145                 150                 155                 160
Lys Glu Leu Gly Glu Tyr Asn Ile Pro Val Phe Ala Ile Ala Pro Asn
                165                 170                 175
Tyr Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
        195                 200                 205
Gln Arg Leu Gly Thr Gln Lys Glu Leu Gly Glu Leu Val Thr Phe Leu
    210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                245                 250
```

<210> SEQ ID NO 233
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 233

```
atgagcaccg ctattgtcac caacgtcaaa cattttggag gtatgggtag cgctctgcgt    60
```

-continued

```
ctgagcgaag ctggtcatac cgtcgcttgc catgatgaaa gctttaagca tcaggatgaa      120
ctagaagctt ttgctgaaac ctacccacag ctgataccaa tgagcgaaca ggaaccagct      180
gaactgattg aagctgtcac cagcgctctt ggtcatgtcg atgtcctggt cagcaacgat      240
atcgcgcctg tggaatggcg gccaatcgat aaatacgctg tcgaggatta cagggatact      300
gtcgaagctc tgcagatcaa gccatttgct ctagtgaatg ctgtcgcttc gcaaatgaag      360
aagcgaaagt cggggcacat catcttcatc acttcggcta tgccgttcgg accatggaag      420
gagctatcga cttactcttc ggctcgagct ggggctagtg cactagctaa tgctctatcg      480
aaggagctag gagagtacaa tatcccggtg ttcgctatcg ctccgaatta cctacactcg      540
ggggattcgc cgtactatta cccctctgag ccgtggaaga cttctccgga gcacgtggct      600
cacgtgcgta aggtgactgc tctacaacga ctagggactc aaaaagagtt gggggaattg      660
gtgacgtttt tggcatctgg ctcttgtgat tatttgactg ccaggtgtt ttggttggca      720 ggcggctttc ccgtcatcga acgttggccc ggcatgcccg aataa                     765
```

<210> SEQ ID NO 234
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 234

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Met Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

```
<210> SEQ ID NO 235
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 235
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagatttcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta ccctctgag ccgtggaaga cttctccgga gcacgtggct     600
cacgtgcgta aggtgaccgc tctacaacga ctagggactc aaaaagagtt gggggaattg     660
gtgacgtttt tggcatctgg ctcttgtgat tatttgactg ccaggtgtt ttggttggca     720 ggcggctttc ccgtcatcga acgttggccc ggcatgcccg aataa                    765

<210> SEQ ID NO 236
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 236

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Ile Ser Thr
    130                 135                 140

Tyr Ser Ser Ala Arg Ala Gly Ala Ser Ala Leu Ala Asn Ala Leu Ser
```

```
                145                 150                 155                 160
Lys Glu Leu Gly Glu Tyr Asn Ile Pro Val Phe Ala Ile Ala Pro Asn
                    165                 170                 175

Tyr Leu His Ser Gly Asp Ser Pro Tyr Tyr Pro Ser Glu Pro Trp
                180                 185                 190

Lys Thr Ser Pro Glu His Val Ala His Val Arg Lys Val Thr Ala Leu
                195                 200                 205

Gln Arg Leu Gly Thr Gln Lys Glu Leu Gly Glu Leu Val Thr Phe Leu
                210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                    245                 250

<210> SEQ ID NO 237
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 237
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagatgtcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta ccccctctgag ccgtggaaga cttctccgga gcacgtggct     600
cacgtgcgta aggtgactgc tctacaacga ctagggactc aaaaagagtt ggggaattg     660 gtgacgtttt tggcatctgg ctcttgtgat tatttgactg gccaggtgtt ttggttggca     720
ggcggctttc ccgtcatcga acgttggccc ggcatgcccg aataa                    765

<210> SEQ ID NO 238
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 238

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
                20                  25                  30

Glu Ser Phe Lys His Gln Asp Glu Leu Glu Ala Phe Ala Glu Thr Tyr
            35                  40                  45

Pro Gln Leu Ile Pro Met Ser Glu Gln Glu Pro Ala Glu Leu Ile Glu
        50                  55                  60
```

Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Met Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Glu Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 239
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 239
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagaactcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta ccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                     765

<210> SEQ ID NO 240
<211> LENGTH: 254
<212> TYPE: PRT
<213> ORGANISM: Artificial Sequence
<220> FEATURE:
<223> OTHER INFORMATION: Variant of halohydrin dehalogenase from A.

radiobacter

<400> SEQUENCE: 240

| Met | Ser | Thr | Ala | Ile | Val | Thr | Asn | Val | Lys | His | Phe | Gly | Gly | Met | Gly |
|---|---|---|---|---|---|---|---|---|---|---|---|---|---|---|---|
| 1 | | | | 5 | | | | | 10 | | | | | 15 | |

| Ser | Ala | Leu | Arg | Leu | Ser | Glu | Ala | Gly | His | Thr | Val | Ala | Cys | His | Asp |
|---|---|---|---|---|---|---|---|---|---|---|---|---|---|---|---|
| | | | 20 | | | | | 25 | | | | | 30 | | |

| Glu | Ser | Phe | Lys | His | Gln | Asp | Glu | Leu | Glu | Ala | Phe | Ala | Glu | Thr | Tyr |
|---|---|---|---|---|---|---|---|---|---|---|---|---|---|---|---|
| | | | | 35 | | | | | 40 | | | | | 45 | |

| Pro | Gln | Leu | Ile | Pro | Met | Ser | Glu | Gln | Glu | Pro | Ala | Glu | Leu | Ile | Glu |
|---|---|---|---|---|---|---|---|---|---|---|---|---|---|---|---|
| | 50 | | | | | 55 | | | | | 60 | | | | |

| Ala | Val | Thr | Ser | Ala | Leu | Gly | His | Val | Asp | Val | Leu | Val | Ser | Asn | Asp |
|---|---|---|---|---|---|---|---|---|---|---|---|---|---|---|---|
| 65 | | | | | 70 | | | | | 75 | | | | | 80 |

| Ile | Ala | Pro | Val | Glu | Trp | Arg | Pro | Ile | Asp | Lys | Tyr | Ala | Val | Glu | Asp |
|---|---|---|---|---|---|---|---|---|---|---|---|---|---|---|---|
| | | | | 85 | | | | | 90 | | | | | 95 | |

| Tyr | Arg | Asp | Thr | Val | Glu | Ala | Leu | Gln | Ile | Lys | Pro | Phe | Ala | Leu | Val |
|---|---|---|---|---|---|---|---|---|---|---|---|---|---|---|---|
| | | | 100 | | | | | 105 | | | | | 110 | | |

| Asn | Ala | Val | Ala | Ser | Gln | Met | Lys | Lys | Arg | Lys | Ser | Gly | His | Ile | Ile |
|---|---|---|---|---|---|---|---|---|---|---|---|---|---|---|---|
| | | 115 | | | | | 120 | | | | | 125 | | | |

| Phe | Ile | Thr | Ser | Ala | Ala | Pro | Phe | Gly | Pro | Trp | Lys | Glu | Asn | Ser | Thr |
|---|---|---|---|---|---|---|---|---|---|---|---|---|---|---|---|
| 130 | | | | | 135 | | | | | 140 | | | | | |

| Tyr | Ser | Ser | Ala | Arg | Ala | Gly | Ala | Ser | Ala | Leu | Ala | Asn | Ala | Leu | Ser |
|---|---|---|---|---|---|---|---|---|---|---|---|---|---|---|---|
| 145 | | | | | 150 | | | | | 155 | | | | | 160 |

| Lys | Glu | Leu | Gly | Glu | Tyr | Asn | Ile | Pro | Val | Phe | Ala | Ile | Ala | Pro | Asn |
|---|---|---|---|---|---|---|---|---|---|---|---|---|---|---|---|
| | | | | 165 | | | | | 170 | | | | | 175 | |

| Tyr | Leu | His | Ser | Gly | Asp | Ser | Pro | Tyr | Tyr | Pro | Ser | Glu | Pro | Trp |
|---|---|---|---|---|---|---|---|---|---|---|---|---|---|---|
| | | | 180 | | | | | 185 | | | | | 190 | |

| Lys | Thr | Ser | Pro | Glu | His | Val | Ala | His | Val | Arg | Lys | Val | Thr | Ala | Leu |
|---|---|---|---|---|---|---|---|---|---|---|---|---|---|---|---|
| | | | 195 | | | | | 200 | | | | | 205 | | |

| Gln | Arg | Leu | Gly | Thr | Gln | Lys | Glu | Leu | Gly | Glu | Leu | Val | Thr | Phe | Leu |
|---|---|---|---|---|---|---|---|---|---|---|---|---|---|---|---|
| | 210 | | | | | 215 | | | | | 220 | | | | |

| Ala | Ser | Gly | Ser | Cys | Asp | Tyr | Leu | Thr | Gly | Gln | Val | Phe | Trp | Leu | Ala |
|---|---|---|---|---|---|---|---|---|---|---|---|---|---|---|---|
| 225 | | | | | 230 | | | | | 235 | | | | | 240 |

| Gly | Gly | Phe | Pro | Val | Ile | Glu | Arg | Trp | Pro | Gly | Met | Pro | Glu |
|---|---|---|---|---|---|---|---|---|---|---|---|---|---|
| | | | | 245 | | | | | 250 | | | | |

<210> SEQ ID NO 241
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 241

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagtgctcga cttactcttc ggctcgagct ggggctagtg cactagctaa tgctctatcg     480
aaggagctag gagagtacaa tatcccggtg ttcgctatcg ctccgaatta cctacactcg     540
```

```
ggggattcgc cgtactatta ccccctctgag ccgtggaaga cttctccgga gcacgtggct      600
cacgtgcgta aggtgactgc tctacaacga ctagggactc aaaaagagtt gggggaattg      660
gtgacgtttt tggcatctgg ctcttgtgat tatttgactg ccaggtgtt ttggttggca       720 ggcggctttc ccgtcatcga acgttggccc ggcatgcccg aataa                      765
```

<210> SEQ ID NO 242
<211> LENGTH: 254
<212> TYPE: PRT
<213> ORGANISM: Artificial Sequence
<220> FEATURE:
<223> OTHER INFORMATION: Variant of halohydrin dehalogenase from A.
     radiobacter

<400> SEQUENCE: 242

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Cys Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 243
<211> LENGTH: 765
<212> TYPE: DNA
<213> ORGANISM: Artificial Sequence
<220> FEATURE:
<223> OTHER INFORMATION: Variant of halohydrin dehalogenase from A.
     radiobacter

<400> SEQUENCE: 243

```
atgagcaccg ctattgtcac caacgtcaaa cattttggag gtatgggtag cgctctgcgt      60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag gagagtacaa tatcccggtg ttcgctatcg ctccgaatta cctacactcg    540
ggggattcgc cgtactatta ccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctttc ccgtcatcga acgttggccc ggcatgcccg aataa              765
```

<210> SEQ ID NO 244
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 244

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

Gly Gly Phe Pro Val Ile Glu Arg Trp Pro Gly Met Pro Glu
                245                 250

<210> SEQ ID NO 245
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 245

```
atgagcaccg ctattgtcac caacgtcaaa catatgggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcat cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgaatta cctacactcg      540
ggggattcgc cgtactatta cccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg ccaggtgtt ttggttggca      720
ggcggctttc ccgtcatcga acgttggccc ggcatgcccg aataa                      765
```

<210> SEQ ID NO 246
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 246

Met Ser Thr Ala Ile Val Thr Asn Val Lys His Met Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Ile Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser

```
            145                 150                 155                 160
Lys Glu Leu Gly Glu Tyr Asn Ile Pro Val Phe Ala Ile Ala Pro Asn
                165                 170                 175
Tyr Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
            195                 200                 205
Gln Arg Leu Gly Thr Gln Lys Glu Leu Gly Glu Leu Val Thr Phe Leu
        210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                245                 250

<210> SEQ ID NO 247
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 247
atgagcaccg ctattgtcac caacgtcaaa cattttggag gtatgggtag cgctctgcgt        60
ctgagcgaag ctggtcatac cgtcgcttgc catgatgaaa gctttaagca tcaggatgaa       120
ctagaagctt ttgctgaaac ctacccacag ctgataccaa tgagcgaaca ggaaccagct       180
gaactgattg aagctgtcac cagcgctctt ggtcatgtcg atgtcctggt cagcaacgat       240
atcgcgcctg tggaatggcg gccaatcgat aaatacgctg tcgaggatta cagggatact       300
gtcgaagctc tgcagatcaa gccatttgct ctagtgaatg ctgtcgcttc gcaaatgaag       360
aagcgaaagt cggggcacat catcttcatc acttcggctg ccccgttcgg gccatggaag       420
gagctatcga cttactcttc ggctcgagct ggggctagtg cactagctaa tgctctatcg       480
aaggagctag agagtacaa tatcccggtg ttcgctatcg cttt gaatta cctacactcg        540 ggggattcgc cgtactatta ccctctgag ccgtggaaga cttctccgga gcacgtggct        600
cacgtgcgta aggtgactgc tctacaacga ctagggactc aaaaagagtt ggggaattg        660 gtggcgtttt tggcatctgg ctcttgtgat tatttgactg gccaggtgtt ttggttggca       720
ggcggctttc ccgtcatcga acgttggccc ggcatgcccg aataa                       765

<210> SEQ ID NO 248
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 248

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60
```

-continued

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Leu Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 249
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 249
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggcta ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta cccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                    765

<210> SEQ ID NO 250
<211> LENGTH: 254
<212> TYPE: PRT
<213> ORGANISM: Artificial Sequence
<220> FEATURE:
<223> OTHER INFORMATION: Variant of halohydrin dehalogenase from A.

radiobacter

<400> SEQUENCE: 250

| Met | Ser | Thr | Ala | Ile | Val | Thr | Asn | Val | Lys | His | Phe | Gly | Gly | Met | Gly |
|---|---|---|---|---|---|---|---|---|---|---|---|---|---|---|---|
| 1 | | | | 5 | | | | | 10 | | | | | 15 | |

| Ser | Ala | Leu | Arg | Leu | Ser | Glu | Ala | Gly | His | Thr | Val | Ala | Cys | His | Asp |
|---|---|---|---|---|---|---|---|---|---|---|---|---|---|---|---|
| | | | 20 | | | | | 25 | | | | | 30 | | |

| Glu | Ser | Phe | Lys | His | Gln | Asp | Glu | Leu | Glu | Ala | Phe | Ala | Glu | Thr | Tyr |
|---|---|---|---|---|---|---|---|---|---|---|---|---|---|---|---|
| | | | 35 | | | | | 40 | | | | | 45 | | |

| Pro | Gln | Leu | Ile | Pro | Met | Ser | Glu | Gln | Glu | Pro | Ala | Glu | Leu | Ile | Glu |
|---|---|---|---|---|---|---|---|---|---|---|---|---|---|---|---|
| | 50 | | | | | 55 | | | | | 60 | | | | |

| Ala | Val | Thr | Ser | Ala | Leu | Gly | His | Val | Asp | Val | Leu | Val | Ser | Asn | Asp |
|---|---|---|---|---|---|---|---|---|---|---|---|---|---|---|---|
| 65 | | | | | 70 | | | | | 75 | | | | | 80 |

| Ile | Ala | Pro | Val | Glu | Trp | Arg | Pro | Ile | Asp | Lys | Tyr | Ala | Val | Glu | Asp |
|---|---|---|---|---|---|---|---|---|---|---|---|---|---|---|---|
| | | | | 85 | | | | | 90 | | | | | 95 | |

| Tyr | Arg | Asp | Thr | Val | Glu | Ala | Leu | Gln | Ile | Lys | Pro | Phe | Ala | Leu | Val |
|---|---|---|---|---|---|---|---|---|---|---|---|---|---|---|---|
| | | | 100 | | | | | 105 | | | | | 110 | | |

| Asn | Ala | Val | Ala | Ser | Gln | Met | Lys | Lys | Arg | Lys | Ser | Gly | His | Ile | Ile |
|---|---|---|---|---|---|---|---|---|---|---|---|---|---|---|---|
| | | 115 | | | | | 120 | | | | | 125 | | | |

| Phe | Ile | Thr | Ser | Ala | Thr | Pro | Phe | Gly | Pro | Trp | Lys | Glu | Leu | Ser | Thr |
|---|---|---|---|---|---|---|---|---|---|---|---|---|---|---|---|
| 130 | | | | | 135 | | | | | 140 | | | | | |

| Tyr | Ser | Ser | Ala | Arg | Ala | Gly | Ala | Ser | Ala | Leu | Ala | Asn | Ala | Leu | Ser |
|---|---|---|---|---|---|---|---|---|---|---|---|---|---|---|---|
| 145 | | | | | 150 | | | | | 155 | | | | | 160 |

| Lys | Glu | Leu | Gly | Glu | Tyr | Asn | Ile | Pro | Val | Phe | Ala | Ile | Ala | Pro | Asn |
|---|---|---|---|---|---|---|---|---|---|---|---|---|---|---|---|
| | | | 165 | | | | | 170 | | | | | 175 | | |

| Tyr | Leu | His | Ser | Gly | Asp | Ser | Pro | Tyr | Tyr | Tyr | Pro | Ser | Glu | Pro | Trp |
|---|---|---|---|---|---|---|---|---|---|---|---|---|---|---|---|
| | | | 180 | | | | | 185 | | | | | 190 | | |

| Lys | Thr | Ser | Pro | Glu | His | Val | Ala | His | Val | Arg | Lys | Val | Thr | Ala | Leu |
|---|---|---|---|---|---|---|---|---|---|---|---|---|---|---|---|
| | | 195 | | | | | 200 | | | | | 205 | | | |

| Gln | Arg | Leu | Gly | Thr | Gln | Lys | Glu | Leu | Gly | Glu | Leu | Val | Thr | Phe | Leu |
|---|---|---|---|---|---|---|---|---|---|---|---|---|---|---|---|
| | 210 | | | | | 215 | | | | | 220 | | | | |

| Ala | Ser | Gly | Ser | Cys | Asp | Tyr | Leu | Thr | Gly | Gln | Val | Phe | Trp | Leu | Ala |
|---|---|---|---|---|---|---|---|---|---|---|---|---|---|---|---|
| 225 | | | | | 230 | | | | | 235 | | | | | 240 |

| Gly | Gly | Phe | Pro | Val | Ile | Glu | Arg | Trp | Pro | Gly | Met | Pro | Glu |
|---|---|---|---|---|---|---|---|---|---|---|---|---|---|
| | | | 245 | | | | | 250 | | | | | |

<210> SEQ ID NO 251
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 251

```
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccatggaag   420
gagctatcga cttactcttc ggctcgagct ggggctagtg cactagctaa tgctctatcg   480
aaggagctag gagagtacaa tatcccggtg ttcgctatcg ctccgaatta ctgtcactcg   540
```

```
ggggattcgc cgtactatta ccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg ccaggtgtt ttggttggca    720 ggcggctttc ccgtcatcga acgttggccc ggcatgcccg aataa                    765
```

<210> SEQ ID NO 252
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 252

```
Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
Ala Val Thr Ser Ala Leu Gly His Val Asp Val Leu Val Ser Asn Asp
65                  70                  75                  80
Ile Ala Pro Val Glu Trp Arg Pro Ile Asp Lys Tyr Ala Val Glu Asp
                85                  90                  95
Tyr Arg Asp Thr Val Glu Ala Leu Gln Ile Lys Pro Phe Ala Leu Val
            100                 105                 110
Asn Ala Val Ala Ser Gln Met Lys Lys Arg Lys Ser Gly His Ile Ile
        115                 120                 125
Phe Ile Thr Ser Ala Ala Pro Phe Gly Pro Trp Lys Glu Leu Ser Thr
    130                 135                 140
Tyr Ser Ser Ala Arg Ala Gly Ala Ser Ala Leu Ala Asn Ala Leu Ser
145                 150                 155                 160
Lys Glu Leu Gly Glu Tyr Asn Ile Pro Val Phe Ala Ile Ala Pro Asn
                165                 170                 175
Tyr Cys His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
        195                 200                 205
Gln Arg Leu Gly Thr Gln Lys Glu Leu Gly Glu Leu Val Thr Phe Leu
    210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                245                 250
```

<210> SEQ ID NO 253
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 253

```
atgagcaccg ctattgtcac caacgtcaaa cattttggag gtatgggtag cgctctgcgt    60
```

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag gagagtacaa tatcccggtg ttcgctatcg ctccgaatta cgtgcactcg    540
ggggattcgc cgtactatta cccctctgag ccgtggaaga cttctccgga gcacgtggct    600
cacgtgcgta aggtgactgc tctacaacga ctagggactc aaaaagagtt ggggaattg    660 gtgacgtttt tggcatctgg ctcttgtgat tatttgactg gccaggtgtt ttggttggca    720
ggcggctttc ccgtcatcga acgttggccc ggcatgcccg aataa              765
```

<210> SEQ ID NO 254
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 254

```
Met Ser Thr Ala Ile Val Thr Asn Val Lys His Phe Gly Gly Met Gly
1               5                  10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Val His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

```
Gly Gly Phe Pro Val Ile Glu Arg Trp Pro Gly Met Pro Glu
                245                 250
```

<210> SEQ ID NO 255
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 255

```
atgagcaccg ctattgtcac caacgtcaaa catttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ttgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag agagtacaa tatcccggtg ttcgctatcg ctccgaatta ctgtcactcg    540
ggggattcgc cgtactatta cccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg ccaggtgtt ttggttggca     720
ggcggctttc ccgtcatcga acgttggccc ggcatgcccg aataa                    765
```

<210> SEQ ID NO 256
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 256

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Val Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
```

```
                145                 150                 155                 160
Lys Glu Leu Gly Glu Tyr Asn Ile Pro Val Phe Ala Ile Ala Pro Asn
                    165                 170                 175
Tyr Cys His Ser Gly Asp Ser Pro Tyr Tyr Pro Ser Glu Pro Trp
                180                 185                 190
Lys Thr Ser Pro Glu His Val Ala His Val Arg Lys Val Thr Ala Leu
                    195                 200                 205
Gln Arg Leu Gly Thr Gln Lys Glu Leu Gly Glu Leu Val Thr Phe Leu
        210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                    245                 250

<210> SEQ ID NO 257
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 257
atgagcaccg ctattgtcac caacgtcaaa cattttggag gtatgggtag cgctctgcgt        60
ctgagcgaag ctggtcatac cgtcgcttgc catgatgaaa gctttaagca tcaggatgaa       120
ctagaagctt ttgctgaaac ctacccacag ctgataccaa tgagcgaaca ggaaccagct       180
gaactgattg aagctgtcac cagcgctctt ggtcatgtcg atgtcctggt cagcaacgat       240
atcgcgcctg tggaatggcg gccaatcgat aaatacgctg tcgaggatta cagggatact       300
gtcgaagctc tgcagatcaa gccatttgct ctagtgaatg ctgtcgcttc gcaaatgaag       360
aagcgaaagt cggggcacat catcttcatc acttcggctg ccccgttcgg gccatggaag       420
gagctatcga cttactcttc ggctcgagct ggggctagtg cactagctaa tgctctatcg       480
aaggagctag agagtacaa tatcccggtg ttcgctatcg ctccgaatta cctacactcg        540
ggggattcgc cgtactttta ccctctgag ccgtggaaga cttctccgga gcacgtggct        600
cacgtgcgta aggtgactgc tctacaacga ctagggactc aaaaagagtt gggggaattg       660
gtgacgtttt tggcatctgg ctcttgtgat tatttgactg gccaggtgtt ttggttggca       720
ggcggctttc ccgtcatcga acgttggccc ggcatgcccg aataa                      765

<210> SEQ ID NO 258
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 258

Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Phe Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Glu Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 259
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 259
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatctaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta cccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgtgttccc ggcatgcccg aataa                    765

<210> SEQ ID NO 260
<211> LENGTH: 254
<212> TYPE: PRT
<213> ORGANISM: Artificial Sequence
<220> FEATURE:
<223> OTHER INFORMATION: Variant of halohydrin dehalogenase from A.
``` radiobacter

<400> SEQUENCE: 260

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65              70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Ser Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
            195                 200                 205

Gln Arg Leu Gly Thr Gln Lys Glu Leu Gly Glu Leu Val Thr Phe Leu
        210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Val Pro Gly Met Pro Glu
                245                 250

<210> SEQ ID NO 261
<211> LENGTH: 765
<212> TYPE: DNA
<213> ORGANISM: Artificial Sequence
<220> FEATURE:
<223> OTHER INFORMATION: Variant of halohydrin dehalogenase from A.
    radiobacter

<400> SEQUENCE: 261
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaactaag     420
gagctatcga cttactcttc ggctcgagct ggggctagtg cactagctaa tgctctatcg     480
aaggagctag agagtacaa tatcccggtg ttcgctatcg ctccgaatta cctacactcg     540

```
ggggattcgc cgtactatta ccctctgag ccgtggaaga cttctccgga gcacgtggct    600
cacgtgcgta aggtgactgc tctacaacga ctagggactc aaaaagagtt ggggaattg    660 gtgacgtttt tggcatctgg ctcttgtgat tatttgactg ccaggtgtt ttggttggca    720 ggcggctttc ccgtcatcga acgtcatccc ggcatgcccg aataa                   765
```

<210> SEQ ID NO 262  
<211> LENGTH: 254  
<212> TYPE: PRT  
<213> ORGANISM: Artificial Sequence  
<220> FEATURE:  
<223> OTHER INFORMATION: Variant of halohydrin dehalogenase from A. radiobacter

<400> SEQUENCE: 262

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Thr Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg His Pro Gly Met Pro Glu
                245                 250
```

<210> SEQ ID NO 263  
<211> LENGTH: 765  
<212> TYPE: DNA  
<213> ORGANISM: Artificial Sequence  
<220> FEATURE:  
<223> OTHER INFORMATION: Variant of halohydrin dehalogenase from A. radiobacter

<400> SEQUENCE: 263

```
atgagcaccg ctattgtcac caacgtcaaa cattttggag gtatgggtag cgctctgcgt    60
```

```
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccaatgaag   420
gagctatcga cttactcttc ggctcgagct ggggctagtg cactagctaa tgctctatcg   480
aaggagctag gagagtacaa tatcccggtg ttcgctatcg ctccgaatta cctacactcg   540
ggggattcgc cgtactatta cccctctgag ccgtggaaga cttctccgga gcacgtggct   600
cacgtgcgta aggtgactgc tctacaacga ctagggactc aaaaagagtt ggggaattg    660 gtgacggttt tggcatctgg ctcttgtgat tatttgactg gccaggtgtt ttggttggca   720 ggcggcttc ccgtcatcga acgtcctccc ggcatgcccg aataa                    765
```

<210> SEQ ID NO 264
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 264

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Met Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Val Leu
    210                 215                 220

Ala Ser Gly Ser Cys Asp Tyr Leu Thr Gly Gln Val Phe Trp Leu Ala
225                 230                 235                 240
```

Gly Gly Phe Pro Val Ile Glu Arg Pro Pro Gly Met Pro Glu
              245                 250

<210> SEQ ID NO 265
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 265
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccaacgaag   420
gagctatcga cttactcttc ggctcgagct ggggctagtg cactagctaa tgctctatcg   480
aaggagctag agagtacaa tatcccggtg ttcgctatcg ctccgaatta cctacactcg   540
ggggattcgc cgtactatta cccctctgag ccgtggaaga cttctccgga gcacgtggct   600
cacgtgcgta aggtgactgc tctacaacga ctagggactc aaaaagagtt gggggaattg   660
gtgacgtttt tggcatctgg ctcttgtgat tatttgactg ccaggtgtt ttggttggca   720 ggcggctttc ccgtcatcga acgttggccc ggcatgcccg aataa                  765

<210> SEQ ID NO 266
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 266

Met Ser Thr Ala Ile Val Thr Asn Val Lys His Phe Gly Gly Met Gly
 1               5                  10                  15

Ser Ala Leu Arg Leu Ser Glu Ala Gly His Thr Val Ala Cys His Asp
              20                  25                  30

Glu Ser Phe Lys His Gln Asp Glu Leu Glu Ala Phe Ala Glu Thr Tyr
          35                  40                  45

Pro Gln Leu Ile Pro Met Ser Glu Gln Glu Pro Ala Glu Leu Ile Glu
      50                  55                  60

Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                  85                  90                  95

Tyr Arg Asp Thr Val Glu Ala Leu Gln Ile Lys Pro Phe Ala Leu Val
             100                 105                 110

Asn Ala Val Ala Ser Gln Met Lys Lys Arg Lys Ser Gly His Ile Ile
         115                 120                 125

Phe Ile Thr Ser Ala Ala Pro Phe Gly Pro Thr Lys Glu Leu Ser Thr
     130                 135                 140

Tyr Ser Ser Ala Arg Ala Gly Ala Ser Ala Leu Ala Asn Ala Leu Ser

```
                145                 150                 155                 160
Lys Glu Leu Gly Glu Tyr Asn Ile Pro Val Phe Ala Ile Ala Pro Asn
                    165                 170                 175

Tyr Leu His Ser Gly Asp Ser Pro Tyr Tyr Pro Ser Glu Pro Trp
                180                 185                 190

Lys Thr Ser Pro Glu His Val Ala His Val Arg Lys Val Thr Ala Leu
            195                 200                 205

Gln Arg Leu Gly Thr Gln Lys Glu Leu Gly Glu Leu Val Thr Phe Leu
        210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                    245                 250

<210> SEQ ID NO 267
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 267
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccaatgaag   420
gagctatcga cttactcttc ggctcgagct ggggctagtg cactagctaa tgctctatcg   480
aaggagctag gagagtacaa tatcccggtg ttcgctatcg ctccgagtta cctacactcg   540
ggggattcgc cgtactatta ccccctctga gccgtggaaga cttctccgga gcacgtggct   600
cacgtgcgta aggtgactgc tctacaacga ctagggactc aaaaagagtt ggggaattg   660 gtgacgtttt tggcatctgg ctcttgtgat tatttgactg gccaggtgtt ttggttggca   720
ggcggctttc ccgtcatcga acgttggccc ggcatgcccg aataa              765

<210> SEQ ID NO 268
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 268

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Met Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Ser
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Glu Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 269
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 269
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatcgaag     420
gagctatcga cttactcttc ggctcgagct ggggctagtg cactagctaa tgctctatcg     480
aaggagctag agagtacaa tatcccggtg ttcgctatcg ctccgactta cctacactcg     540
ggggattcgc cgtactatta cccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                     765

<210> SEQ ID NO 270
<211> LENGTH: 254
<212> TYPE: PRT
<213> ORGANISM: Artificial Sequence
<220> FEATURE:
<223> OTHER INFORMATION: Variant of halohydrin dehalogenase from A.
``` radiobacter

<400> SEQUENCE: 270

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Ser Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Thr
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 271
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 271

```
atgagcaccg ctattgtcac caacgtcaaa cattttggag gtatgggtag cgctctgcgt      60
ctgagcgaag cttgtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaatgaag     420
gagctatcga cttactcttc ggctcgagct ggggctagtg cactagctaa tgctctatcg     480
aaggagctag gagagtacaa tatcccggtg ttcgctatcg ctccgactta cctacactcg     540
```

```
ggggattcgc cgtactatta ccctctgag ccgtggaaga cttctccgga gcacgtggct    600
cacgtgcgta aggtgactgc tctacaacga ctagggactc aaaaagagtt ggggggaattg   660 gtgacgtttt tggcatctgg ctcttgtgat tatttgactg gccaggtgtt ttggttggca    720
ggcggctttc ccgtcatcga acgttggccc ggcatgcccg aataa                   765
```

<210> SEQ ID NO 272
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 272

```
Met Ser Thr Ala Ile Val Thr Asn Val Lys His Phe Gly Gly Met Gly
1               5                  10                  15

Ser Ala Leu Arg Leu Ser Glu Ala Cys His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Met Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Thr
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 273
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 273

```
atgagcaccg ctattgtcac caacgtcaaa cattttggag gtatgggtag cgctctgcgt    60
```

-continued

```
ctgagcgaag ctggtcatac cgtcgcttgc catgatgaaa gctttaagca tcaggatgaa    120
ctagaagctt ttgcggaaac ctacccacag ctgataccaa tgagcgaaca ggaaccagct    180
gaactgattg aagctgtcac cagcgctctt ggtcatgtcg atgtcctggt cagcaacgtt    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccgtcgaag    420
gagctatcga cttactcttc ggctcgagct ggggctagtg cactagctaa tgctctatcg    480
aaggagctag gagagtacaa tatcccggtg ttcgctatcg ctccgaatta cctacactcg    540
ggggattcgc cgtactatta cccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctttc ccgtcatcga acgttggccc ggcatgcccg aataa               765
```

<210> SEQ ID NO 274
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 274

```
Met Ser Thr Ala Ile Val Thr Asn Val Lys His Phe Gly Gly Met Gly
1               5                  10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Val
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Ser Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

```
Gly Gly Phe Pro Val Ile Glu Arg Trp Pro Gly Met Pro Glu
                245                 250

<210> SEQ ID NO 275
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 275
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaagtgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccaatgaag   420
gagctatcga cttactcttc ggctcgagct ggggctagtg cactagctaa tgctctatcg   480
aaggagctag agagtacaa tatcccggtg ttcgctatcg ctccgaatta cctacactcg   540
ggggattcgc cgtactatta cccctctgag ccgtggaaga cttctccggg cacgtggct    600 cacgtgcgta aggtgactgc tctacaacga ctagggactc aaaagagtt ggggaattg     660 gtgacgtttt tggcatctgg ctcttgtgat tatttgactg ccaggtgtt ttggttggca    720 ggcggctttc ccgtcatcga acgttggccc ggcatgcccg aataa                   765

<210> SEQ ID NO 276
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 276

Met Ser Thr Ala Ile Val Thr Asn Val Lys His Phe Gly Gly Met Gly
1               5                  10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Val Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Met Lys Glu Leu Ser Thr
    130                 135                 140

Tyr Ser Ser Ala Arg Ala Gly Ala Ser Ala Leu Ala Asn Ala Leu Ser
```

```
                145                 150                 155                 160
Lys Glu Leu Gly Glu Tyr Asn Ile Pro Val Phe Ala Ile Ala Pro Asn
                    165                 170                 175

Tyr Leu His Ser Gly Asp Ser Pro Tyr Tyr Pro Ser Glu Pro Trp
            180                 185                 190

Lys Thr Ser Pro Gly His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 277
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 277
atgagcaccg ctattgtcac caacgtcaaa cattttggag gtatgggtag cgctctgcgt      60
ctgagcgaag ctggtcatac cgtcgcttgc catgatggaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcttggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccaacgaag    420
gagctatcga cttactcttc ggctcgagct ggggctagtg cactagctaa tgctctttcg    480
aaggagctag gagagtacaa tatcccggtg ttcgctatcg ctccgagtta cctacactcg    540
ggggattcgc cgtactatta ccccctctga gccgtggaaga cttctccgga gcacgtggct    600
cacgtgcgta aggtgactgc tctacaacga ctagggactc aaaaagagtt ggggaattg    660 gtgacgtttt tggcatctgg ctcttgtgat tatttgactg gccaggtgtt ttggttggca    720
ggcggctttc ccgtcatcga acgttggccc ggcatgcccg aataa                   765

<210> SEQ ID NO 278
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 278

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Gly Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Glu Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Arg Lys Ser Gly His Ile Ile
        115                 120                 125

Phe Ile Thr Ser Ala Ala Pro Phe Gly Pro Thr Lys Glu Leu Ser Thr
130                 135                 140

Tyr Ser Ser Ala Arg Ala Gly Ser Ala Leu Ala Asn Ala Leu Ser
145                 150                 155                 160

Lys Glu Leu Gly Glu Tyr Asn Ile Pro Val Phe Ala Ile Ala Pro Ser
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 279
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 279
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaacgaag     420
gagctatcga cttactcttc ggctcgagct ggggctagtg cactagctaa tgctctatcg     480
aaggagctag agagtacaa tatcccggtg ttcgctatcg ctccggatta cctacactcg     540
ggggattcgc cgtactatta ccctctgag ccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctttc ccgtcatcga acgttggccc ggcatgcccg aataa                     765

<210> SEQ ID NO 280
<211> LENGTH: 254
<212> TYPE: PRT
<213> ORGANISM: Artificial Sequence
<220> FEATURE:
<223> OTHER INFORMATION: Variant of halohydrin dehalogenase from A.
``` radiobacter

<400> SEQUENCE: 280

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Thr Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asp
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 281
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 281
atgagctccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaatgaag     420
gagctatcga cttactcttc ggctcgagct ggggctagtg cactagctaa tgctctatcg     480
aaggagctag gagagtacaa tatcccggtg ttcgctatcg ctccgagtta cctacactcg     540

```
ggggattcgc cgtactatta cccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctttc ccgtcatcga acgttggccc ggcatgcccg aataa                    765
```

<210> SEQ ID NO 282
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 282

```
Met Ser Ser Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Met Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Ser
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```

<210> SEQ ID NO 283
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 283

```
atgagcaccg ctattgtcac caacgtcaaa cattttggag gtatgggtag cgctctgcgt    60
```

-continued

```
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccaacgaag    420
gagctatcga cttactcttc ggctcgagct ggggctagtg cactagctaa tgctctatcg    480
aaggagctag gagagtacaa tatcccggtg ttcgctatcg ctccgagtta cctacactcg    540
ggggattcgc cgtactatta cccctctgag ccgtggaaga cttctccgga gcacgtggct    600
cacgtgcgta aggtgactgc tctacaacga ctagggactc aaaaagagtt ggggaattg    660 gtgacgtttt tggcatctgg ctcttgtgat tatttgactg gccaggtgtt ttggttggca    720
ggcggctttc ccgtcatcga acgttggccc ggcatgcccg aataa                    765
```

<210> SEQ ID NO 284
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 284

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Thr Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Ser
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

```
Gly Gly Phe Pro Val Ile Glu Arg Trp Pro Gly Met Pro Glu
                245                 250

<210> SEQ ID NO 285
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 285
atgagcaccg ctattgtcac caacgtcaaa cattttggag gtatgggtag cgctctgcgt    60
ctgagcgaag ctggtcatac cgtcgcttgc catgatgaaa gctttaagca tcaggatgaa   120
ctagaagctt ttgctgaaac ctacccacag ctgataccaa tgagcgaaca ggaaccagct   180
gaactgattg aagctgtcac cagcgctctt ggtcatgtcg atgtcctggt cagcaacgat   240
atcgcgcctg tggaatggcg gccaatcgat aaatacgctg tcgaggatta cagggatact   300
gtcgaagctc tgcagatcaa gccatttgct ctagtgaatg ctgtcgcttc gcaaatgaag   360
aagcgaaagt cggggcacat catcttcatc acttcggctg ccccgttcgg gccaatgaag   420
gagctatcga cttactcttc ggctcgagct ggggctagtg cactagctaa tgctctatcg   480
aaggagctag agagtacaa tatcccggtg ttcgctatcg ctccgaatta cctgcactcg    540
ggggattcgc cgtactatta cccctctgag ccgtggaaga cttctccgga gcacgtggca   600
cacgtgcgta aggtgactgc tctacaacga ctagggactc aaaaagagtt gggggaattg   660
gtgacgtttt tggcatctgg ctcttgtgat tatttgactg ccaggtgtt ttggttggca    720 ggcggctttc ccgtcatcga acgttggccc ggcatgcccg aataa                    765

<210> SEQ ID NO 286
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 286

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Met Lys Glu Leu Ser Thr
    130                 135                 140

Tyr Ser Ser Ala Arg Ala Gly Ala Ser Ala Leu Ala Asn Ala Leu Ser
```

```
            145                 150                 155                 160
Lys Glu Leu Gly Glu Tyr Asn Ile Pro Val Phe Ala Ile Ala Pro Asn
                165                 170                 175
Tyr Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
        195                 200                 205
Gln Arg Leu Gly Thr Gln Lys Glu Leu Gly Glu Leu Val Thr Phe Leu
    210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                245                 250
```

<210> SEQ ID NO 287
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 287

```
atgagcaccg ctattgtcac caacgtcaaa catttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcggggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaatgaag     420
gagctatcga cttactcttc ggctcgagct ggggctagtg cactagctaa tgctctatcg     480
aaggagctag gagagtacaa tatcccggtg ttcgctatcg ctccgaatta cctacactcg     540
ggggattcgc cgtactatta ccccctctga gccgtggaaga cttctccgga gcacgtggct     600
cacgtgcgta aggtgactgc tctacaacga ctagggactc aaaaagagtt gggggaattg     660
gtgacgtttt tggcatctgg ctcttgtgat tatttgactg gccaggtgtt ttggttggca     720
ggcggctcgc ccgtcatcga acgttggccc ggcatgcccg aataa                     765
```

<210> SEQ ID NO 288
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 288

```
Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
```

```
Ala Val Thr Ser Ala Leu Gly His Val Asp Val Leu Val Ser Asn Asp
 65                  70                  75                  80

Ile Ala Pro Val Glu Trp Arg Pro Ile Asp Lys Tyr Ala Val Gly Asp
                 85                  90                  95

Tyr Arg Asp Thr Val Glu Ala Leu Gln Ile Lys Pro Phe Ala Leu Val
            100                 105                 110

Asn Ala Val Ala Ser Gln Met Lys Arg Lys Ser Gly His Ile Ile
        115                 120                 125

Phe Ile Thr Ser Ala Ala Pro Phe Gly Pro Met Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Lys Glu Leu Gly Glu Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Ser Pro Val Ile Glu Arg Trp Pro Gly Met Pro Glu
                245                 250

<210> SEQ ID NO 289
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 289
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggactggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaatgaag     420
gagctatcga cttactcttc ggctcgagct ggggctagtg cactagctaa tgctctatcg     480
aaggagctag agagtacaa tgtcccggtg ttcgctatcg ctccgaatta cctacactcg     540
ggggattcgc cgtactatta cccctctgag ccgtggaaga cttctccgga gcacgtggct     600
cacgtgcgta aggtgactgc tctacaacga ctagggactc aaaaagagtt ggggaattg     660
gtgacgtttt tggcatctgg ctcttgtgat tatttgactg gccaggtgtt ttggttggca     720
ggcggctttc ccgtcatcga acgttggccc ggcatgcccg aataa                    765

<210> SEQ ID NO 290
<211> LENGTH: 254
<212> TYPE: PRT
<213> ORGANISM: Artificial Sequence
<220> FEATURE:
<223> OTHER INFORMATION: Variant of halohydrin dehalogenase from A.
``` radiobacter

<400> SEQUENCE: 290

| | | | | | | | | | | | | | | | |
|---|---|---|---|---|---|---|---|---|---|---|---|---|---|---|---|
| Met | Ser | Thr | Ala | Ile | Val | Thr | Asn | Val | Lys | His | Phe | Gly | Gly | Met | Gly |
| 1 | | | | 5 | | | | | 10 | | | | | 15 | |

| | | | | | | | | | | | | | | |
|---|---|---|---|---|---|---|---|---|---|---|---|---|---|---|
| Ser | Ala | Leu | Arg | Leu | Ser | Glu | Ala | Gly | His | Thr | Val | Ala | Cys | His | Asp |
| | | | 20 | | | | | 25 | | | | | 30 | | |

| Glu | Ser | Phe | Lys | His | Gln | Asp | Glu | Leu | Glu | Ala | Phe | Ala | Glu | Thr | Tyr |
|---|---|---|---|---|---|---|---|---|---|---|---|---|---|---|---|
| | | | 35 | | | | | 40 | | | | | 45 | | |

| Pro | Gln | Leu | Ile | Pro | Met | Ser | Glu | Gln | Glu | Pro | Ala | Glu | Leu | Ile | Glu |
|---|---|---|---|---|---|---|---|---|---|---|---|---|---|---|---|
| | 50 | | | | | 55 | | | | | 60 | | | | |

| Ala | Val | Thr | Ser | Ala | Leu | Gly | His | Val | Asp | Val | Leu | Val | Ser | Asn | Asp |
|---|---|---|---|---|---|---|---|---|---|---|---|---|---|---|---|
| 65 | | | | | 70 | | | | | 75 | | | | | 80 |

| Ile | Ala | Pro | Val | Asp | Trp | Arg | Pro | Ile | Asp | Lys | Tyr | Ala | Val | Glu | Asp |
|---|---|---|---|---|---|---|---|---|---|---|---|---|---|---|---|
| | | | | 85 | | | | | 90 | | | | | 95 | |

| Tyr | Arg | Asp | Thr | Val | Glu | Ala | Leu | Gln | Ile | Lys | Pro | Phe | Ala | Leu | Val |
|---|---|---|---|---|---|---|---|---|---|---|---|---|---|---|---|
| | | | 100 | | | | | 105 | | | | | 110 | | |

| Asn | Ala | Val | Ala | Ser | Gln | Met | Lys | Lys | Arg | Lys | Ser | Gly | His | Ile | Ile |
|---|---|---|---|---|---|---|---|---|---|---|---|---|---|---|---|
| | | 115 | | | | | 120 | | | | | 125 | | | |

| Phe | Ile | Thr | Ser | Ala | Ala | Pro | Phe | Gly | Pro | Met | Lys | Glu | Leu | Ser | Thr |
|---|---|---|---|---|---|---|---|---|---|---|---|---|---|---|---|
| 130 | | | | | 135 | | | | | 140 | | | | | |

| Tyr | Ser | Ser | Ala | Arg | Ala | Gly | Ala | Ser | Ala | Leu | Ala | Asn | Ala | Leu | Ser |
|---|---|---|---|---|---|---|---|---|---|---|---|---|---|---|---|
| 145 | | | | | 150 | | | | | 155 | | | | | 160 |

| Lys | Glu | Leu | Gly | Glu | Tyr | Asn | Val | Pro | Val | Phe | Ala | Ile | Ala | Pro | Asn |
|---|---|---|---|---|---|---|---|---|---|---|---|---|---|---|---|
| | | | | 165 | | | | | 170 | | | | | 175 | |

| Tyr | Leu | His | Ser | Gly | Asp | Ser | Pro | Tyr | Tyr | Tyr | Pro | Ser | Glu | Pro | Trp |
|---|---|---|---|---|---|---|---|---|---|---|---|---|---|---|---|
| | | | 180 | | | | | 185 | | | | | 190 | | |

| Lys | Thr | Ser | Pro | Glu | His | Val | Ala | His | Val | Arg | Lys | Val | Thr | Ala | Leu |
|---|---|---|---|---|---|---|---|---|---|---|---|---|---|---|---|
| | | 195 | | | | | 200 | | | | | 205 | | | |

| Gln | Arg | Leu | Gly | Thr | Gln | Lys | Glu | Leu | Gly | Glu | Leu | Val | Thr | Phe | Leu |
|---|---|---|---|---|---|---|---|---|---|---|---|---|---|---|---|
| 210 | | | | | 215 | | | | | 220 | | | | | |

| Ala | Ser | Gly | Ser | Cys | Asp | Tyr | Leu | Thr | Gly | Gln | Val | Phe | Trp | Leu | Ala |
|---|---|---|---|---|---|---|---|---|---|---|---|---|---|---|---|
| 225 | | | | | 230 | | | | | 235 | | | | | 240 |

| Gly | Gly | Phe | Pro | Val | Ile | Glu | Arg | Trp | Pro | Gly | Met | Pro | Glu |
|---|---|---|---|---|---|---|---|---|---|---|---|---|---|
| | | | | 245 | | | | | 250 | | | | |

<210> SEQ ID NO 291
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 291

```
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctg tggaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccaacgaag     420
gagctatcga cttactcttc ggctcgagct ggggctagtg cactagctaa tgctctatcg     480
aaggagctag gagagtacaa tatcccggtg ttcgctatcg ctccgaatta cctacactcg     540
```

```
ggggattcgc cgtactatta ccctctgag ccgtggaaga cttctccgga gcacgtggct    600
cgcgtgcgta aggtgactgc tctacaacga ctagggactc aaaaagagtt gggggaattg    660
gtgacgtttt tggcatctgg ctcctgtgat tatttgactg ccaggtgtt ttggttggca     720 ggcggctttc ccgtcatcga acgttggccc ggcatgcccg aataa                    765
```

```
<210> SEQ ID NO 292
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 292
```

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Thr Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Arg Val Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

```
<210> SEQ ID NO 293
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 293
atgagcaccg ctattgtcac caacgtcaaa cattttggag gtatgggtag cgctctgcgt    60
```

```
ctgagcgaag ctggtcacac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctg tggaatggcg gccaatcgat aaatacgctg tcgaggatta cagggatact    300
gtcgaagctc tgcagatcaa gccatttgct ctagcgaatg ctgtcgcttc gcaaatgaag    360
aagcgaaagt cggggcacat catcttcatc acttcggctg ccccgttcgg gccatcgaag    420
gagctatcga cttactcttc ggctcgagct ggggctagtg cactagctaa tgctctatcg    480
aaggagctag gagagtacaa tatcccggtg ttcgctatcg ctccgaatta cctacactcg    540
ggggattcgc cgtactatta cccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctttc ccgtcatcga acgttggccc ggcatgcccg aataa                    765
```

<210> SEQ ID NO 294
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 294

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Ala
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Ser Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240
```

```
Gly Gly Phe Pro Val Ile Glu Arg Trp Pro Gly Met Pro Glu
                245                 250
```

<210> SEQ ID NO 295
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 295

| | | | | |
|---|---|---|---|---|
| atgagcaccg | ctattgtcac | caacgtcaaa | cattttggag | gtatgggtag cgctctgcgt | 60 |
| ctgagcgaag | ctggtcatac | cgtcgcttgc | catgatgaaa | gctttaagca tcaggatgaa | 120 |
| ctagaagctt | ttgctgaaac | ctacccacag | ctgataccaa | tgagcgaaca ggaaccagct | 180 |
| gaactgattg | aagctgtcac | cagcgctctt | ggtcatgtcg | atgtcctggt cagcaacgat | 240 |
| atcgcgcctt | gcgaatggcg | gccaatcgat | aaatacgctg | tcgaggatta cagggatact | 300 |
| gtcgaagctc | tgcagatcaa | gccatttgct | ctagtgaatg | ctgtcgcttc gcaaatgaag | 360 |
| aagcgaaagt | cggggcacat | catcttcatc | acttcggctg | ccccgttcgg gccatggaag | 420 |
| gagctatcga | cttactcttc | ggctcgagct | ggggctagtg | cactagctaa tgctctatcg | 480 |
| aaggagctag | gagagtacaa | tatcccggtg | ttcgctatcg | ctccgaatta cctacactcg | 540 |
| ggggattcgc | cgtactatta | ccccctctgag | ccgtggaaga | cttctccgga gcacgtggct | 600 |
| cacgtgcgta | aggtgactgc | tctacaacga | ctagggactc | aaaaagagtt ggggaattg | 660 |
| gtgacgtttt | tggcatctgg | ctcttgtgat | tatttgactg | gccaggtgtt ttggttggca | 720 |
| ggcggctttc | ccgtcatcga | acgttggccc | ggcatgcccg | aataa | 765 |

<210> SEQ ID NO 296
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 296

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Cys Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
```

```
                145                 150                 155                 160
Lys Glu Leu Gly Glu Tyr Asn Ile Pro Val Phe Ala Ile Ala Pro Asn
                    165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 297
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 297
atgagcaccg ctattgtcac caacgtcaaa cattttggag gtatgggtag cgctctgcgt      60
ctgagcgaag ctggtcatac cgtcgcttgc catgatgaaa gctttaagca tcaggatgaa     120
ctagaagctt ttgctgaaac ctacccacag ctgataccaa tgagcgaaca ggaaccagct     180
gaactgattg aagctgtcac cagcgctctt ggtcatgtcg atgtcctggt cagcaacgat     240
atcgcgcctt tgaatggcg gccaatcgat aaatacgctg tcgaggatta cagggatact     300
gtcgaagctc tgcagatcaa gccatttgct ctagtgaatg ctgtcgcttc gcaaatgaag     360
aagcgaaagt cggggcacat catcttcatc acttcggctg ccccgttcgg gccatggaag     420
gagctatcga cttactcttc ggctcgagct ggggctagtg cactagctaa tgctctatcg     480
aaggagctag agagtacaa tatcccggtg ttcgctatcg ctccgaatta cctacactcg     540
ggggattcgc cgtactatta ccctctgag ccgtggaaga cttctccgga gcacgtggct     600
cacgtgcgta aggtgactgc tctacaacga ctagggactc aaaaagagtt ggggaattg     660 gtgacgtttt tggcatctgg ctcttgtgat tatttgactg gccaggtgtt ttggttggca     720
ggcggctttc ccgtcatcga acgttggccc ggcatgcccg aataa                    765

<210> SEQ ID NO 298
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 298

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60
```

Ala Val Thr Ser Ala Leu Gly His Val Asp Val Leu Val Ser Asn Asp
65                  70                  75                  80

Ile Ala Pro Phe Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
            195                 200                 205

Gln Arg Leu Gly Thr Lys Glu Leu Gly Leu Val Thr Phe Leu
210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 299
<211> LENGTH: 765
<212> TYPE: DNA
<213> ORGANISM: Artificial Sequence
<220> FEATURE:
<223> OTHER INFORMATION: Variant of halohydrin dehalogenase from A.
      radiobacter

<400> SEQUENCE: 299
atgagcaccg ctattgtcac caacgtcaaa cattttggag gtatgggtag cgctctgcgt     60
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
ctggcgcctg tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag agagtacaa tatcccggtg ttcgctatcg ctccgaatta cctacactcg    540
ggggattcgc cgtactatta ccctctgag ccgtggaaga cttctccgga gcacgtggct    600
cacgtgcgta aggtgactgc tctacaacga ctagggactc aaaaagagtt gggggaattg    660
gtgacgtttt tggcatctgg ctcttgtgat tatttgactg gccaggtgtt ttggttggca    720
ggcggctttc ccgtcatcga acgttggccc ggcatgcccg aataa              765

<210> SEQ ID NO 300
<211> LENGTH: 254
<212> TYPE: PRT
<213> ORGANISM: Artificial Sequence
<220> FEATURE:
<223> OTHER INFORMATION: Variant of halohydrin dehalogenase from A.

-continued radiobacter

<400> SEQUENCE: 300

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65              70                  75                  80

Leu Ala Pro Val Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Pro Ser Glu Pro Trp
            180                 185                 190

Lys Thr Ser Pro Glu His Val Ala His Val Arg Lys Val Thr Ala Leu
        195                 200                 205

Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250

<210> SEQ ID NO 301
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 301
atgagcaccg ctattgtcac caacgtcaaa cattttggag gtatgggtag cgctctgcgt     60
ctgagcgaag ctggtcatac cgtcgcttgc catgatgaaa gctttaagca tcaggatgaa    120
ctagaagctt ttgctgaaac ctacccacag ctgataccaa tgagcgaaca ggaaccagct    180
gaactgattg aagctgtcac cagcgctctt ggtcatgtcg atgtcctggt cagcaacgat    240
atcgcgcctc tggaatggcg gccaatcgat aaatacgctg tcgaggatta cagggatact    300
gtcgaagctc tgcagatcaa gccatttgct ctagtgaatg ctgtcgcttc gcaaatgaag    360
aagcgaaagt cggggcacat catcttcatc acttcggctg ccccgttcgg gccatggaag    420
gagctatcga cttactcttc ggctcgagct ggggctagtg cactagctaa tgctctatcg    480
aaggagctag gagagtacaa tatcccggtg ttcgctatcg ctccgaatta cctacactcg    540

```
ggggattcgc cgtactatta ccctctgag ccgtggaaga cttctccgga gcacgtggct      600
cacgtgcgta aggtgactgc tctacaacga ctagggactc aaaaagagtt gggggaattg      660
gtgacgtttt tggcatctgg ctcttgtgat tatttgactg ccaggtgtt ttggttggca       720 ggcggctttc ccgtcatcga acgttggccc ggcatgcccg aataa                     765
```

<210> SEQ ID NO 302
<211> LENGTH: 254
<212> TYPE: PRT
<213> ORGANISM: Artificial Sequence
<220> FEATURE:
<223> OTHER INFORMATION: Variant of halohydrin dehalogenase from A. radiobacter

<400> SEQUENCE: 302

```
Met Ser Thr Ala Ile Val Thr Asn Val Lys His Phe Gly Gly Met Gly
1               5                   10                  15
Ser Ala Leu Arg Leu Ser Glu Ala Gly His Thr Val Ala Cys His Asp
            20                  25                  30
Glu Ser Phe Lys His Gln Asp Glu Leu Glu Ala Phe Ala Glu Thr Tyr
        35                  40                  45
Pro Gln Leu Ile Pro Met Ser Glu Gln Glu Pro Ala Glu Leu Ile Glu
    50                  55                  60
Ala Val Thr Ser Ala Leu Gly His Val Asp Leu Val Ser Asn Asp
65                  70                  75                  80
Ile Ala Pro Leu Glu Trp Arg Pro Ile Asp Lys Tyr Ala Val Glu Asp
                85                  90                  95
Tyr Arg Asp Thr Val Glu Ala Leu Gln Ile Lys Pro Phe Ala Leu Val
            100                 105                 110
Asn Ala Val Ala Ser Gln Met Lys Lys Arg Lys Ser Gly His Ile Ile
        115                 120                 125
Phe Ile Thr Ser Ala Ala Pro Phe Gly Pro Trp Lys Glu Leu Ser Thr
    130                 135                 140
Tyr Ser Ser Ala Arg Ala Gly Ala Ser Ala Leu Ala Asn Ala Leu Ser
145                 150                 155                 160
Lys Glu Leu Gly Glu Tyr Asn Ile Pro Val Phe Ala Ile Ala Pro Asn
                165                 170                 175
Tyr Leu His Ser Gly Asp Ser Pro Tyr Tyr Pro Ser Glu Pro Trp
            180                 185                 190
Lys Thr Ser Pro Glu His Val Ala His Val Arg Lys Val Thr Ala Leu
        195                 200                 205
Gln Arg Leu Gly Thr Gln Lys Glu Leu Gly Glu Leu Val Thr Phe Leu
    210                 215                 220
Ala Ser Gly Ser Cys Asp Tyr Leu Thr Gly Gln Val Phe Trp Leu Ala
225                 230                 235                 240
Gly Gly Phe Pro Val Ile Glu Arg Trp Pro Gly Met Pro Glu
                245                 250
```

<210> SEQ ID NO 303
<211> LENGTH: 765
<212> TYPE: DNA
<213> ORGANISM: Artificial Sequence
<220> FEATURE:
<223> OTHER INFORMATION: Variant of halohydrin dehalogenase from A. radiobacter

<400> SEQUENCE: 303

```
atgagcaccg ctattgtcac caacgtcaaa cattttggag gtatgggtag cgctctgcgt      60
```

```
ctgagcgaag ctggtcatac cgtcgcttgc catgatgaaa gctttaagca tcaggatgaa      120
ctagaagctt ttgctgaaac ctacccacag ctgataccaa tgagcgaaca ggaaccagct      180
gaactgattg aagctgtcac cagcgctctt ggtcatgtcg atgtcctggt cagcaacgat      240
atcgcgccta tggaatggcg gccaatcgat aaatacgctg tcgaggatta cagggatact      300
gtcgaagctc tgcagatcaa gccatttgct ctagtgaatg ctgtcgcttc gcaaatgaag      360
aagcgaaagt cggggcacat catcttcatc acttcggctg ccccgttcgg gccatggaag      420
gagctatcga cttactcttc ggctcgagct ggggctagtg cactagctaa tgctctatcg      480
aaggagctag gagagtacaa tatcccggtg ttcgctatcg ctccgaatta cctacactcg      540
ggggattcgc cgtactatta cccctctgag ccgtggaaga cttctccgga gcacgtggct      600
cacgtgcgta aggtgactgc tctacaacga ctagggactc aaaaagagtt ggggaattg       660 gtgacgtttt tggcatctgg ctcttgtgat tatttgactg gccaggtgtt ttggttggca      720
ggcggctttc ccgtcatcga acgttggccc ggcatgcccg aataa                     765
```

```
<210> SEQ ID NO 304
<211> LENGTH: 254
<212> TYPE: PRT
<213> ORGANISM: Artificial Sequence
<220> FEATURE:
<223> OTHER INFORMATION: Variant of halohydrin dehalogenase from A.
      radiobacter

<400> SEQUENCE: 304
```

```
Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
            20                  25                  30

Glu Ser Phe Lys His Gln Asp Glu Leu Glu Ala Phe Ala Glu Thr Tyr
        35                  40                  45

Pro Gln Leu Ile Pro Met Ser Glu Gln Glu Pro Ala Glu Leu Ile Glu
    50                  55                  60

Ala Val Thr Ser Ala Leu Gly His Val Asp Val Leu Val Ser Asn Asp
65                  70                  75                  80

Ile Ala Pro Met Glu Trp Arg Pro Ile Asp Lys Tyr Ala Val Glu Asp
                85                  90                  95

Tyr Arg Asp Thr Val Glu Ala Leu Gln Ile Lys Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Ala Pro Phe Gly Pro Trp Lys Glu Leu Ser Thr
    130                 135                 140

Tyr Ser Ser Ala Arg Ala Gly Ala Ser Ala Leu Ala Asn Ala Leu Ser
145                 150                 155                 160

Lys Glu Leu Gly Glu Tyr Asn Ile Pro Val Phe Ala Ile Ala Pro Asn
                165                 170                 175

Tyr Leu His Ser Gly Asp Ser Pro Tyr Tyr Tyr Pro Ser Glu Pro Trp
            180                 185                 190

Lys Thr Ser Pro Glu His Val Ala His Val Arg Lys Val Thr Ala Leu
        195                 200                 205
```

```
Gln Arg Leu Gly Thr Gln Lys Glu Leu Gly Glu Leu Val Thr Phe Leu
    210                 215                 220

Ala Ser Gly Ser Cys Asp Tyr Leu Thr Gly Gln Val Phe Trp Leu Ala
225                 230                 235                 240

Gly Gly Phe Pro Val Ile Glu Arg Trp Pro Gly Met Pro Glu
                245                 250
```